US008728688B2

(12) United States Patent
Mizukawa et al.

(10) Patent No.: US 8,728,688 B2

(45) Date of Patent: May 20, 2014

(54) COLORED CURABLE COMPOSITION, COLOR FILTER AND METHOD OF PRODUCING THE SAME, AND DIPYRROMETHENE METAL COMPLEX COMPOUND AND TAUTOMER THEREOF

(75) Inventors: Yuki Mizukawa, Kanagawa (JP); Ryoji Goto, Kanagawa (JP); Junichi Ito, Kanagawa (JP); Hideki Takakuwa, Shizuoka-ken (JP); Shinichi Kanna, Shizuoka-ken (JP)

(73) Assignee: FUJIFILM Corporation, Tokyo (JP)

( * ) Notice: Subject to any disclaimer, the term of this patent is extended or adjusted under 35 U.S.C. 154(b) by 107 days.

(21) Appl. No.: 13/594,898

(22) Filed: Aug. 27, 2012

(65) Prior Publication Data

US 2012/0315579 A1 Dec. 13, 2012

Related U.S. Application Data

(62) Division of application No. 12/550,427, filed on Aug. 31, 2009, now Pat. No. 8,334,085.

(30) Foreign Application Priority Data

Sep. 2, 2008 (JP) ................................ 2008-225108
Sep. 29, 2008 (JP) ................................ 2008-251337

(51) Int. Cl.
*G03F 7/00* (2006.01)
*G02B 5/20* (2006.01)

(52) U.S. Cl.
USPC ............ 430/7; 430/270.1; 548/402; 548/403

(58) Field of Classification Search
None
See application file for complete search history.

(56) References Cited

U.S. PATENT DOCUMENTS

2003/0194646 A1* 10/2003 Ogiso et al. .............. 430/270.16
2008/0076044 A1 3/2008 Mizukawa et al.
2010/0055582 A1 3/2010 Mizukawa et al.

FOREIGN PATENT DOCUMENTS

| | | | |
|---|---|---|---|
| JP | 6-75375 | A | 3/1994 |
| JP | 11-352685 | A | 12/1999 |
| JP | 11-352686 | A | 12/1999 |
| JP | 2000-19729 | A | 1/2000 |
| JP | 2000-19738 | A | 1/2000 |
| JP | 3279035 | B2 | 4/2002 |
| JP | 2002-236360 | A | 8/2002 |
| JP | 3324279 | B2 | 9/2002 |
| WO | 2006/038823 | A | 4/2006 |

* cited by examiner

*Primary Examiner* — John A. McPherson
(74) *Attorney, Agent, or Firm* — SOLARIS Intellectual Property Group, PLLC

(57) ABSTRACT

A colored curable composition is provided which has good developability, has excellent color purity, can be formed into a thin film, and has a high absorption coefficient. The colored curable composition includes at least one of specific dipyrromethene metal complex compounds and tautomers thereof. Also, a colored curable composition suitable for forming a color filter which is used in a liquid crystal display device or a solid-state imaging device, and a color filter using the colored curable composition and a method of producing the same are provided.

9 Claims, No Drawings

COLORED CURABLE COMPOSITION, COLOR FILTER AND METHOD OF PRODUCING THE SAME, AND DIPYRROMETHENE METAL COMPLEX COMPOUND AND TAUTOMER THEREOF

CROSS-REFERENCE TO RELATED APPLICATION

This application is a divisional of U.S. Ser. No. 12/550,427, filed Aug. 31, 2009, which claims priority under 35 USC 119 from Japanese Patent Application Nos. 2008-225108 filed on Sep. 2, 2008 and 2008-251337 filed on Sep. 29, 2008, the disclosures of which are incorporated by reference herein.

BACKGROUND OF THE INVENTION

1. Field of the Invention

The present invention relates to a dipyrromethene metal complex compound and a tautomer thereof, a colored curable composition suitable for forming a color filter which is used in a liquid crystal display device or a solid-state imaging device, and a color filter using the colored curable composition and a method of producing the same.

2. Description of the Related Art

One method of producing a color filter used in a liquid crystal display device or a solid-state imaging device is a pigment dispersion method. There is a method of producing a color filter by photolithography using a colored radiation-sensitive composition obtained by dispersing a pigment in a variety of photosensitive compositions by the pigment dispersion method. Since a pigment is used in this method, the resultant composition is stable with respect to light and heat, and since patterning is performed by photolithography, sufficient positional precision can be ensured. Thus, this method has been widely utilized as a method suitable for producing a color filter for a large screen and a high-definition color display.

In preparing a color filter by the pigment dispersion method, the radiation-sensitive composition is first applied onto a substrate with a spin coater or roll coater and dried to form a coating film. Then, colored pixels are obtained by pattern exposure and development of the coating film. The color filter can be prepared by repeating this operation a number of times corresponding to the number of hues.

Recently, even higher resolution has become desirable in color filters for solid-state imaging devices; however, it is difficult to further improve the resolution with conventional pigment dispersions. Problems such as the generation of color irregularities due to coarse particles of the pigment result in a lack of suitability for uses which require fine patterns such as solid state image sensing devices.

Use of a dye as the colorant has been conventionally studied from the viewpoint of improvement in resolution above (see, for example, Japanese Patent Application Laid-Open (JP-A) No. 6-75375). However, such dye-containing curing compositions have the following additional problems:

(1) Dyes generally have lower light stability and/or lower heat resistance than pigments.

(2) It is difficult to obtain a liquid curable composition having a desired spectrum with a common colorant, because such a colorant is less soluble in an aqueous alkaline solution or organic solvent (hereinafter, also simply referred to as a "solvent").

(3) It is difficult to control the solubility (developing efficiency) of the cured area and the uncured area, because the dye used often interacts with other components in the curable composition.

(4) When the molar absorption coefficient ($\epsilon$) of the dye used is low, a large amount of the dye should be added, and thus the amounts of the other components in the curable composition, such as polymerizable compound (monomer), binder, and photopolymerization initiator must be reduced, which leads to deterioration in the curing efficiency of the composition, the heat resistance after curing, and the developing efficiency of the cured area or uncured area.

Due to these problems, it has been difficult to form a thin film of fine colored patterns for high-definition color filters. Unlike those used in the production of semiconductors, it is necessary to use a thin film having a thickness of 1 μm or less for the production of color filters for solid-state imaging devices. It is thus necessary to add a larger amount of a colorant to the curable composition in order to obtain a desired absorption, leading to the problems described above.

Next, the conventional art with respect to a high fastness dye will be described. Generally, coloring agents which are used in a variety of applications are commonly required to have the following properties. That is, the coloring agents are required to have absorption properties which are preferable in terms of color reproducibility, fastness in use environment conditions (for example, good heat resistance, good light resistance and good humidity resistance), and large molar absorption coefficients, and are required to be easily formed into a thin film.

For example, a dipyrromethene metal complex is known to be used as a functional compound in a variety of applications, and is used as a sensitizer for a radical polymerization initiator in a visible photopolymerization composition (see, for example, Japanese Patent Nos. 3279035 and 3324279, and JP-A Nos. 11-352685, 11-352686, 2000-19729, 2000-19738, and 2002-236360). In addition, the dipyrromethene metal complex is known to have a high molar absorption coefficient, and have absorption properties which are preferable in terms of color reproducibility (see, for example, US Patent Application Publication No. 2008/0076044 A1).

On the other hand, particularly in a color filter of a solid-state imaging device, fine pattern forming properties are required, and it is difficult to regulate solubility (developability) of a cured area and a uncured area. Specifically, a fine pattern is formed by light exposure through a mask having a fine pattern, and subsequent development with an alkaline liquid to dissolve an unexposed area in an alkali developer. However, when the solubility of a colored curable composition in an alkali developer is poor, pattern forming properties are deteriorated (i.e., a colored material remains at an unexposed area). Accordingly, a colored curable composition having low dependency on the concentration of the alkali liquid is sought.

SUMMARY OF THE INVENTION

According to a first aspect of the present invention, a colored curable composition is provided which has good developability, has excellent color purity, can be formed into a thin film, and has a high absorption coefficient.

Further, a color filter which is thin, has excellent color concentration and color purity, and has excellent fastness, and a method of producing the same are provided.

Still further, a dipyrromethene metal complex compound which has high solvent solubility and fastness, has excellent absorption property, and has a high molar absorption coefficient, and a tautomer thereof, are also provided.

According to a second aspect of the invention, a magenta to violet colored curable composition (i.e., a curable composition having any one color from magenta to violet) is provided which is useful for a primary-colored color filter having blue, green and red colors, has excellent color purity, can be formed into a thin film, has a high absorption coefficient, and has excellent pattern forming property.

Further, a magenta to violet color filter (i.e., a color filter having any one color from magenta to violet) using the colored curable composition, which has excellent color purity, can be formed into a thin film, and has excellent fastness, and a method producing the same are provided.

Still further, a colorant (i.e., a dipyrromethene metal complex) which is useful in the colored curable composition useful for a color filter, has excellent absorption property, has a high molar absorption coefficient, and may impart favorable developability is also provided.

As the result of detailed study of various colorants, the inventors of the present invention have found that a dipyrromethene metal complex compound having a specified substituent has a good hue, a high absorption coefficient, excellent fastness, excellent solubility in an organic solvent and excellent pattern forming properties (i.e., low dependency on the concentration of an alkali developer), and completed the invention based on these findings.

Aspects of the invention will be described below.

<1> A colored curable composition, including at least one selected from the group consisting of a compound represented by the following Formula (A1) and a tautomer thereof and a compound represented by the following Formula (B1) and a tautomer thereof:

Formula (A1)

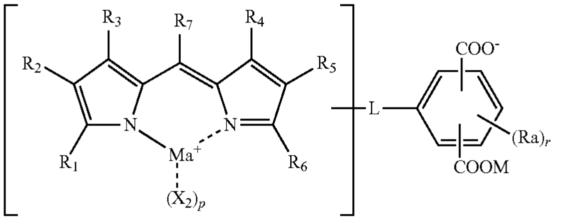

Formula (B1)

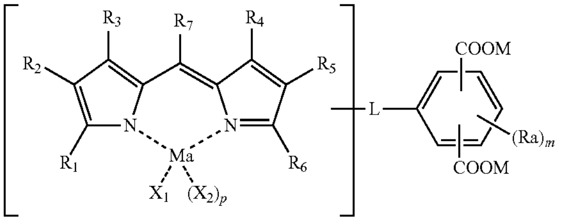

wherein, in Formula (A1) or Formula (B1), Ra represents a substituent; m represents an integer of 0, 1, 2, or 3; when there is more than one Ra, each Ra may be the same as or different from another Ra; M represents a hydrogen atom or an organic base or metal atom necessary for neutralizing a charge; L represents a single bond, an alkylene group, —O—, —N(Rb)—, —S—, —SO—, or —$SO_2$—, where Rb represents a hydrogen atom, an alkyl group, an aryl group, a heterocyclic group, an acyl group, a carbamoyl group, an alkoxycarbonyl group, an alkylsulfonyl group, or an arylsulfonyl group; $R_1$ to $R_6$ each independently represent a hydrogen atom or a substituent; $R_7$ represents a hydrogen atom, a halogen atom, an alkyl group, an aryl group, or a heterocyclic group; at least one of $R_1$ to $R_6$ represents a substituent and any one of the substituents represented by $R_1$ to $R_6$ is a divalent linking group that binds to -L-; Ma represents a metal or a metal compound which may form a complex; $X_1$ represents a group necessary for neutralizing a charge of Ma; $X_2$ represents a group which may bind to Ma; p represents 0 or 1; and $X_1$ and $X_2$ may bind together to form a 5-membered, 6-membered or 7-membered ring.

<2> The colored curable composition according to <1>, wherein the compound represented by Formula (A1) is a compound represented by the following Formula (1-A1), and the compound represented by Formula (B1) is a compound represented by the following Formula (1-B1):

Formula (1-A1)

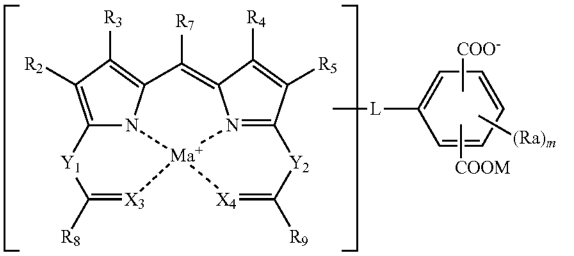

Formula (1-B1)

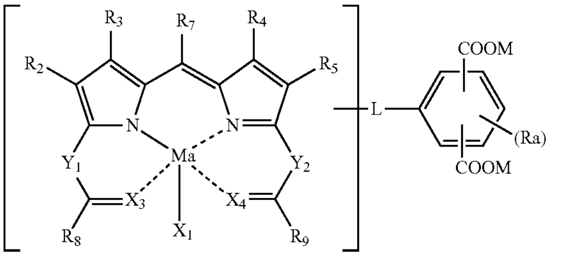

wherein, in Formula (1-A1) or Formula (1-B1), Ra represents a substituent; m represents an integer of 0, 1, 2 or 3; when there is more than one Ra, each Ra may be the same as or different from another Ra; M represents a hydrogen atom, or an organic base or metal atom necessary for neutralizing a charge; L represents a single bond, an alkylene group, —O—, —N(Rb)—, —S—, —SO—, or —$SO_2$—, where Rb represents a hydrogen atom, an alkyl group, an aryl group, a heterocyclic group, an acyl group, a carbamoyl group, an alkoxycarbonyl group, an alkylsulfonyl group, or an arylsulfonyl group; $R_2$ to $R_5$ each independently represent a hydrogen atom or a substituent; $R_7$ represents a hydrogen atom, a halogen atom, an alkyl group, an aryl group, or a heterocyclic group; $R_8$ and $R_9$ each independently represent an alkyl group, an alkenyl group, an aryl group, a heterocyclic group, an alkoxy group, an aryloxy group, an amino group, an anilino group, or a heterocyclic amino group; at least one of $R_2$ to $R_5$, $R_8$ and $R_9$ represents a substituent and any one of the substituents represented by $R_2$ to $R_5$, $R_8$ and $R_9$ is a divalent linking group that binds to -L-; Ma represents a metal or a metal compound; $X_1$ represents a group necessary for neutralizing a charge of Ma; $X_3$ and $X_4$ each independently represent NR, a nitrogen atom, an oxygen atom, or a sulfur atom, where R represents a hydrogen atom, an alkyl group, an alkenyl group, an aryl group, a heterocyclic group, an acyl group, an alkylsulfonyl group, or an arylsulfonyl group; $Y_1$ and $Y_2$ each independently represent NR or an oxygen atom, and R represents a hydrogen atom, an alkyl group, an alkenyl group, an aryl group, a heterocyclic group, an acyl group, an alkylsulfonyl group, or an arylsulfonyl group; $R_8$ and $Y_1$ may bind together to form a 5-membered, 6-membered or 7-membered ring; and $R_9$ and $Y_2$ may bind together to form a 5-membered, 6-membered, or 7-membered ring.

<3> The colored curable composition according to <1>, wherein the compound represented by Formula (A-1) is a compound represented by the following Formula (2-A1), and the compound represented by Formula (B-1) is a compound represented by the following Formula (2-B1):

Formula (2-A1)

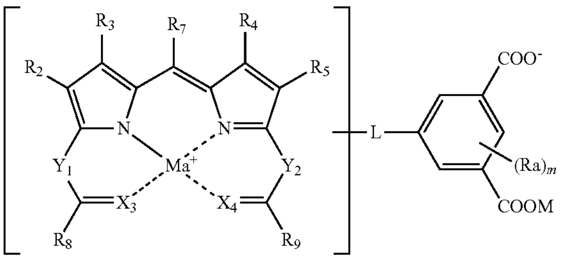

Formula (2-B1)

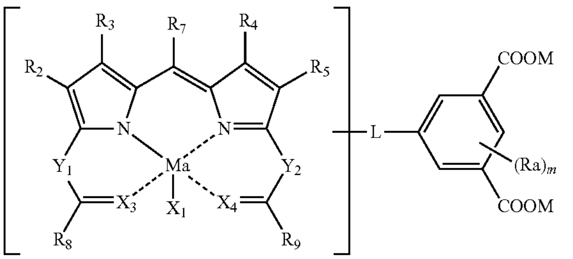

wherein, Ra represents a substituent; m represents an integer of 0, 1, 2 or 3; when there is more than one Ra, each Ra may be the same as or different from another Ra; M represents a hydrogen atom, or an organic base or metal atom necessary for neutralizing a charge; L represents a single bond, an alkylene group, —O—, —N(Rb)—, —S—, —SO—, or —$SO_2$—, where Rb represents a hydrogen atom, an alkyl group, an aryl group, a heterocyclic group, an acyl group, a carbamoyl group, an alkoxycarbonyl group, an alkylsulfonyl group, or an arylsulfonyl group; $R_2$ to $R_5$ each independently represent a hydrogen atom or a substituent; $R_7$ represents a hydrogen atom, a halogen atom, an alkyl group, an aryl group, or a heterocyclic group; $R_8$ and $R_9$ each independently represent an alkyl group, an alkenyl group, an aryl group, a heterocyclic group, an alkoxy group, an aryloxy group, an amino group, an anilino group, or a heterocyclic amino group; at least one of $R_2$ to $R_5$, $R_8$ and $R_9$ represents a substituent and any one of the substituents represented by $R_2$ to $R_5$, $R_8$ and $R_9$ is a divalent linking group that binds to -L-; Ma represents a metal or a metal compound; $X_1$ represents a group necessary for neutralizing a charge of Ma; $X_3$ and $X_4$ each independently represent NR, a nitrogen atom, an oxygen atom, or a sulfur atom, where R represents a hydrogen atom, an alkyl group, an alkenyl group, an aryl group, a heterocyclic group, an acyl group, an alkylsulfonyl group, or an arylsulfonyl group; $Y_1$ and $Y_2$ each independently represent NR or an oxygen atom, where R represents a hydrogen atom, an alkyl group, an alkenyl group, an aryl group, a heterocyclic group, an acyl group, an alkylsulfonyl group, or an arylsulfonyl group; $R_8$ and $Y_1$ may bind together to form a 5-membered, 6-membered or 7-membered ring; and $R_9$ and $Y_2$ may bind together to form a 5-membered, 6-membered, or 7-membered ring.

<4> The colored curable composition according to <1>, wherein Ma shown in Formula (A1) or Formula (B1) represents Fe, Zn, Co, V═O, or Cu.

<5> The colored curable composition according to <2>, wherein Ma shown in Formula (1-A1) or Formula (1-B1) represents Fe, Zn, Co, V═O, or Cu.

<6> The colored curable composition according to <3>, wherein Ma shown in Formula (2-A1) or Formula (2-B1) represents Fe, Zn, Co, V═O, or Cu.

<7> The colored curable composition according to <4>, wherein Ma represents Zn.

<8> A color filter, including the colored curable composition according to <1>.

<9> A method of producing a color filter, including:

applying the colored curable composition according to <1> onto a support to form a coated film; and exposing the coated film to light and developing the exposed coated film, to form a pattern image.

<10> A compound represented by the following Formula (2-A1) or (2-B1), or a tautomer thereof:

Formula (2-A1)

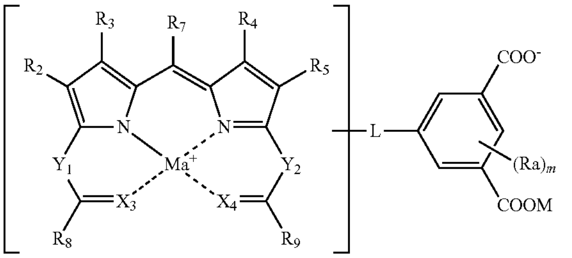

Formula (2-B1)

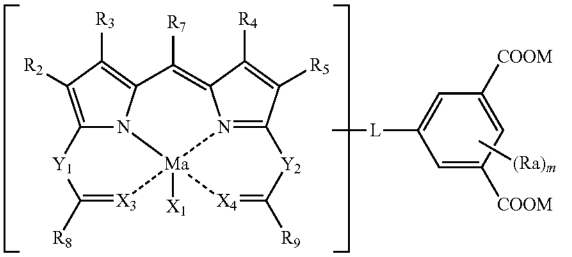

wherein, in Formula (2-A1) or Formula (2-B1), Ra represents a substituent; m represents an integer of 0, 1, 2 or 3; when there is more than one Ra, each Ra may be the same as or different from another Ra; M represents a hydrogen atom, or an organic base or metal atom necessary for neutralizing a charge; L represents a single bond, an alkylene group, —O—, —N(Rb)—, —S—, —SO—, or —$SO_2$—, where Rb represents a hydrogen atom, an alkyl group, an aryl group, a heterocyclic group, an acyl group, a carbamoyl group, an alkoxycarbonyl group, an alkylsulfonyl group, or an arylsulfonyl group; $R_2$ to $R_5$ each independently represent a hydrogen atom or a substituent; $R_7$ represents a hydrogen atom, a halogen atom, an alkyl group, an aryl group, or a heterocyclic group; $R_8$ and $R_9$ each independently represent an alkyl group, an alkenyl group, an aryl group, a heterocyclic group, an alkoxy group, an aryloxy group, an amino group, an anilino group, or a heterocyclic amino group; at least one of $R_2$ to $R_5$, $R_8$ and $R_9$ represents a substituent and any one of the substituents represented by $R_2$ to $R_5$, $R_8$ and $R_9$ is a divalent linking group that binds to -L-; Ma represents a metal or a metal compound; $X_1$ represents a group necessary for neutralizing a charge of Ma; $X_3$ and $X_4$ each independently represent NR, a nitrogen atom, an oxygen atom, or a sulfur atom, where R represents a hydrogen atom, an alkyl group, an alkenyl group, an aryl group, a heterocyclic group, an acyl group, an alkylsulfonyl group, or an arylsulfonyl group; $Y_1$ and $Y_2$ each independently represent NR or an oxygen atom, where R represents a hydrogen atom, an alkyl group, an alkenyl group, an aryl group, a heterocyclic group, an acyl group, an alkylsulfonyl group, or an arylsulfonyl group; $R_8$ and $Y_1$ may bind together to form a 5-membered, 6-membered or 7-membered ring; and $R_9$ and $Y_2$ may bind together to form a 5-membered, 6-membered, or 7-membered ring.

<11> A compound represented by the following Formula (C1) or (D1), or a tautomer thereof:

Formula (C1)

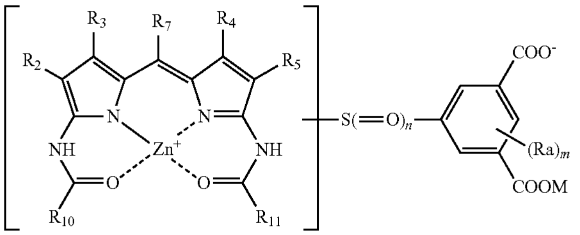

Formula (D1)

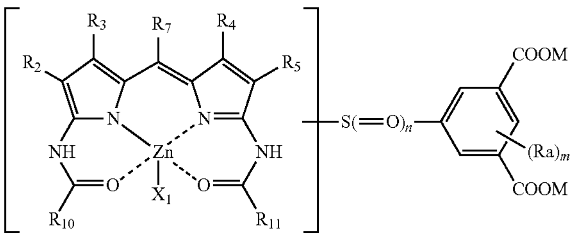

wherein, in Formula (C1) or Formula (D1), Ra represents a substituent; m represents an integer of 0, 1, 2 or 3; when there is more than one Ra, each Ra may be the same as or different from another Ra; n represents 0 or 2; M represents a hydrogen atom, or an organic base or metal atom necessary for neutralizing a charge; $R_2$ to $R_5$ each independently represent a hydrogen atom or a substituent; $R_7$ represents a hydrogen atom, a halogen atom, an alkyl group, an aryl group, or a heterocyclic group; $R_{10}$ and $R_{11}$ each independently represent an alkyl group, an alkenyl group, an aryl group, or a heterocyclic group; at least one of $R_2$ to $R_5$, $R_{10}$ and $R_{11}$ represents a substituent and any one of the substituents represented by $R_2$ to $R_5$, $R_{10}$ and $R_{11}$ is a divalent linking group that binds to —S(═O)n-; and $X_1$ represents a group that can bind to Zn.

<12> A colored curable composition, including at least one selected from the group consisting of a compound represented by the following Formula (A2) and a tautomer thereof and a compound represented by the following Formula (B2) and a tautomer thereof:

Formula (A2)

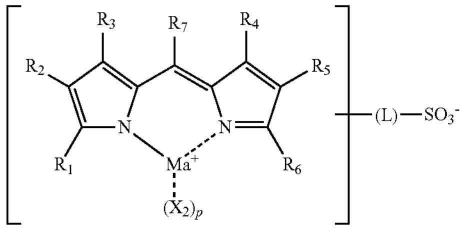

Formula (B2)

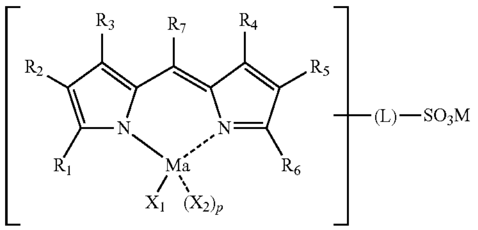

wherein, in Formula (A2) or Formula (B2), $R_1$ to $R_6$ each independently represent a hydrogen atom or a substituent; $R_7$ represents a hydrogen atom, a halogen atom, an alkyl group, an aryl group, or a heterocyclic group; at least one of $R_1$ to $R_6$ represents a substituent and any one of the substituents represented by $R_1$ to $R_6$ is a divalent linking group that binds to -(L)-$SO_3^-$ or -(L)-$SO_3M$; M represents a hydrogen atom, or an organic base or metal atom necessary for neutralizing a charge; L represents an alkylene group, an aralkylene group, or an arylene group, or a divalent group which may be formed by a combination of divalent groups selected from the group consisting of an alkylene group, an aralkylene group, an arylene group, —O—, —S—, —$SO_2$—, —N(Ra)—, —COO—, —OCO—, —CON(Rb)—, —N(Rb)CO—, —N(Rb)COO—, —OOCN(Rb)—, —N(Rb)CON(Rc)—, —$SO_2$N(Rb)—, and —N(Rb)$SO_2$—, where Ra represents an alkyl group, an alkenyl group, an aryl group, a heterocyclic group, an acyl group, an alkylsulfonyl group, or an arylsulfonyl group and Rb and Rc each independently represent a hydrogen atom, an alkyl group, an alkenyl group, an aryl group, or a heterocyclic group; Ma represents a metal or a metal compound which may form a complex; $X_1$ represents a group necessary for neutralizing a charge of Ma; $X_2$ represents a group which may bind to Ma; p represents 0 or 1; and, in Formula (B2), $X_1$ and $X_2$ may bind together to form a 5-membered, 6-membered, or 7-membered ring.

<13> The colored curable composition according to <12>, wherein the compound represented by Formula (A2) is a compound represented by the following Formula (1-A2), and the compound represented by Formula (B2) is a compound represented by the following Formula (1-B2):

Formula (1-A2)

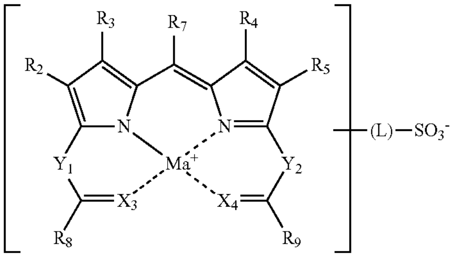

-continued

Formula (1-B2)

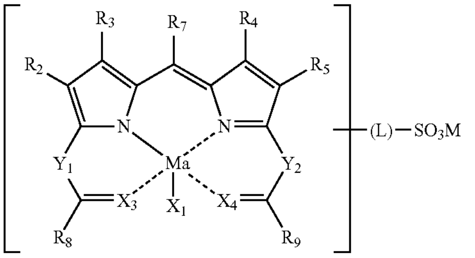

wherein, in Formula (1-A2) or Formula (1-B2), $R_2$ to $R_5$ each independently represent a hydrogen atom or a substituent; $R_7$ represents a hydrogen atom, a halogen atom, an alkyl group, an aryl group, or a heterocyclic group; $R_8$ and $R_9$ each independently represent an alkyl group, an alkenyl group, an aryl group, a heterocyclic group, an alkoxy group, an aryloxy group, an amino group, an anilino group or a heterocyclic amino group; at least one of $R_2$ to $R_5$, $R_8$ and $R_9$ represents a substituent and any one of the substituents represented by $R_2$ to $R_5$, $R_8$ and $R_9$ is a divalent linking group to bind to -(L)-$SO_3^-$ or -(L)-$SO_3M$; M represents a hydrogen atom, or an organic base or metal atom necessary for neutralizing a charge; L represents an alkylene group, an aralkylene group, or an arylene group, or a divalent group which may be formed by a combination of divalent groups selected from the group consisting of an alkylene group, an aralkylene group, an arylene group, —O—, —S—, —$SO_2$—, —N(Ra)—, —COO—, —OCO—, —CON(Rb)—, —N(Rb)CO—, —N(Rb)COO—, —OOCN(Rb)—, —N(Rb)CON(Rc)—, —$SO_2$N(Rb)—, and —N(Rb)$SO_2$—, where Ra represents an alkyl group, an alkenyl group, an aryl group, a heterocyclic group, an acyl group, an alkylsulfonyl group, or an arylsulfonyl group and Rb and Rc each independently represent a hydrogen atom, an alkyl group, an alkenyl group, an aryl group, or a heterocyclic group; Ma represents a metal or metal compound which may form a complex; $X_1$ represents a group necessary for neutralizing a charge of Ma; $X_3$ and $X_4$ each independently represent NR, an oxygen atom, or a sulfur atom, where R represents a hydrogen atom, an alkyl group, an alkenyl group, an aryl group, a heterocyclic group, an acyl group, an alkylsulfonyl group, or an arylsulfonyl group; R and $R_8$ or $R_9$ may bind together to form a 5-membered, 6-membered, or 7-membered ring; $Y_1$ and $Y_2$ each independently represent NR or an oxygen atom, where R represents a hydrogen atom, an alkyl group, an alkenyl group, an aryl group, a heterocyclic group, an acyl group, an alkylsulfonyl group, or an arylsulfonyl group; $R_8$ and $Y_1$ may bind together to form a 5-membered, 6-membered, or 7-membered ring; and $R_9$ and $Y_2$ may bind together to form a 5-membered, 6-membered, or 7-membered ring.

<14> The colored curable composition according to <12>, wherein Ma represents Fe, Zn, Co, V═O, or Cu.

<15> The colored curable composition according to <12>, wherein Ma represents Zn.

<16> A colored curable composition, including at least one selected from the group consisting of a compound represented by the following Formula (C2) and a tautomer thereof and a compound represented by the following Formula (D2) and a tautomer thereof:

Formula (C2)

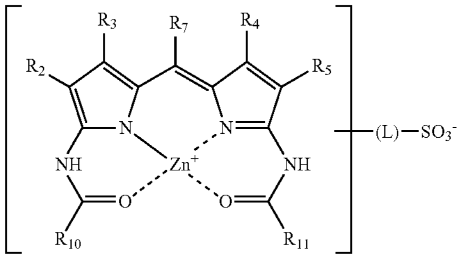

Formula (D2)

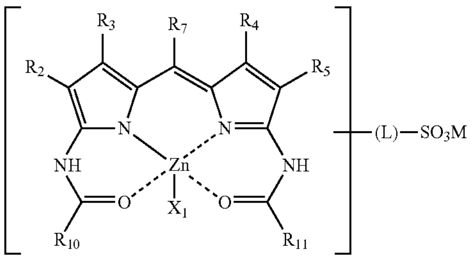

wherein, in Formula (C2) or Formula (D2), $R_2$ to $R_5$ each independently represent a hydrogen atom or a substituent; $R_7$ represents a hydrogen atom, a halogen atom, an alkyl group, an aryl group, or a heterocyclic group; $R_{10}$ and $R_{11}$ each independently represent an alkyl group, an alkenyl group, an aryl group, a heterocyclic group, an alkoxy group, an aryloxy group, an amino group, an anilino group, or a heterocyclic amino group; at least one of $R_2$ to $R_5$, $R_{10}$ and $R_{11}$ represents a substituent and any one of the substituents represented by $R_2$ to $R_5$, $R_{10}$ and $R_{11}$ is a divalent linking group that binds to -(L)-$SO_3^-$ or -(L)-$SO_3M$; M represents a hydrogen atom, or an organic base or metal atom necessary for neutralizing a charge; L represents an alkylene group, an aralkylene group, or an arylene group, or a divalent group which may be formed by a combination of divalent groups selected from the group consisting of an alkylene group, an aralkylene group, an arylene group, —O—, —S—, —$SO_2$—, —N(Ra)—, —COO—, —OCO—, —CON(Rb)—, —N(Rb)CO—, —N(Rb)COO—, —OOCN(Rb)—, —N(Rb)CON(Rc)—, —$SO_2$N(Rb)—, and —N(Rb)$SO_2$—, where Ra represents an alkyl group, an alkenyl group, an aryl group, a heterocyclic group, an acyl group, an alkylsulfonyl group, or an arylsulfonyl group and Rb and Rc each independently represent a hydrogen atom, an alkyl group, an alkenyl group, an aryl group, or a heterocyclic group; and $X_1$ represents a group necessary for neutralizing a charge of Zn.

<17> A color filter including the colored curable composition according to <12>.

<18> A method of producing a color filter, including:

applying the colored curable composition according to <12> onto a support to form a coated film;

exposing the coated film to light through a mask, and developing the coated film to form a pattern image.

<19> A colorant, selected from the group consisting of a compound represented by Formula (C2) and a tautomer thereof and a compound represented by Formula (D2) and a tautomer thereof:

Formula (C2)

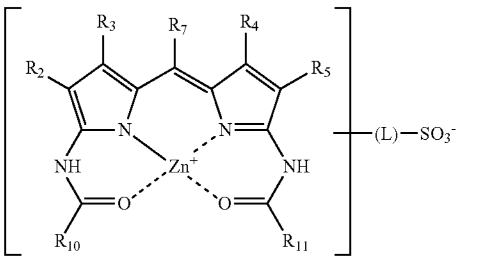

Formula (D2)

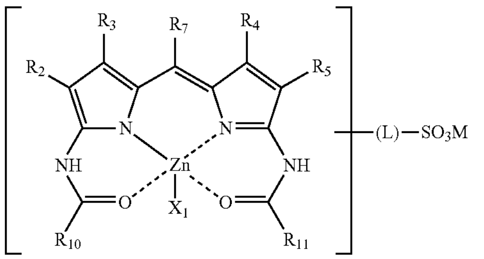

wherein, in Formula (C2) or Formula (D2), $R_2$ to $R_5$ each independently represent a hydrogen atom or a substituent; $R_7$ represents a hydrogen atom, a halogen atom, an alkyl group, an aryl group, or a heterocyclic group; $R_{10}$ and $R_{11}$ each independently represent an alkyl group, an alkenyl group, an aryl group, a heterocyclic group, an alkoxy group, an aryloxy group, an amino group, an anilino group, or a heterocyclic amino group; at least one of $R_2$ to $R_5$, $R_{10}$ and $R_{11}$ represents a substituent and any one of the substituents represented by $R_2$ to $R_5$, $R_{10}$ and $R_{11}$ is a divalent linking group that binds to $-(L)-SO_3^-$ or $-(L)-SO_3M$; M represents a hydrogen atom, or an organic base or metal atom necessary for neutralizing a charge; L represents an alkylene group, an aralkylene group, or an arylene group, or a divalent group which may be formed by a combination of divalent groups selected from the group consisting of an alkylene group, an aralkylene group, an arylene group, —O—, —S—, $—SO_2—$, —N(Ra)—, —COO—, —OCO—, —CON(Rb)—, —N(Rb)CO—, —N(Rb)COO—, —OOCN(Rb)—, —N(Rb)CON(Rc)—, $—SO_2N(Rb)—$, and $—N(Rb)SO_2—$, where Ra represents an alkyl group, an alkenyl group, an aryl group, a heterocyclic group, an acyl group, an alkylsulfonyl group, or an arylsulfonyl group and Rb and Rc each independently represent a hydrogen atom, an alkyl group, an alkenyl group, an aryl group, or a heterocyclic group; and $X_1$ represents a group necessary for neutralizing a charge of Zn.

According to the first aspect of the present invention, a colored curable composition is provided which has good developability, has excellent color purity, can be formed into a thin film, and has a high absorption coefficient.

Further, according to the first aspect of the invention, a color filter which is thin, has excellent color concentration and color purity, and, has excellent fastness, and a method of producing the same are provided.

Still further, according to the first aspect of the invention, a dipyrromethene metal complex compound which has high solvent solubility and fastness, has excellent absorption property, and has a high molar absorption coefficient, and a tautomer thereof are also provided.

According to the second aspect of the invention, a colored curable composition including a dipyrromethene metal complex having a specified substituent is provided, which is useful in a primary-colored color filter having blue, green and red colors, has excellent color purity, can be formed in to a thin film, has a high absorption coefficient, has excellent fastness, has low solubility in an organic solvent, and dependency on a concentration of an alkali developer, and excellent in pattern forming property.

Further, according to the second aspect of the invention, a color filter which has excellent color purity, can be formed into a thin film, has excellent fastness, and has high resolution, and a method of producing the same are provided.

Still further, according to the second aspect of the invention, a colorant (i.e., a dipyrromethene metal complex) which is useful in a colored curable composition useful for a color filter, has excellent absorption property, has a high molar absorption coefficient, and may impart suitable developability is provided.

DETAILED DESCRIPTION OF THE INVENTION

Hereinbelow, the colored curable composition, the color filter, and the process for producing the color filter of the present invention will be described in detail.

Colored Curable Composition

Colored Curable Composition of First Exemplary Embodiment

The colored curable composition according to a first exemplary embodiment of the invention includes, as a coloring agent, at least one selected from a dipyrromethene metal complex compound having a specified substituent represented by the following Formula (A1) and a dipyrromethene metal complex compound having a specified substituent represented by the following Formula (B1), and tautomers thereof.

It is preferable that the colored curable composition according to the first exemplary embodiment of the invention is an ultraviolet-sensitive colored curable composition.

Compounds Represented by Formula (A1) and Formula (B1), and Tautomers Thereof Formula (A1)

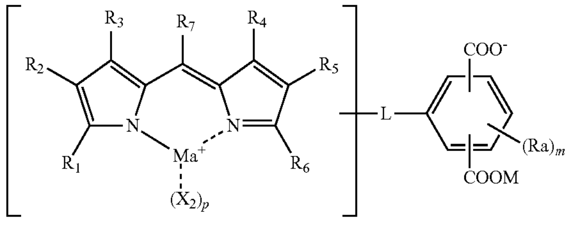

Tautomers of Formula (A1)

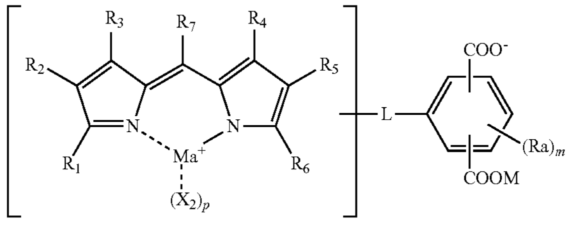

-continued

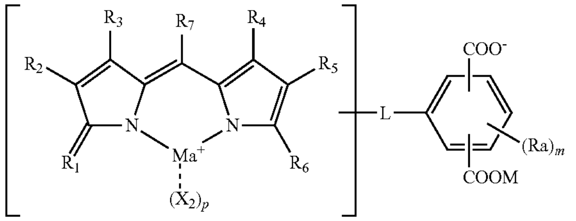

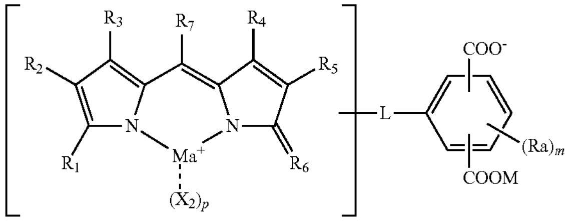

Formula (B1)

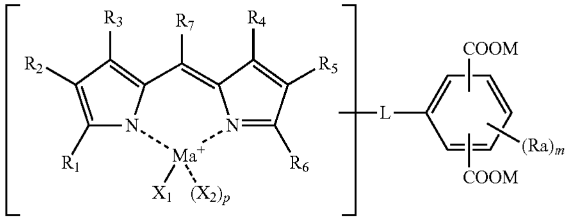

Tautomers of Formula (B1)

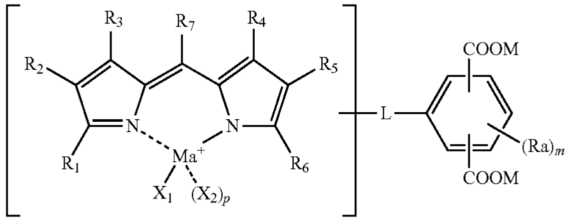

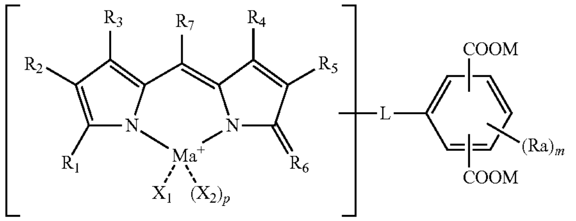

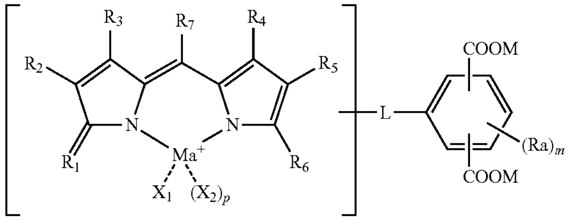

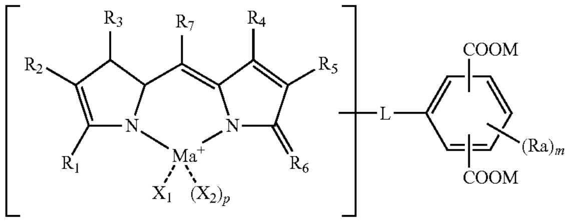

-continued

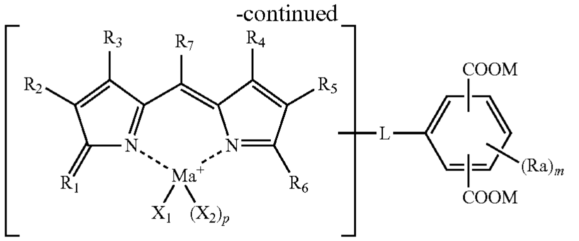

In Formula (A1) and Formula (B1), Ra represents a substituent, m represents an integer of 0, 1, 2, or 3, and M represents a hydrogen atom or an organic base or metal atom necessary for neutralizing a charge.

L represents a single bond, an alkylene group, —O—, —N(Rb)—, —S—, —SO—, or —$SO_2$—, and Rb represents a hydrogen atom, an alkyl group, an aryl group, a heterocyclic group, an acyl group, a carbamoyl group, an alkoxycarbonyl group, an alkylsulfonyl group, or an arylsulfonyl group.

$R_1$ to $R_6$ each independently represent a hydrogen atom or a substituent, and $R_7$ represents a hydrogen atom, a halogen atom, an alkyl group, an aryl group, or a heterocyclic group, provided that any one of the substituents represented by $R_1$ to $R_6$ is a divalent linking group that binds to -L-.

Ma represents a metal or a metal compound which may form a complex.

$X_1$ represents a group necessary for neutralizing a charge of Ma; $X_2$ represents a group which may bind to Ma; p represents 0 or 1; and $X_1$ and $X_2$ may bind together to form a 5-membered, 6-membered or 7-membered ring.

Formula (A1) and Formula (B1) will be described in detail.

Ra in Formula (A1) or Formula (B1) represents a substituent. Examples of the substituent represented by Ra include a halogen atom (for example, fluorine, chlorine, bromine), an alkyl group (for example, a straight, branched or cyclic alkyl group having preferably 1 to 48 carbon atoms, more preferably 1 to 24 carbon atoms; examples thereof include a methyl group, an ethyl group, a propyl group, an isopropyl group, a butyl group, a t-butyl group, a pentyl group, a hexyl group, a heptyl group, an octyl group, a 2-ethylhexyl group, a dodecyl group, a hexadecyl group, a cyclopropyl group, a cyclopentyl group, a cyclohexyl group, a 1-norbornyl group, and a 1-adamantyl group), an alkenyl group (for example, an alkenyl group having preferably 2 to 48 carbon atoms, more preferably 2 to 18 carbon atoms; examples thereof include a vinyl group, an allyl group, and a 3-buten-1-yl group), an aryl group (for example, an aryl group having preferably 6 to 48 carbon atoms, more preferably 6 to 24 carbon atoms; examples thereof include a phenyl group and a naphthyl group), a heterocyclic group (for example, a heterocyclic group having preferably 1 to 32 carbon atoms, more preferably 1 to 18 carbon atoms; examples thereof include a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group, and a benzotriazol-1-yl group), a silyl group (for example, a silyl group having preferably 3 to 38 carbon atoms, more preferably 3 to 18 carbon atoms; examples thereof include a trimethylsilyl group, a triethylsilyl group, a tributylsilyl group, a t-butyldimethylsilyl group, and a t-hexyldimethylsilyl group), a hydroxyl group, a cyano group, a nitro group, an alkoxy group (for example, an alkoxy group having preferably 1 to 48 carbon atoms, more preferably 1 to 24 carbon atoms; examples thereof include a methoxy group, an ethoxy group, a 1-butoxy group, a 2-butoxy group, an isopropoxy group, a t-butoxy group, a dodecyloxy group, and a cycloalkyloxy group such as a cyclopentyloxy group or a cyclohexyloxy group), an aryloxy group (for example, an aryloxy group having preferably 6 to 48 carbon atoms, more preferably 6 to 24 carbon atoms; examples thereof include a phenoxy group and a 1-naphthoxy group), a heterocyclic oxy group (for example, a heterocyclic oxy group having preferably 1 to 32 carbon atoms, more preferably 1 to 18 carbon atoms; examples thereof include a 1-phenyltetrazol-5-oxy group and a 2-tetrahydropyranyloxy group), a silyloxy group (for example, a silyloxy group having preferably 1 to 32 carbon atoms, more preferably 1 to 18 carbon atoms; examples thereof include a trimethylsilyloxy group, a t-butyldimethylsiliyloxy group, and a diphenylmethylsilyloxy group), an acyloxy group (for example, an acyloxy group having preferably 2 to 48 carbon atoms, more preferably 2 to 24 carbon atoms; examples thereof include an acetoxy group, a pivaloyloxy group, a benzoyloxy group, and a dodecanoyloxy group), an alkoxycarbonyloxy group (for example, an alkoxycarbonyloxy group having preferably 2 to 48 carbon atoms, more preferably 2 to 24 carbon atoms; examples thereof include an ethoxycarbonyloxy group, a t-butoxycarbonyloxy group, and a cycloalkyloxycarbonyloxy group such as a cyclohexyloxycarbonyloxy group), an aryloxycarbonyloxy group (for example, an aryloxycarbonyloxy group having preferably 7 to 32 carbon atoms, more preferably 7 to 24 carbon atoms; examples thereof include a phenoxycarbonyloxy group), a carbamoyloxy group (for example, a carbamoyloxy group having preferably 1 to 48 carbon atoms, more preferably 1 to 24 carbon atoms; examples thereof include a N,N-dimethylcarbamoyloxy group, a N-butylcarbamoyloxy group, N-phenylcarbamoyloxy group, and a N-ethyl-N-phenylcarbamoyloxy group), a sulfamoyloxy group (for example, a sulfamoyloxy group having preferably 1 to 32 carbon atoms, more preferably 1 to 24 carbon atoms; examples thereof include a N,N-diethylsulfamoyloxy group and a N-propylsulfamoyloxy group), an alkylsulfonyloxy group (for example, an alkylsulfonyloxy group having preferably 1 to 38 carbon atoms, more preferably 1 to 24 carbon atoms; examples thereof include a methylsulfonyloxy group, a hexadecylsulfonyloxy group, and a cyclohexylsulfonyloxy group), an arylsulfonyloxy group (for example, an arylsulfonyloxy group having preferably 6 to 32 carbon atoms, more preferably 6 to 24 carbon atoms; examples thereof include a phenylsulfonyloxy group), an acyl group (for example, an acyl group having preferably 1 to 48 carbon atoms, more preferably 1 to 24 carbon atoms; examples thereof include a formyl group, an acetyl group, a pivaloyl group, a benzoyl group, a tetradecanoyl group, and a cyclohexanoyl group), an alkoxycarbonyl group (for example, an alkoxycarbonyl group having preferably 2 to 48 carbon atoms, more preferably 2 to 24 carbon atoms; examples thereof include a methoxycarbonyl group, an ethoxycarbonyl group, an octadecyloxycarbonyl group, a cyclohexyloxycarbonyl group, and a 2,6-di-tert-butyl-4-methylcyclohexyloxycarbonyl group), an aryloxycarbonyl group (for example, an aryloxycarbonyl group having preferably 7 to 32 carbon atoms, more preferably 7 to 24 carbon atoms; examples thereof include a phenoxycarbonyl group), a carbamoyl group (for example, a carbamoyl group having preferably 1 to 48 carbon atoms, more preferably 1 to 24 carbon atoms; examples thereof include a carbamoyl group, a N,N-diethylcarbamoyl group, a N-ethyl-N-octylcarbamoyl group, a N,N-dibutylcarbamoyl group, a N-propylcarbamoyl group, a N-phenylcarbamoyl group, a N-methyl-N-phenylcarbamoyl group, and a N,N-dicyclohexylcarbamoyl group), an amino group (for example, an amino group having preferably 32 or less carbon atoms, more preferably 24 or less carbon atoms; examples thereof include an amino group, a methylamino group, a N,N-dibutylamino group, a tetradecylamino group, a 2-ethylhexylamino group, and a cyclohexylamino group), an anilino group (for example, an anilino group having preferably 6 to 32 carbon atoms, more preferably 6 to 24 carbon atoms; examples thereof include an anilino group and a N-methylanilino group), a heterocyclic amino group (for example, a heterocyclic amino group having preferably 1 to 32 carbon atoms, more preferably 1 to 18 carbon atoms; examples thereof include a 4-pyridyl amino group), a carbonamido group (for example, a carbonamido group having preferably 2 to 48 carbon atoms, more preferably 2 to 24 carbon atoms; examples thereof include an acetamide group, a benzamide group, a tetradecaneamido group, a pivaloylamido group, and a cyclohexaneamido group), a ureido group (for example, a ureido group having preferably 1 to 32 carbon atoms, more preferably 1 to 24 carbon atoms; examples thereof include a ureido group, a N,N-dimethylureido group, and a N-phenylureido group), an imido group (for example, an imido group having preferably 36 or less carbon atoms, more preferably 24 or less carbon atoms; examples thereof include a N-succinimido group and a N-phthalimido group), an alkoxycarbonylamino group (for example, an alkoxycarbonylamino group having preferably 2 to 48 carbon atoms, more preferably 2 to 24 carbon atoms; examples thereof include a methoxycarbonylamino group, an ethoxycarbonylamino group, a t-butoxycarbonylamino group, an octadecyloxycarbonylamino group, and a cyclohexyloxycarbonylamino group), an aryloxycarbonylamino group (for example, an aryloxycarbonylamino group having preferably 7 to 32 carbon atoms, more preferably 7 to 24 carbon atoms; examples thereof include a phenoxycarbonylamino group), a sulfonamido group (for example, a sulfonamido group having preferably 1 to 48 carbon atoms, more preferably 1 to 24 carbon atoms; examples thereof include a methanesulfonamido group, a butanesulfonamido group, a benzenesulfonamido group, a hexadecanesulfonamido group, and a cyclohexanesulfonamido group), a sulfamoylamino group (for example, a sulfamoylamino group having preferably 1 to 48 carbon atoms, more preferably 1 to 24 carbon atoms; examples thereof include a N,N-dipropylsulfamoylamino group and a N-ethyl-N-dodecylsulfamoylamino group), an azo group (for example, an azo group having preferably 1 to 32 carbon atoms, more preferably 1 to 24 carbon atoms; examples thereof include a phenylazo group and a 3-pyrazolylazo group), an alkylthio group (for example, an alkylthio group having preferably 1 to 48 carbon atoms, more preferably 1 to 24 carbon atoms; examples thereof include a methylthio group, an ethylthio group, an octylthio group, and a cyclohexylthio group), an arylthio group (for example, an arylthio group having preferably 6 to 48 carbon atoms, more preferably 6 to 24 carbon atoms; examples thereof include a phenylthio group), a heterocyclic thio group (for example, a heterocyclic thio group having preferably 1 to 32 carbon atoms, more preferably 1 to 18 carbon atoms; examples thereof include a 2-benzothiazolylthio group, a 2-pyridylthio group, and a 1-phenyltetrazolylthio group), an alkylsulfinyl group (for example, an alkylsulfinyl group having preferably 1 to 32 carbon atoms, more preferably 1 to 24 carbon atoms; examples thereof include a dodecanesulfinyl group), an arylsulfinyl group (for example, an arylsulfinyl group having preferably 6 to 32 carbon atoms, more preferably 6 to 24 carbon atoms; examples thereof include a phenylsulfinyl group), an alkylsulfonyl group (for example, an alkylsulfonyl group having preferably 1 to 48 carbon atoms, more preferably 1 to 24 carbon atoms; examples thereof include a methylsulfonyl group, an ethylsulfonyl group, a propylsulfonyl group, a butylsulfonyl group, an isopropylsulfonyl group, a 2-ethylhexylsulfonyl group, a hexadecylsulfonyl group, an octylsulfonyl group, and a cyclohexylsulfonyl group), an arylsulfonyl group (for example, an arylsulfonyl group having preferably 6 to 48 carbon atoms, more preferably 6 to 24 carbon atoms; examples thereof include a phenylsulfonyl group and a 1-naphthylsulfonyl group), a sulfamoyl group (for example, a sulfamoyl group having preferably 32 or less carbon atoms, more preferably 24 or less carbon atoms; examples thereof include a sulfamoyl group, a N,N-dipropylsulfamoyl group, a N-ethyl-N-dodecylsulfamoyl group, a N-ethyl-N-phenylsulfamoyl group, and a N-cyclohexylsulfamoyl group), a sulfo group, a phosphonyl group (for example, a phosphonyl group having preferably 1 to 32 carbon atoms, more preferably 1 to 24 carbon atoms; examples thereof include a phenoxyphosphonyl group, an octyloxyphosphonyl group, and a phenylphosphonyl group), a phosphinoylamino group (for example, a phosphinoylamino group having preferably 1 to 32 carbon atoms, more preferably 1 to 24 carbon atoms; examples thereof include a diethoxyphosphinoylamino group and a dioctyloxyphosphinoylamino group).

When plural Ra's are included in Formula (A1) or (B1) or the tautomers thereof, the plural Ra's may be the same as or different from each other.

When the substituent represented by Ra in Formula (A1) or Formula (B1) may further have at least one additional substituent, the additional substituent may be any one of the substituents represented by Ra. When the substituent represented by Ra is substituted with 2 or more additional substituents, the additional substituents may be the same as or different from each other.

In Formula (A1) or Formula (B1), m represents 0, 1, 2, or 3, preferably represents 0 or 1, and more preferably represents 0.

M in Formula (A1) or Formula (B1) represents a hydrogen atom, or an organic base or metal atom necessary for neutralizing a charge. Examples of the organic base include alkylamines, anilines, quaternary amines, guanidines, pyridines, and quinolines. Examples of the metal atom include alkali metal atoms. As M in Formula (A1) and Formula (B1), ammonia is also preferable. M is most preferably a hydrogen atom.

L in Formula (A1) or Formula (B1) represents a single bond, an alkylene group, —O—, —N(Rb)—, —S—, —SO—, or —$SO_2$—, and Rb represents a hydrogen atom, an alkyl group, an aryl group, a heterocyclic group, an acyl group, a carbamoyl group, an alkoxycarbonyl group, an alkylsulfonyl group, or an arylsulfonyl group.

The alkyl group, the aryl group, the heterocyclic group, the acyl group, the carbamoyl group, the alkoxycarbonyl group, the alkylsulfonyl group, and the arylsulfonyl group represented by Rb may each be further substituted with at least one additional substituent that is any one of the substituents represented by Ra. When one of these groups is substituted with 2 or more additional substituents, the additional substituents may be the same as or different from each other.

L is preferably an alkylene group, —O—, —S—, or —$SO_2$—, most preferably —S—, or —$SO_2$—.

$R_1$ to $R_6$ in Formula (A1) or Formula (B1) each independently represent a hydrogen atom or a substituent, and any one of the substituents represented by $R_1$ to $R_6$ is a divalent linking group that binds to -(L)- (a group which is the linking group in this case will be explained by a case where the -(L)- group is a hydrogen atom).

The substituents represented by $R_1$ to $R_6$ each have the same meanings as the substituents represented by Ra of Formula (A1) or Formula (B1), and preferable ranges and examples thereof are also the same.

When substituents represented by $R_1$ to $R_6$ may each further have at least one additional substituent, the additional substituent may be any one of the substituents represented by Ra. When a substituent represented by $R_1$ to $R_6$ is substituted with 2 or more additional substituents, the additional substituents may be the same as or different from each other.

When any one of the substituents represented by $R_1$ to $R_6$ is a divalent linking group, the divalent linking group may be a new divalent linking group formed by binding at least two substituents. For example, the new divalent linking group may be formed by binding at least two divalent linking groups selected from the group consisting of an alkylene group, an aralkylene group, an arylene group, a divalent heterocyclic group, —O—, —S—, —C(=O)O—, —OC(=O)—, —C(=O)—, —OC(=O)N(Rc)—, —C(=O)N(Rc)—, —N(Rc)C(=O)—, —N(Rc)C(=O)O—, —N(Rc)C(=O)N(Rd)—, —C(=O)N(Rc)C(=O)—, —SO—, —$SO_2$—, —$SO_3$—, —$SO_2$N(Rc)—, —N(Rc)$SO_2$—, —C(=O)N(Rc)$SO_2$—, and —$SO_2$N(Rc)$SO_2$—.

Rc and Rd each independently represent a hydrogen atom, an alkyl group, an aryl group, a heterocyclic group, an acyl group, an alkoxycarbonyl group, an alkylsulfonyl group, an arylsulfonyl group, a carbamoyl group, or a sulfamoyl group. The alkyl group, aryl group, heterocyclic group, acyl group, alkoxycarbonyl group, alkylsulfonyl group, arylsulfonyl group, carbamoyl group, and sulfamoyl group may each be substituted with an additional group which is any one of the substituents represented by Ra, and when substituted with 2 or more additional substituents, the additional substituents may be the same as or different from each other.

$R_7$ in Formula (A1) or Formula (B1) represents a hydrogen atom, a halogen atom, an alkyl group, an aryl group, or a heterocyclic group.

The alkyl group, the aryl group, and the heterocyclic group represented by $R_7$ have the same meanings as the alkyl group, the aryl group, and the heterocyclic group represented by Ra of Formula (A1) or Formula (B1), and the preferable ranges and examples thereof are also the same.

The alkyl group, the aryl group, or the heterocyclic group represented by $R_7$ may be substituted with an additional substituent which is any one of the substituents represented by Ra, and when they are substituted with 2 or more additional substituents, the additional substituents may be the same as or different from each other.

$R_7$ is preferably a hydrogen atom, an alkyl group, or an aryl group, more preferably a hydrogen atom.

Ma in Formula (A1) or Formula (B1) represents a metal or a metal compound which may form a complex.

The metal and the metal compound represented by Ma may be a divalent metal atom, a divalent metal oxide, a divalent metal hydroxide, or a divalent metal chloride. Example thereof include metals such as Zn, Mg, Si, Sn, Rh, Pt, Pd, Mo, Mn, Pb, Cu, Ni, Co, or Fe metal chlorides such as AlCl, InCl, FeCl, $TiCl_2$, $SnCl_2$, $SiCl_2$, or $GeCl_2$, metal oxides such as TiO or V=O, and metal hydroxides such as $Si(OH)_2$.

Among them, from the viewpoints of stability, spectroscopic property, heat resistance, light resistance, and production suitability of a complex, Fe, Zn, Mg, Si, Pt, Pd, Mo, Mn, Cu, Ni, Co, TiO, or V=O is preferable, Fe, Zn, Mg, Si, Pt, Pd, Cu, Ni, Co, or V=O is more preferable, Fe, Zn, Co, V=O, or Cu is further preferable, and Zn is most preferable.

$X_1$ in Formula (B1) represents a group necessary for neutralizing a charge of Ma, and examples thereof include a halogen atom, a hydroxyl group, a carboxylic acid group, a phosphoric acid group, and a sulfonic acid group.

$X_2$ in Formula (A1) or Formula (B1) may be any group as long as it is a group which may bind to Ma, and examples thereof include water, alcohols (e.g. methanol, ethanol, propanol), and compounds described in "Metal Chelate" [1] Takeichi Sakaguchi, Keihei Ueno (1995, Nankodo Co., Ltd.), [2] (1996), and [3] (1997).

In Formula (A1) or Formula (B1), p represents 0 or 1.

$X_1$ and $X_2$ in Formula (A1) or Formula (B1) may bind to each other to form a 5-membered, 6-membered, or 7-membered ring with Ma. The 5-membered, 6-membered, or 7-membered ring may be a saturated or unsaturated ring. The 5-membered, 6-membered or 7-membered ring may contain only carbon atoms or may be a heterocyclic ring having at least one atom selected from nitrogen, oxygen and sulfur atoms.

From the viewpoints of synthesis suitability, and stability and fastness of a compound, the compound represented by Formula (A1) or Formula (B1), or the tautomer thereof is preferably a dipyrromethene metal complex represented by Formula (1-A1) or Formula (1-B1), or a tautomer thereof.

Compounds Represented by Formula (1-A1) and Formula (1-B1) and Tautomers Thereof Formula (1-A1)

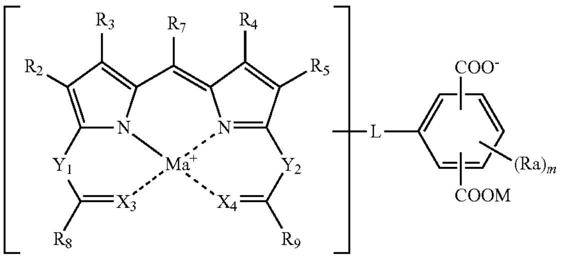

Formula (1-B1)

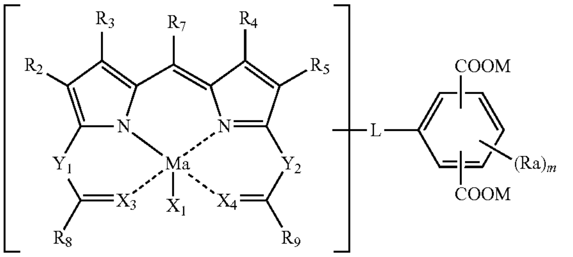

In the formulas, Ra represents a substituent; m represents an integer of 0, 1, 2 or 3; and M represents a hydrogen atom, or an organic base or metal atom necessary for neutralizing a charge. When there are plural Ra's, the plural Ra's may be the same as or different from each other. L represents a single bond, an alkylene group, —O—, —N(Rb)—, —S—, —SO—, or —$SO_2$—, and Rb represents a hydrogen atom, an alkyl group, an aryl group, a heterocyclic group, an acyl group, a carbamoyl group, an alkoxycarbonyl group, an alkylsulfonyl group, or an arylsulfonyl group.

$R_2$ to $R_5$ each independently represent a hydrogen atom or a substituent. $R_7$ represents a hydrogen atom, a halogen atom, an alkyl group, an aryl group, or a heterocyclic group. $R_8$ and $R_9$ each independently represent an alkyl group, an alkenyl group, an aryl group, a heterocyclic group, an alkoxy group, an aryloxy group, an amino group, an anilino group, or a heterocyclic amino group, provided that any one of the substituents represented by $R_2$ to $R_5$, $R_8$ and $R_9$ is a divalent linking group that binds to -L-.

Ma represents a metal or a metal compound; $X_1$ represents a group necessary for neutralizing a charge of Ma; $X_3$ and $X_4$ each independently represent NR (in which R represents a hydrogen atom, an alkyl group, an alkenyl group, an aryl group, a heterocyclic group, an acyl group, an alkylsulfonyl group, or an arylsulfonyl group), a nitrogen atom, an oxygen atom, or a sulfur atom; $Y_1$ and $Y_2$ each independently represent NR (in which R represents a hydrogen atom, an alkyl group, an alkenyl group, an aryl group, a heterocyclic group, an acyl group, an alkylsulfonyl group, or an arylsulfonyl group), or an oxygen atom; $R_8$ and $Y_1$ may bind together to form a 5-membered, 6-membered or 7-membered ring; and $R_9$ and $Y_2$ may bind together to form a 5-membered, 6-membered, or 7-membered ring. $X_1$ represents a group necessary for neutralizing a charge of Ma.

Hereinbelow, Formula (1-A1) and Formula (1-B1) will be described in detail.

Ra, m, M, L, $R_2$ to $R_5$, $R_7$, Ma and $X_1$ shown in Formula (1-A1) or Formula (1-B1) have the same meanings as those shown in Formula (A1) or Formula (B1), and the preferable ranges and examples thereof are also the same.

Any one of the substituents represented by $R_2$ to $R_5$, $R_8$ and $R_9$ in Formula (1-A1) or Formula (1-B1) is a divalent linking group that binds to -L-, and explanation of this any divalent group of $R_2$ to $R_5$, $R_8$ and $R_9$ is expressed by substituent of a hydrogen atom for -L-.

$R_8$ and $R_9$ in Formula (1-A1) or Formula (1-B1) each independently represent an alkyl group, an alkenyl group, an aryl group, a heterocyclic group, an alkoxy group, an aryloxy group, an amino group, an anilino group, or a heterocyclic amino group.

The preferable ranges and examples of the alkyl group, the alkenyl group, the aryl group, the heterocyclic group, the alkoxy group, the aryloxy group, the amino group, the anilino group and the heterocyclic amino group represented by $R_8$ or $R_9$ are the same as those of the substituents represented by Ra.

The alkyl group, the alkenyl group, the aryl group, the heterocyclic group, the alkoxy group, the aryloxy group, the amino group, the anilino group and the heterocyclic amino group represented by $R_8$ or $R_9$ may each be further substituted with an additional substituent which is any one of the substituents represented by Ra. When they are substituted with two or more additional substituents, the additional substituents may be the same as or different from each other.

$R_8$ and $R_9$ are each preferably an alkyl group, an alkenyl group, an aryl group, a heterocyclic group, an alkoxy group, an amino group, or an anilino group, more preferably an alkyl group, an alkenyl group, or an aryl group, and most preferably an alkyl group or an aryl group.

When a substituent represented by $R_8$ or $R_9$ is a divalent linking group, the divalent linking group may be a new divalent linking group formed by binding at least two substituents. For example, the new divalent linking group may be formed by binding at least two divalent linking groups selected from the group consisting of an alkylene group, an aralkylene group, an arylene group, a divalent heterocyclic group, —O—, —S—, —C(═O)O—, —OC(═O)—, —C(═O)—, —OC(═O)N(Rc)—, —C(═O)N(Rc)—, —N(Rc)C(═O)—, —N(Rc)C(═O)O—, —N(Rc)C(═O)N(Rd)—, —SO—, —$SO_2$—, —$SO_3$—, —$SO_2$N(Rc)—, —N(Rc)$SO_2$—, —C(═O)N(Rc)$SO_2$—, and —$SO_2$N(Rc)$SO_2$—.

Rc and Rd each independently represent a hydrogen atom, an alkyl group, an aryl group, a heterocyclic group, an acyl group, an alkoxycarbonyl group, an alkylsulfonyl group, an arylsulfonyl group, a carbamoyl group, or a sulfamoyl group. These alkyl group, aryl group, heterocyclic group, acyl group, alkoxycarbonyl group, alkylsulfonyl group, arylsulfonyl group, carbamoyl group, and sulfamoyl group may be substituted with an additional substituent which is any one of the substituents represented by Ra. When they are substituted with two or more additional substituents, the additional substituents may be the same as or different from each other.

$X_3$ and $X_4$ in Formula (1-A1) or Formula (1-B1) each independently represent NR (in which R represents a hydrogen atom, an alkyl group, an alkenyl group, an aryl group, a heterocyclic group, an acyl group, an alkylsulfonyl group, or an arylsulfonyl group), a nitrogen atom, an oxygen atom, or a sulfur atom. Preferable examples of the alkyl group, the alkenyl group, the aryl group, the heterocyclic group, the acyl group, the alkylsulfonyl group, and the arylsulfonyl group represented by R are the same as the alkyl group, the alkenyl group, the aryl group, the heterocyclic group, the acyl group, the alkylsulfonyl group, and the arylsulfonyl group represented by Ra.

When R may further have at least one additional substituent, the additional substituent may be any one of the substituents represented by Ra. When R is substituted with two or more additional substituents, the additional substituents may be the same as or different from each other.

$X_3$ and $X_4$ each represent preferably NR (in which R is a hydrogen atom, an alkyl group, an aryl group, an alkylsulfonyl group, or an arylsulfonyl group) or an oxygen atom, and from the viewpoints of synthesis suitability, and stability and fastness of a compound, an oxygen atom is most preferable.

$Y_1$ and $Y_2$ in Formula (1-A1) or Formula (1-B1) each independently represent NR (in which R is a hydrogen atom, an alkyl group, an alkenyl group, an aryl group, a heterocyclic group, an acyl group, an alkylsulfonyl group, or an arylsulfonyl group) or an oxygen atom, and R in NR has the same meaning as that of R in NR as an example of $X_3$ and $X_4$.

In Formula (1-A1) or Formula (1-B1), $R_8$ and $Y_1$ may bind together to form a 5-membered, 6-membered or 7-membered ring; and $R_9$ and $Y_2$ may bind together to form a 5-membered, 6-membered, or 7-membered ring. $X_1$ represents a group necessary for neutralizing a charge.

Formula (A1) and Formula (1-A1) are respectively further preferably represented by Formula (2-A1), and Formula (B1) and Formula (1-B1) are respectively further preferably represented by Formulae (2-B1).

Compounds Represented by Formula (2-A1) and Formula (2-B1)

Formula (2-A1)

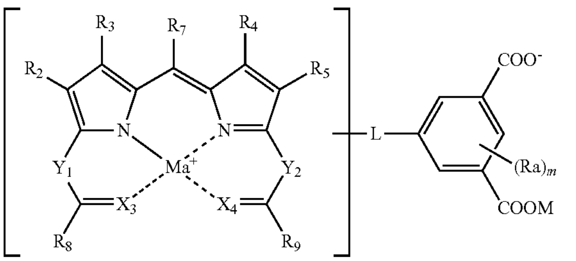

-continued

Formula (2-B1)

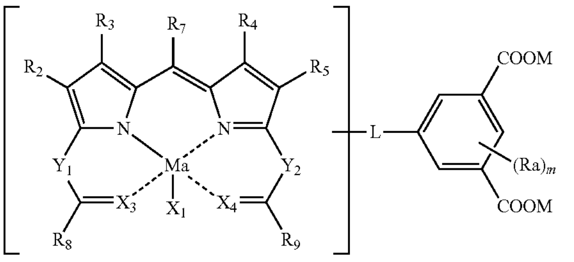

In the formulas, Ra, m, M, L, $R_2$ to $R_5$, $R_7$, $R_8$, $R_9$, Ma, $X_1$, $X_3$, $X_4$, $Y_1$, and $Y_2$ have the same meanings as in Formula (1-A1) and Formula (1-B1), respectively, and the preferable ranges and examples thereof are also the same.

Tautomers of the compounds represented by Formula (1-A1), Formula (1-B1), Formula (2-A1), and Formula (2-B1) will be described.

Tautomers of compounds represented by Formula (1-A1), Formula (1-B1), Formula (2-A1), and Formula (2-B1) may be any tautomer thereof as long as it is a compound having a structure which may be formed by movement of one hydrogen atom in the molecule of the compound. For example, the pyrromethene skeletons of Formula (1-A1), Formula (1-B1), Formula (2-A1), and Formula (2-B1) may each be one of the structures represented by the following Formula (a) to Formula (f).

Formula (a)

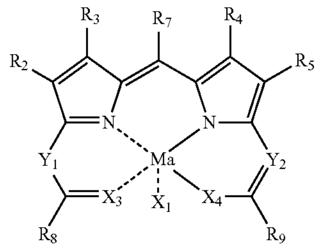

Formula (b)

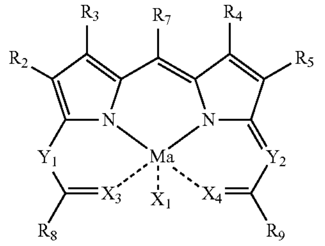

Formula (c)

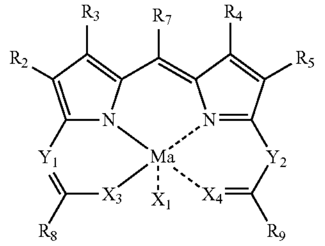

-continued

Formula (d)

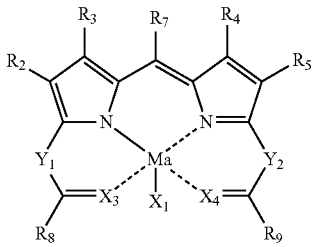

Formula (e)

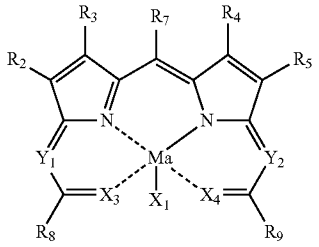

Formula (f)

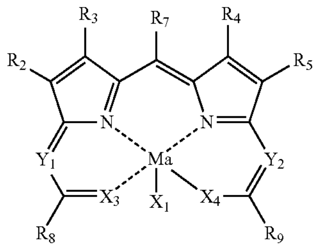

Respective substituents in the formulas have the same meanings as in Formula (1-A1), Formula (1-B1), Formula (2-A1), and Formula (2-B1). $X_1$ has the same meanings as that of $X_1$ of Formula (1-A1).

From the viewpoints of synthesis suitability, and stability and solubility in an organic solvent of a compound, Formula (1-A1) and Formula (2-A1) are each further preferably represented by the following Formula (C1) or a tautomer thereof, and Formula (1-B1) and Formula (2-B1) are each further preferably represented by the following Formula (D1) or a tautomer thereof.

Compounds Represented by Formula (C1) and Formula (D1)

Formula (C1)

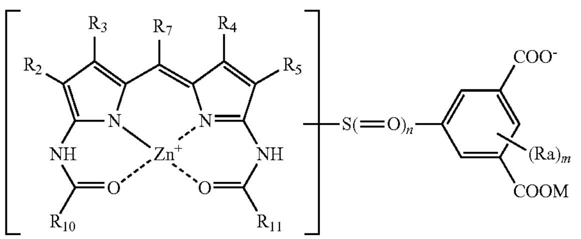

-continued

Formula (D1)

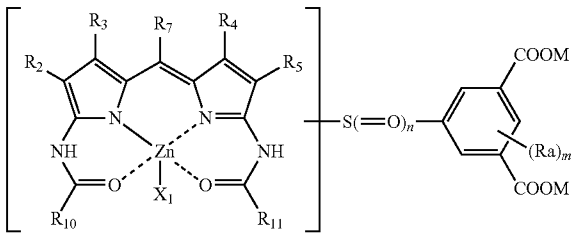

In the formulas, Ra, m, M, $R_2$ to $R_5$, $R_7$ and $X_1$ have the same meanings as in Formula (A1), Formula (B1), Formula (1-A1), and Formula (1-B1), and the preferable ranges and examples thereof are also the same.

In the formulas, n represents 0 or 2, and $R_{10}$ and $R_{11}$ each independently represent an alkyl group, an alkenyl group, an aryl group, or a heterocyclic group, provided that any one of the substituents represented by $R_2$ to $R_5$, $R_{10}$, and $R_{11}$ is a divalent linking group that binds to —S(═O)n-.

$R_{10}$ and $R_{11}$ in Formula (C1) or Formula (D1) each independently represent an alkyl group, an alkenyl group, an aryl group, or a heterocyclic group.

The alkyl group, the alkenyl group, the aryl group, and the heterocyclic group represented by $R_{10}$ or $R_{11}$ may each be further substituted with an additional substituent that is any one of the substituents represented by Ra. When they are substituted with two or more additional substituents, the additional substituents may be same as or different from each other.

From the viewpoints of synthesis suitability, and stability of a compound, $R_{10}$ and $R_{11}$ each preferably independently represent an alkyl group or an aryl group.

—S(═O)n- is preferably bound to any one of $R_{10}$ and $R_{11}$, from the viewpoint of synthesis suitability.

When a substituent represented by $R_{10}$ or $R_{11}$ is a divalent linking group, the divalent linking group may be a new divalent linking group formed by binding at least two substituents. For example, the new divalent linking group may be formed by binding at least tow divalent linking groups selected from the group consisting of an alkylene group, an aralkylene group, an arylene group, a divalent heterocyclic group, —O—, —S—, —C(═O)O—, —OC(═O)—, —C(═O)—, —OC(═O)N(Rc)—, —C(═O)N(Rd)—, —N(Rc)C(═O)—, —N(Rc)C(═O)O—, —N(Rc)C(═O)N(Rd)—, —SO—, $—SO_2—$, $—SO_3—$, $—SO_2N(Rc)—$, $—N(Rc)SO_2—$, $—C(═O)N(Rc)SO_2—$, and $—SO_2N(Rc)SO_2—$.

Rc and Rd each independently represent a hydrogen atom, an alkyl group, an aryl group, a heterocyclic group, an acyl group, an alkoxycarbonyl group, an alkylsulfonyl group, an arylsulfonyl group, a carbamoyl group, or a sulfamoyl group. These alkyl group, aryl group, heterocyclic group, acyl group, alkoxycarbonyl group, alkylsulfonyl group, arylsulfonyl group, carbamoyl group, and sulfamoyl group may each be substituted with at least one additional substituent that is any one of the substituents represented by Ra. When they are substituted with two or more additional substituents, the additional substituents may be the same as or different from each other.

Next, a preferable range of the compounds of the first exemplary embodiment of the invention will be described.

Formula (A1) is more preferable than Formula (B1), Formula (1-A1) is more preferable than Formula (1-B1), Formula (2-A1) is more preferable than Formula (2-B1), and Formula (C1) is more preferable than Formula (D1).

Formula (A1) and Formula (B1) are respectively preferably represented by the corresponding Formula (1-A1) and Formula (1-B1), more preferably represented by the corresponding Formula (2-A1) and Formula (2-B1), and are further preferably represented by the corresponding Formula (C1) and Formula (D1).

In Formula (A1) and Formula (B1), it is preferable that any one of $R_1$ or $R_6$ is a divalent linking group that binds to -L-. In Formula (1-A1), Formula (1-B1), Formula (2-A1), and Formula (2-B1), it is preferable that $R_8$ or $R_9$ is a divalent linking group that binds to -L-. Further, in Formula (C1) and Formula (D1), it is preferable that $R_{10}$ or $R_{11}$ is a divalent linking group that binds to —S(═O)n-.

When any one of $R_1$ to $R_6$ of Formula (A1) or Formula (B1) is a divalent linking group that binds to -L-, the divalent linking group is preferably an alkylene group, an aralkylene group, an arylene group, or a divalent heterocyclic group or a divalent linking group formed by any one of an alkylene group, an aralkylene group, and an arylene group, and any one of —O—, —S—, —C(═O)O—, —OC(═O)—, —C(═O)—, —OC(═O)N(Rc)—, —C(═O)N(Rd)—, —N(Rc)C(═O)—, —N(Rc)C(═O)O—, —N(Rc)C(═O)N(Rd)—, —SO—, —$SO_2$—, —$SO_2$N(Rc)—, and —N(Rc)$SO_2$—). Further preferable is an alkylene group, an aralkylene group, or an arylene group.

When any one of $R_2$ to $R_5$, $R_8$ and $R_9$ in Formula (1-A1), Formula (1-B1), Formula (2-A1), or Formula (2-B1) is a divalent linking group that binds to -L-, it is preferable that -L-binds to $R_8$ or $R_9$. The divalent linking group is preferably an alkylene group, an aralkylene group, an arylene group, or a divalent heterocyclic group, or a divalent linking group formed by binding any one of an alkylene group, an aralkylene group, and an arylene group, and any one of —O—, —S—, —C(═O)O—, —OC(═O)—, —C(═O)—, —OC(═O)N(Rc)—, —C(═O)N(Rd)-, —N(Rc)C(═O)—, —N(Rc)C(═O)O—, —N(Rc)C(═O)N(Rd)—, —SO—, —$SO_2$—, —$SO_2$N(Rc)-, and —N(Rc)$SO_2$—). Further preferable is an alkylene group, an aralkylene group, or an arylene group.

When any one of $R_2$ to $R_5$, $R_{10}$, and $R_{11}$ in Formula (C1) or Formula (D1) is a divalent linking group that binds to —S(═O)n-, —S(═O)n- preferably binds to $R_{10}$ or $R_{11}$. The divalent linking group is preferably an alkylene group, an aralkylene group, an arylene group, or a divalent heterocyclic group, or a divalent linking group formed by binding any one of an alkylene group, an aralkylene group, and an arylene group, and any one of —O—, —S—, —C(═O)O—, —OC(═O)—, —C(═O)—, —OC(═O)N(Rc)-, —C(═O)N(Rd)-, —N(Rc)C(═O)—, —N(Rc)C(═O)O—, —N(Rc)C(═O)N(Rd)-, —SO—, —$SO_2$—, —$SO_2$N(Rc)-, and —N(Rc)$SO_2$—. Further preferable is an alkylene group, an aralkylene group, or an arylene group.

The preferable ranges of respective substituents of Formula (A1), Formula (B1), Formula (1-A1), Formula (1-B1), Formula (2-A1), Formula (2-B1), Formula (C1), and Formula (D1) will be described below; however, in a combination of a preferable range of each substituent with a preferable range of formulae, the respective more preferable ranges are more preferable.

$R_1$ in Formula (A1) or Formula (B1) is preferably an alkyl group, an aryl group, a heterocyclic group, a group represented by —$Y_1$—C(═$X_3$)—$R_8$ shown in Formula (1-A1), Formula (1-B1), Formula (2-A1), or Formula (2-B1), or —NH—C(═O)—$R_{10}$ or —NH—C(═O)—$R_{11}$ shown in Formula (C1) or Formula (D1);

further preferably a group represented by —$Y_1$—C(═$X_3$)—$R_8$ shown in Formula (1-A1), Formula (1-B1), Formula (2-A1), or Formula (2-B1), or —NH—C(═O)—$R_{10}$ or —NH—C(═O)—$R_{11}$ shown in Formula (C1) or Formula (D1); and most preferably —NH—C(═O)—$R_{10}$ or —NH—C(═O)—$R_{11}$ shown in Formula (C1) and Formula (D1).

$R_6$ in Formula (A1) or Formula (B1) is an alkyl group, an aryl group, a heterocyclic group, a group represented by —$Y_2$—C(═$X_4$)—$R_9$ shown in Formula (1-A1), Formula (1-B1), Formula (2-A1), or Formula (2-B1), or —NH—C(═O)—$R_{11}$ shown in Formula (C1) or Formula (D1);

further preferably a group represented by —$Y_2$—C(═$X_4$)—$R_9$ shown in Formula (1-A1), Formula (1-B1), Formula (2-A1), or Formula (2-B1), or —NH—C(═O)—$R_{11}$ shown in Formula (C1) or Formula (D1); and most preferably —NH—C(═O)—$R_{11}$ shown in Formula (C1) or Formula (D1).

The preferable ranges and examples of $Y_1$, $X_3$, $Y_2$, $X_4$, and $R_8$ to $R_{11}$ are as described below.

$X_2$ in Formula (A1) or Formula (B1) is preferably water, alcohols (e.g. methanol, ethanol, propanol), or a compound described in "Metal Chelate" [1] Takeichi Sakaguchi/Keihei Ueno (1995, Nankodo Co., Ltd.), the same [2] (1996), and the same [3] (1997), and further preferably water or alcohols, and most preferably p is 0.

In Formula (A1), Formula (B1), Formula (1-A1), Formula (1-B1), Formula (2-A1), Formula (2-B1), Formula (C1), or Formula (D1), Ra is preferably a halogen atom, an alkyl group, or an alkoxy group, and m is 0 or 1, and most preferably is 0.

M in Formula (A1), Formula (B1), Formula (1-A1), Formula (1-B1), Formula (2-A1), Formula (2-B1), Formula (C1), or Formula (D1) is preferably a hydrogen atom, a trialkylamine having 3 to 14 carbon atoms, a quaternary ammonium having 4 to 20 carbon atoms, or an alkali metal, more preferably a hydrogen atom, a trialkylamine having 3 to 9 carbon atoms, a quaternary ammonium salt having 4 to 8 carbon atoms, or an alkali metal, further preferably a hydrogen atom.

L in Formula (A1), Formula (B1), Formula (1-A1), Formula (1-B1), Formula (2-A1), or Formula (2-B1) is preferably —O—, —N(Rb), —S—, or —$SO_2$— (in which Rb is a hydrogen atom or an alkyl group having 1 to 4 carbon atoms), more preferably —O—, —S—, or —$SO_2$—, and most preferably —S— or $SO_2$—.

Ma in Formula (A1), Formula (B1), Formula (1-A1), Formula (1-B1), Formula (2-A1), or Formula (2-B1) is preferably Fe, Zn, Co, V═O, or Cu, further preferably Zn, Co, V═O, or Cu, most preferably Zn.

$R_2$ and $R_5$ in Formula (A1), Formula (B1), Formula (1-A1), Formula (1-B1), Formula (2-A1), Formula (2-B1), Formula (C1), or Formula (D1) each are preferably independently an alkyl group, an aryl group, a heterocyclic group, an alkoxycarbonyl group, an aryloxycarbonyl group, a cyano group, a carboxyl group, an acyl group, a carbamoyl group, an alkylthio group, an arylthio group, a heterocyclic thio group, an alkylsulfonyl group, an arylsulfonyl group, a heterocyclic sulfonyl group, an alkylsulfinyl group, an arylsulfinyl group, or a sulfamoyl group; more preferably a perfluoroalkyl group, an aryl group, a heterocyclic group, an alkoxycarbonyl group, an aryloxycarbonyl group, a cyano group, a carboxyl group, an acyl group, a carbamoyl group, an alkylsulfonyl group, an arylsulfonyl group, a heterocyclic sulfonyl group, or a sulfamoyl group; further preferably a perfluoroalkyl group, an aryl group, a heterocyclic group, an alkoxycarbonyl group, an aryloxycarbonyl group, a cyano group, a carboxyl group, an acyl group, a carbamoyl group, an alkylsulfonyl group, an arylsulfonyl group, or a sulfamoyl group; and most preferably a perfluoroalkyl group, an alkoxycarbonyl group, an aryloxycarbonyl group, a cyano group, a carbamoyl group, an alkylsulfonyl group, or an arylsulfonyl group.

$R_3$ and $R_4$ in Formula (A1), Formula (B1), Formula (1-A1), Formula (1-B1), Formula (2-A1), Formula (2-B1), Formula (C1), or Formula (D1) are each preferably independently an alkyl group, an aryl group, a heterocyclic group, an alkoxycarbonyl group, a cyano group, or a carbamoyl group; more preferably an alkyl group, an aryl group, a heterocyclic group, or a cyano group; and most preferably an alkyl group, an aryl group, or a heterocyclic group.

$R_7$ in Formula (A1), Formula (B1), Formula (1-A1), Formula (1-B1), Formula (2-A1), Formula (2-B1), Formula (C1), or Formula (D1) is preferably a hydrogen atom, a halogen atom, an alkyl group, an aryl group, or a heterocyclic group; more preferably a hydrogen atom, an alkyl group, an aryl group, or a heterocyclic group; further preferably a hydrogen atom, an alkyl group, or an aryl group; and most preferably a hydrogen atom.

$X_1$ in Formula (B1), Formula (1-B1), Formula (2-B1), or Formula (D1) is preferably a halogen atom, an alkylcarbonyloxy group, an arylcarbonyloxy group, a heterocyclic carbonyloxy group, a sulfonic acid group, an alkylsulfonyloxy group, an arylsulfonyloxy group, or a phosphoric acid group; and more preferably a chlorine atom, an alkylcarbonyloxy group, an arylcarbonyloxy group, a sulfonic acid group, an alkylsulfonyloxy group, or an arylsulfonyloxy group.

$R_8$ and $R_9$ in Formula (1-A1), Formula (1-B1), Formula (2-A1), and Formula (2-B1) each are preferably independently an alkyl group, an alkenyl group, an aryl group, a heterocyclic group, an alkoxy group, an amino group, or an anilino group; more preferably an alkyl group, an alkenyl group, an aryl group, or a heterocyclic group; further preferably an alkyl group, an alkenyl group or an aryl group; and most preferably an alkyl group or an aryl group.

$X_3$ and $X_4$ in Formula (1-A1), Formula (1-B1), Formula (2-A1), or Formula (2-B1) each are preferably independently NR (in which R represents a hydrogen atom, an alkyl group, an alkenyl group, an aryl group, a heterocyclic group, an acyl group, an alkylsulfonyl group, or an arylsulfonyl group), a nitrogen atom, or an oxygen atom; more preferably —NH—, a nitrogen atom, or an oxygen atom; and most preferably an oxygen atom.

$Y_1$ and $Y_2$ in Formula (1-A1), Formula (1-B1), Formula (2-A1), or Formula (2-B1) each are preferably independently NR (in which R is a hydrogen atom, an alkyl group, an alkenyl group, an aryl group, a heterocyclic group, an acyl group, an alkylsulfonyl group, or an arylsulfonyl group), more preferably NR (in which R is a hydrogen atom, or an alkyl group), and most preferably a —NH— group.

$R_{10}$ and $R_{11}$ in Formula (C1) or Formula (D1) each are preferably independently an alkyl group, an aryl group, or a heterocyclic group, and more preferably an alkyl group or an aryl group.

It is a preferably exemplary embodiment of Formula (C1) or Formula (D1), in which $R_2$ and $R_5$ each are independently a perfluoroalkyl group, an aryl group, a heterocyclic group, an alkoxycarbonyl group, an aryloxycarbonyl group, a cyano group, a carboxyl group, an acyl group, a carbamoyl group, an alkylsulfonyl group, an arylsulfonyl group, or a sulfamoyl group (most preferably a perfluoroalkyl group, an alkoxycarbonyl group, an aryloxycarbonyl group, a cyano group, a carbamoyl group, an alkylsulfonyl group, or an arylsulfonyl group); $R_3$ and $R_4$ are each independently an alkyl group, an aryl group, a heterocyclic group, or a cyano group (most preferably, an alkyl group, an aryl group, or a heterocyclic group); $R_7$ is a hydrogen atom, an alkyl group, or an aryl group (most preferably a hydrogen atom); $X_1$ is a chlorine atom, an alkylcarbonyloxy group, an arylcarbonyloxy group, a sulfonic acid group, an alkylsulfonyloxy group, or an arylsulfonyloxy group; $R_{10}$ and $R_{11}$ are each independently an alkyl group, an aryl group, or a heterocyclic group (more preferably an alkyl group or an aryl group); M is a hydrogen atom, a trialkylamine having 3 to 9 carbon atoms, a quaternary ammonium salt having 4 to 8 carbon atoms, or an alkali metal (further preferably a hydrogen atom); Ra is a halogen atom, an alkyl group, or an alkoxy group; m is 0 or 1 (most preferably m is 0); and n is 0 or 2.

Next, examples of the compounds represented by Formula (A1), Formula (B1), Formula (1-A1), Formula (1-B1), Formula (2-A1), Formula (2-B1), Formula (C1), or Formula (D1) are shown below, but the invention is not limited by them.

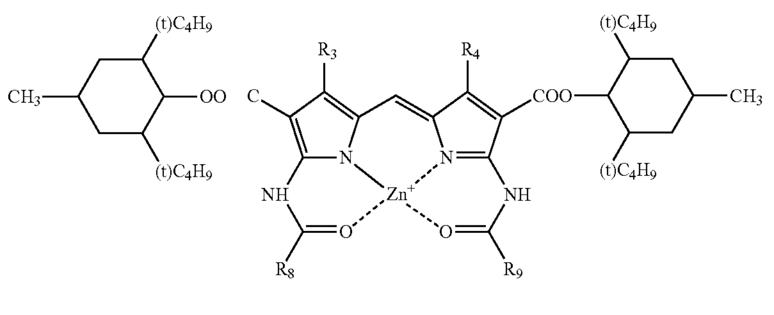

| | $R^3$, $R^4$ | $R^8$ | $R^9$ |
|---|---|---|---|
| A-1 | —$CH_3$ | —$CH_3$ | 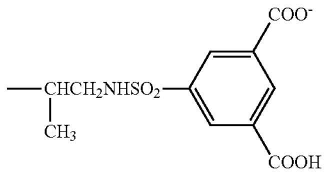 |

-continued

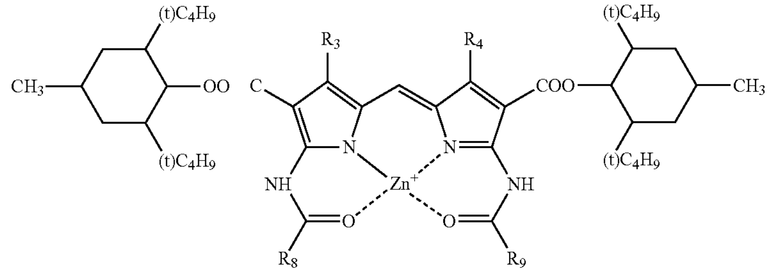

| | $R^3$, $R^4$ | $R^8$ | $R^9$ |
|---|---|---|---|
| A-2 | Same as above | 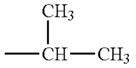 | Same as above |
| A-3 | Same as above | $—(t)C_4H_9$ | Same as above |
| A-4 | Same as above | 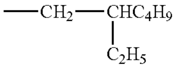 | Same as above |
| A-5 | Same as above | $—C_{12}H_{25}$ | Same as above |
| A-6 | Same as above | $—CH_2OCH_3$ | Same as above |
| A-7 | Same as above | $—CH_2CH_2COOC_2H_5$ | Same as above |
| A-8 | Same as above | $—CH_2OCH_2COOC_2H_5$ | Same as above |
| A-9 | Same as above | 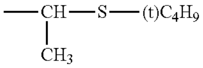 | Same as above |

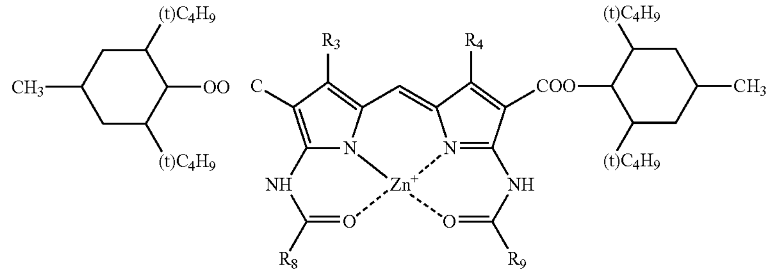

| | $R^3$, $R^4$ | $R^8$ | $R^9$ |
|---|---|---|---|
| A-10 | $—CH_3$ | 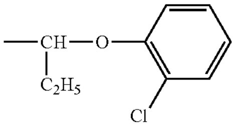 | 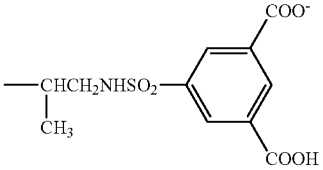 |
| A-11 | Same as above | 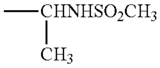 | Same as above |
| A-12 | Same as above | 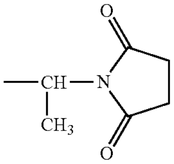 | Same as above |

-continued
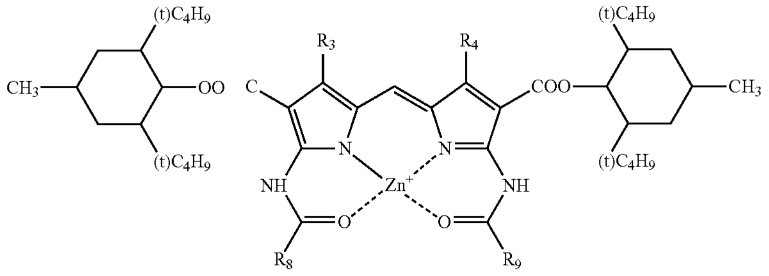
| | $R^3$, $R^4$ | $R^8$ | $R^9$ |
|---|---|---|---|
| A-13 | Same as above | 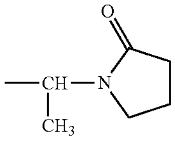 | Same as above |
| A-14 | Same as above | $—CH_2OCH_2COOH$ | Same as above |
| A-15 | Same as above | 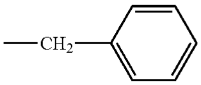 | Same as above |
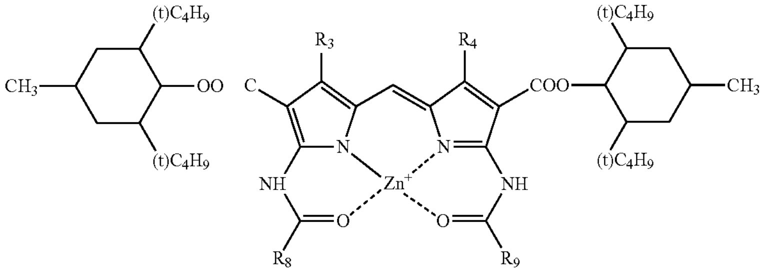
| | $R^3$, $R^4$ | $R^8$ | $R^9$ |
|---|---|---|---|
| A-16 | $—CH_3$ | $—CF_3$ | 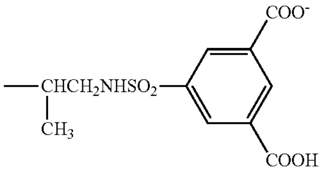 |
| A-17 | Same as above | $—OC_2H_5$ | Same as above |
| A-18 | Same as above | $—NHC_4H_9$ | Same as above |
| A-19 | $—C_2H_5$ | $—(t)C_4H_9$ | Same as above |
| A-20 | 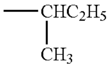 | Same as above | |
| A-21 | $—CH_3$ | Same as above | 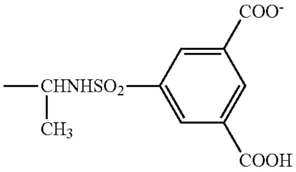 |

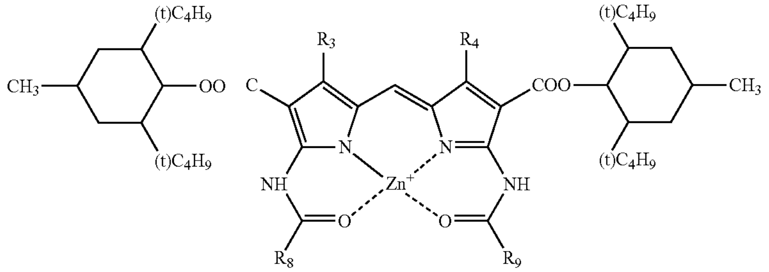
| | $R^3$, $R^4$ | $R^8$ | $R^9$ |
|---|---|---|---|
| A-22 | $—CH_3$ | $—(t)C_4H_9$ | 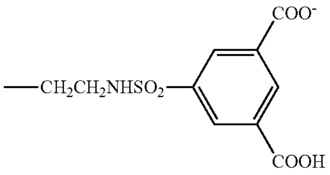 |
| A-23 | Same as above | Same as above | 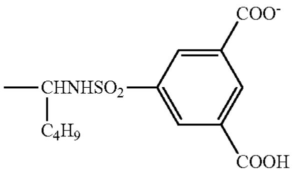 |
| A-24 | 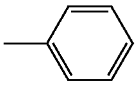 | $—CH_3$ | 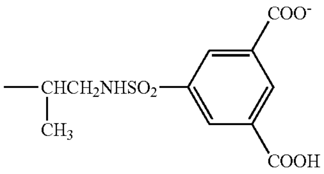 |
| A-25 | Same as above | $—(t)C_4H_9$ | Same as above |
| A-26 | Same as above | 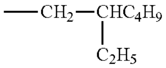 | Same as above |
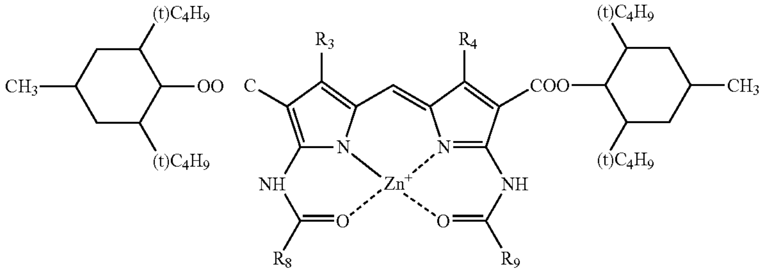
| | $R^3$, $R^4$ | $R^8$ | $R^9$ |
|---|---|---|---|
| A-27 | 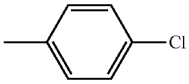 | $—(t)C_4H_9$ | 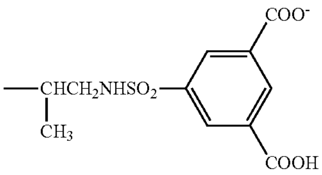 |

-continued
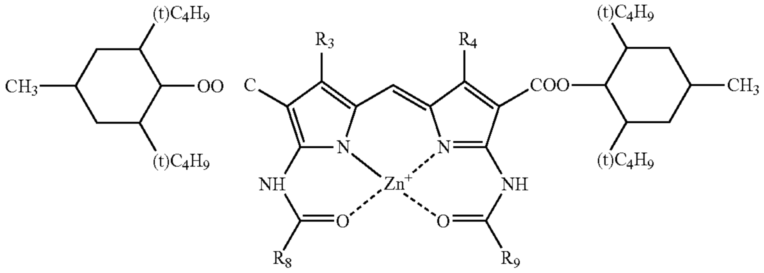
| | $R^3$, $R^4$ | $R^8$ | $R^9$ |
|---|---|---|---|
| A-28 | 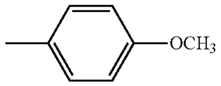 | Same as above | Same as above |
| A-29 | 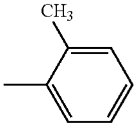 | Same as above | Same as above |
| A-30 | 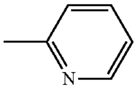 | Same as above | Same as above |
| A-31 | 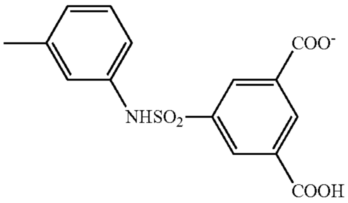 | Same as above | $—(t)C_4H_9$ |
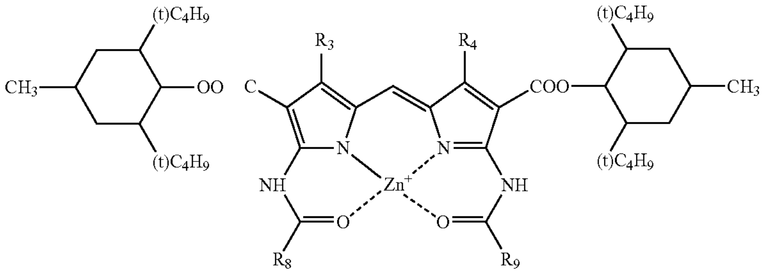
| | $R^3$, $R^4$ | $R^8$ | $R^9$ |
|---|---|---|---|
| A-32 | $—CH_3$ | $—(t)C_4H_9$ | 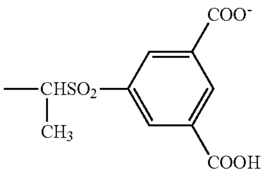 |
| A-33 | 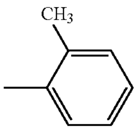 | Same as above | Same as above |

-continued
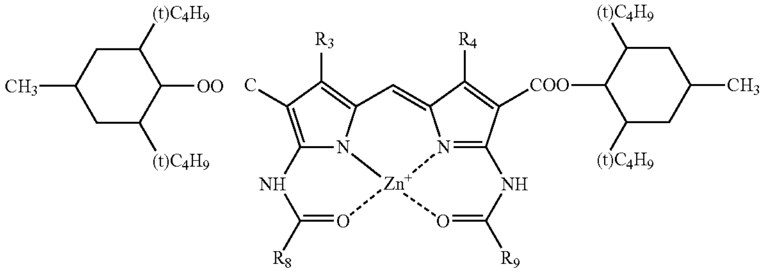
| | $R^3$, $R^4$ | $R^8$ | $R^9$ |
|---|---|---|---|
| A-34 | $—CH_3$ | $—CH_3$ | 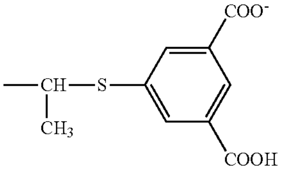 |
| A-35 | Same as above | $—(t)C_4H_9$ | 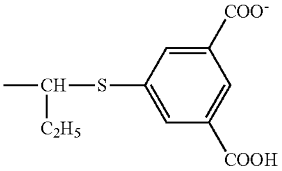 |
| A-36 | Same as above | 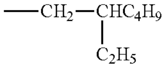 | Same as above |
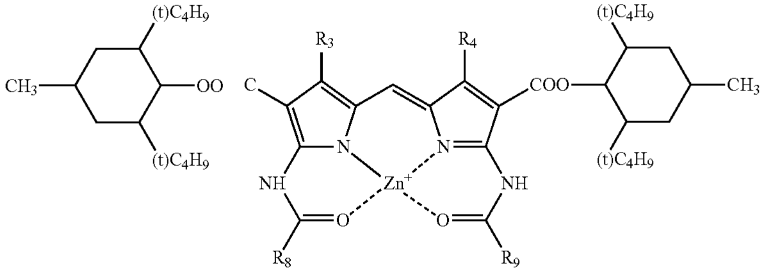
| | $R^3$, $R^4$ | $R^8$ | $R^9$ |
|---|---|---|---|
| A-37 | $—CH_3$ | $—(t)C_4H_9$ | 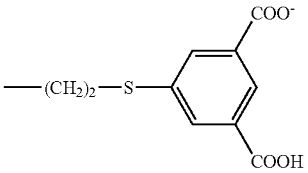 |
| A-38 | Same as above | Same as above | 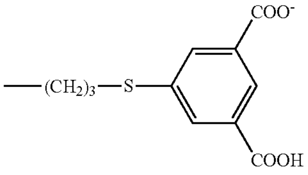 |

-continued
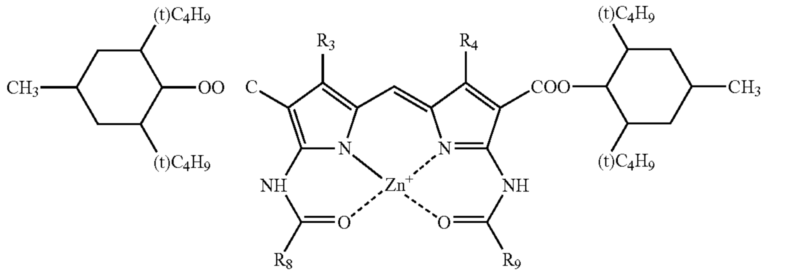
| | $R^3$, $R^4$ | $R^8$ | $R^9$ |
|---|---|---|---|
| A-39 | Same as above | Same as above | 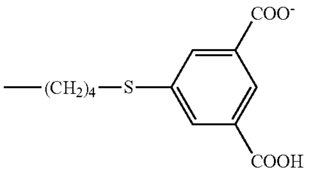 |
| A-40 | Same as above | 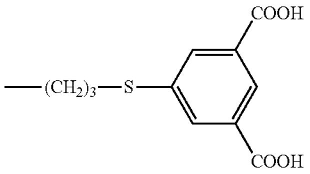 | 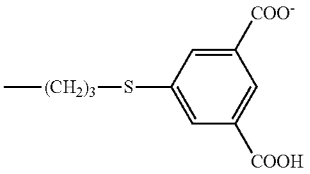 |
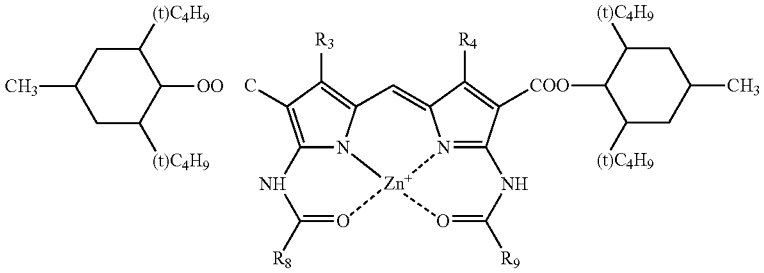
| | $R^3$, $R^4$ | $R^8$ | $R^9$ |
|---|---|---|---|
| A-41 | $-(t)C_4H_9$ | $-(t)C_4H_9$ | 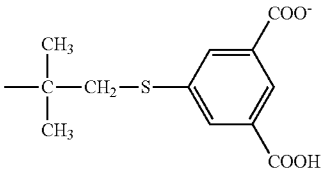 |
| A-42 | 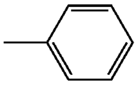 | $-CH_3$ | 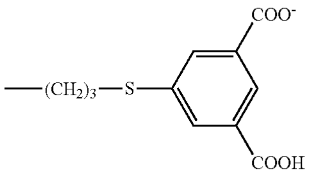 |
| A-43 | 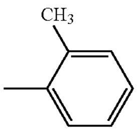 | Same as above | Same as above |
| A-44 | Same as above | $-(t)C_4H_9$ | Same as above |

-continued
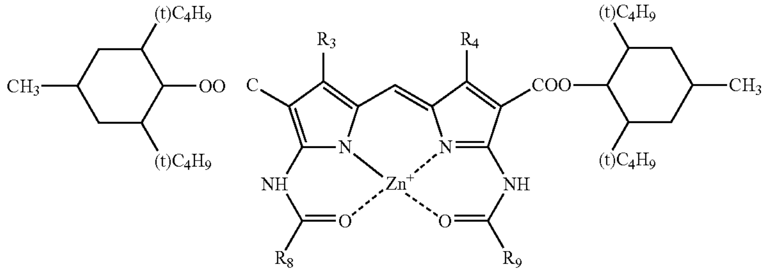
| | $R^3$, $R^4$ | $R^8$ | $R^9$ |
|---|---|---|---|
| A-45 | —$CH_3$ | 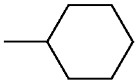 | Same as above |
| A-46 | 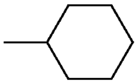 | —$CH_3$ | Same as above |
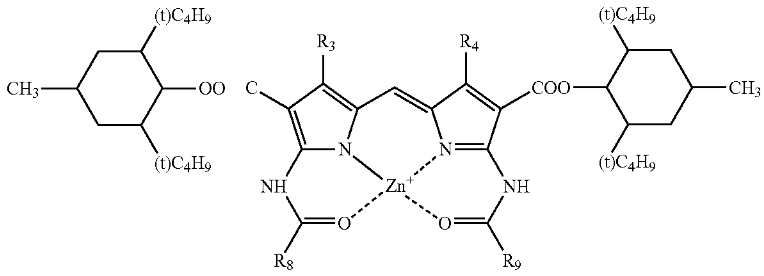
| | $R^3$, $R^4$ | $R^8$ | $R^9$ |
|---|---|---|---|
| B-1 | 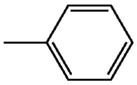 | 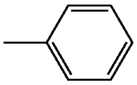 | 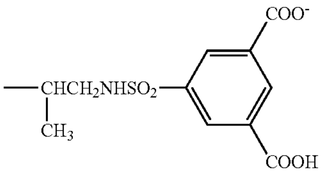 |
| B-2 | Same as above | Same as above | 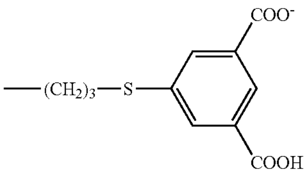 |
| B-3 | Same as above | 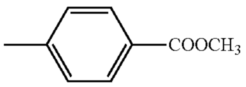 | Same as above |
| B-4 | Same as above | 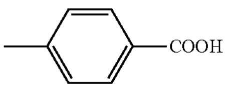 | Same as above |

-continued
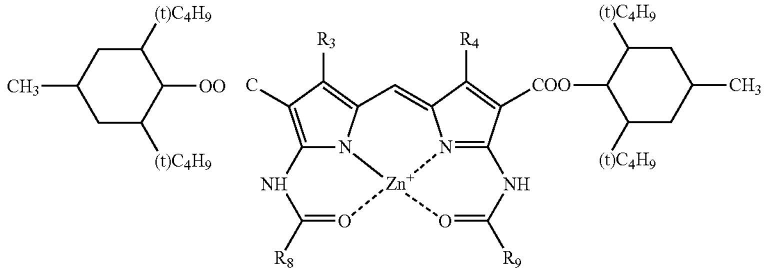
| | $R^3$, $R^4$ | $R^8$ | $R^9$ |
|---|---|---|---|
| B-5 | Same as above | 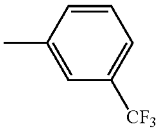 | Same as above |
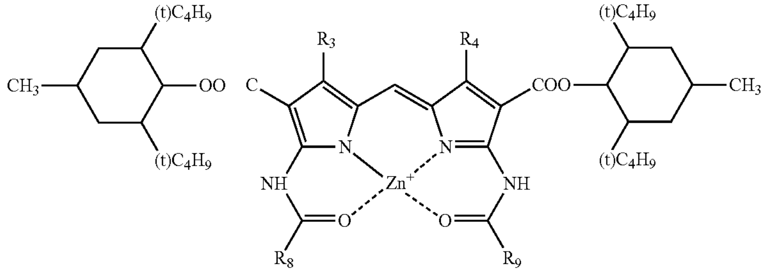
| | $R^3$, $R^4$ | $R^8$ | $R^9$ |
|---|---|---|---|
| B-6 | 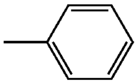 | 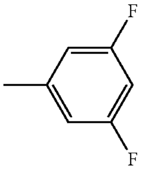 | 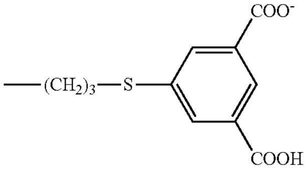 |
| B-7 | Same as above | 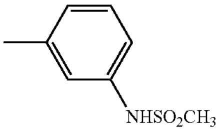 | Same as above |
| B-8 | Same as above | 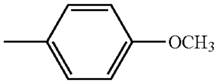 | 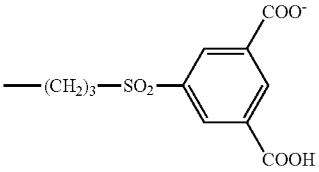 |
| B-9 | Same as above | 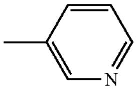 | Same as above |

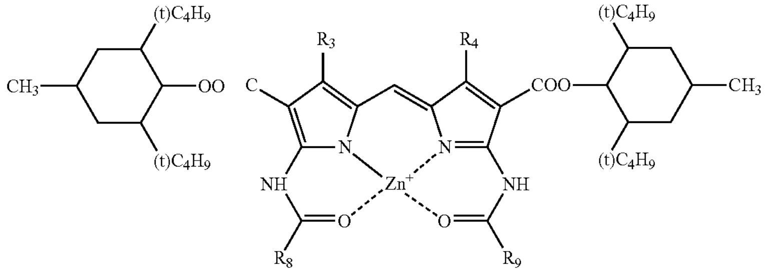
| | $R^3$, $R^4$ | $R^8$ | $R^9$ |
|---|---|---|---|
| B-10 | 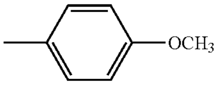 | 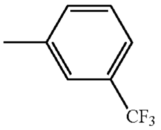 | 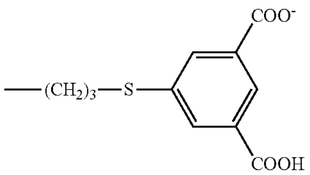 |
| B-11 | 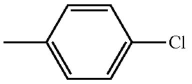 | Same as above | Same as above |
| B-12 | 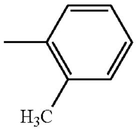 | Same as above | Same as above |
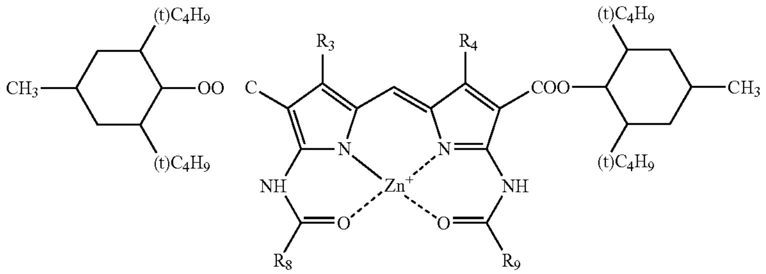
| | $R^3$ | $R^4$ | $R^8$ | $R^9$ |
|---|---|---|---|---|
| C-1 | $—CH_3$ | 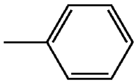 | $—(t)C_4H_9$ | 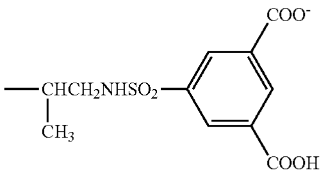 |
| C-2 | Same as above | Same as above | Same as above | 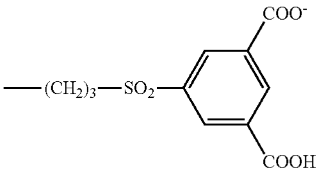 |

-continued
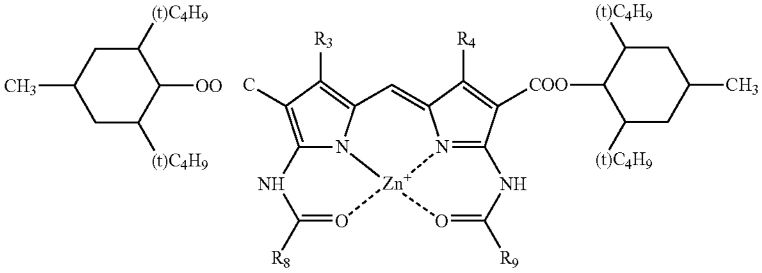
| | $R^3$ | $R^4$ | $R^8$ | $R^9$ |
|---|---|---|---|---|
| C-3 | Same as above | Same as above | Same as above | 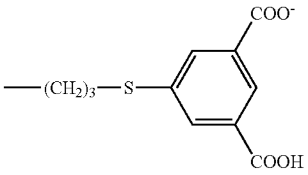 |
| C-4 | Same as above | 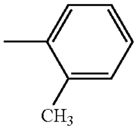 | Same as above | Same as above |
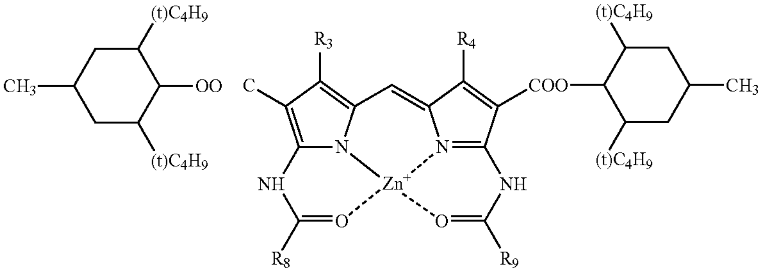
| | $R^3$ | $R^4$ | $R^8$ | $R^9$ |
|---|---|---|---|---|
| C-5 | $—CH_3$ | 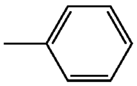 | 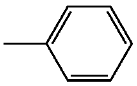 | 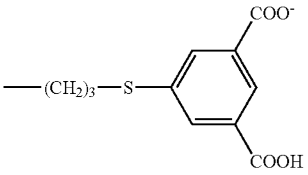 |
| C-6 | Same as above | Same as above | 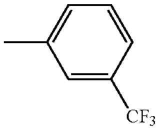 | Same as above |
| C-7 | Same as above | Same as above | 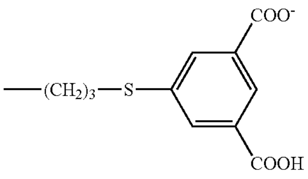 | 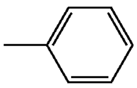 |

-continued
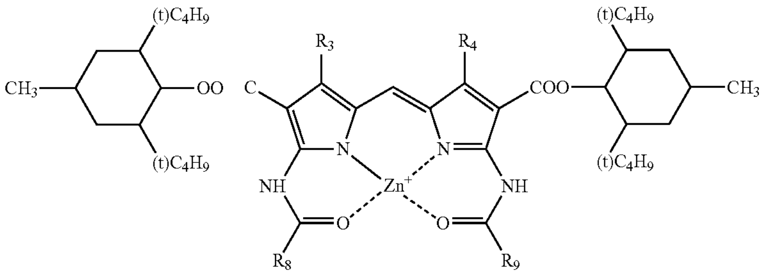
| | $R^3$ | $R^4$ | $R^8$ | $R^9$ |
|---|---|---|---|---|
| C-8 | Same as above | Same as above | 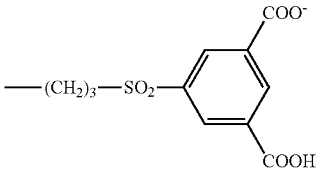 | Same as above |
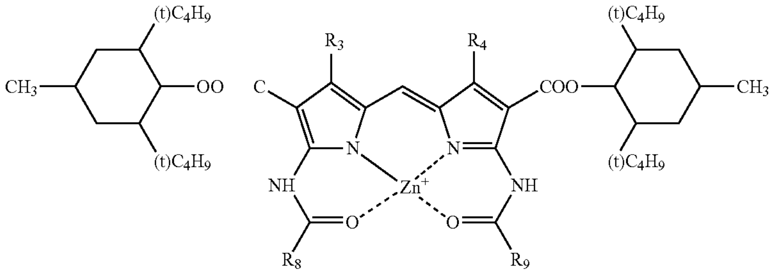
| | $R^3$ | $R^4$ | $R^8$ | $R^9$ |
|---|---|---|---|---|
| C-9 | $-CH_3$ | 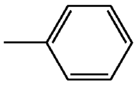 | 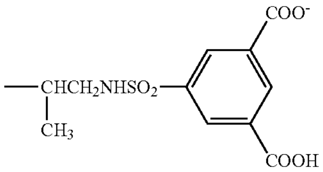 | 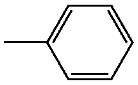 |
| C-10 | $-CF_3$ | Same as above | Same as above | Same as above |
| C-11 | 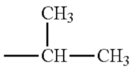 | Same as above | 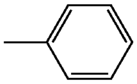 | 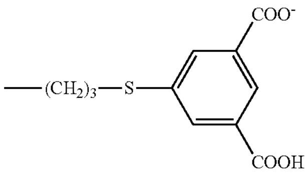 |

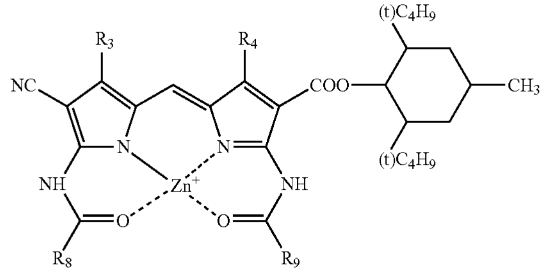
| | $R^3$ | $R^4$ | $R^8$ | $R^9$ |
|---|---|---|---|---|
| D-1 | 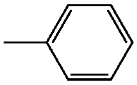 | 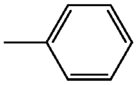 | 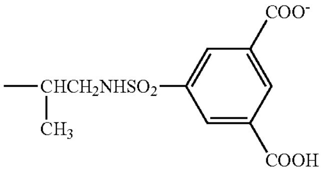 | 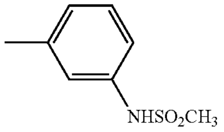 |
| D-2 | Same as above | Same as above | 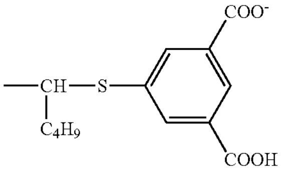 | 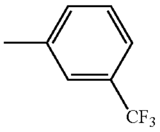 |
| D-3 | Same as above | Same as above | 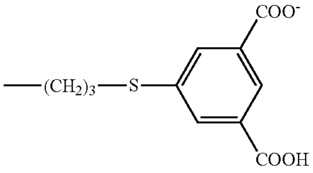 | Same as above |
| D-4 | Same as above | Same as above | Same as above | 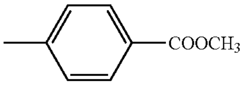 |
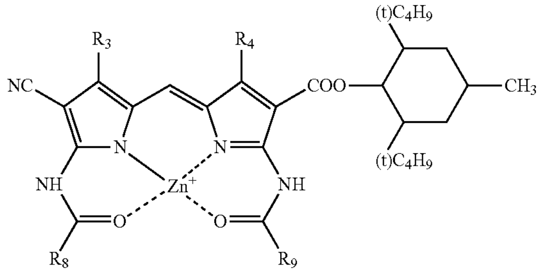
| | $R^3$ | $R^4$ | $R^8$ | $R^9$ |
|---|---|---|---|---|
| D-5 | 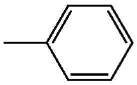 | 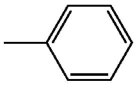 | 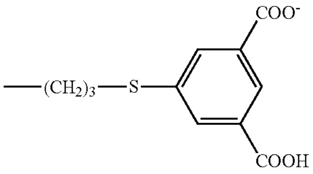 | 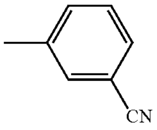 |

-continued
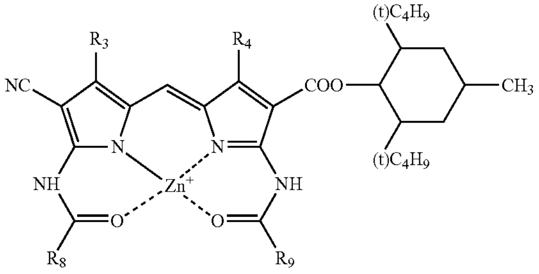
| | $R^3$ | $R^4$ | $R^8$ | $R^9$ |
|---|---|---|---|---|
| D-6 | Same as above | Same as above | 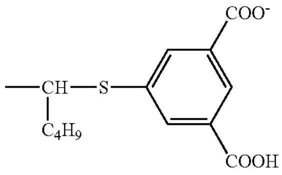 | 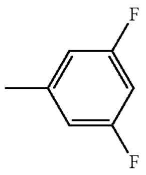 |
| D-7 | Same as above | Same as above | Same as above | 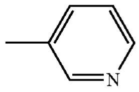 |
| D-8 | Same as above | Same as above | Same as above | 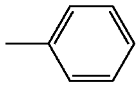 |
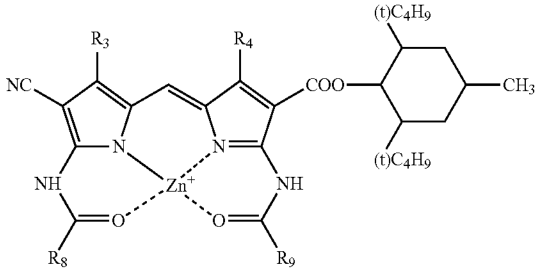
| | $R^3$ | $R^4$ | $R^8$ | $R^9$ |
|---|---|---|---|---|
| D-9 | 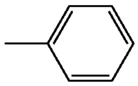 | 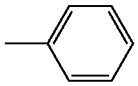 | 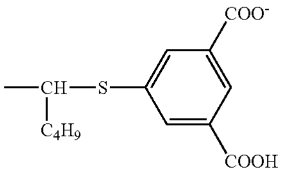 | 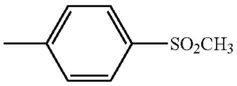 |
| D-10 | Same as above | Same as above | Same as above | —$(t)C_4H_9$ |
| D-11 | 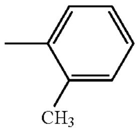 | —$CH_3$ | —$(t)C_4H_9$ | 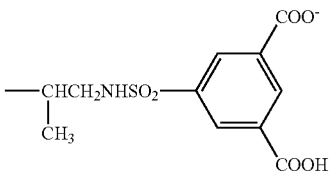 |

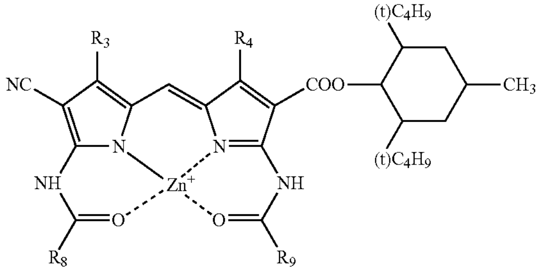
| | $R^3$ | $R^4$ | $R^8$ | $R^9$ |
|---|---|---|---|---|
| D-12 | 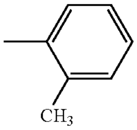 | $—CH_3$ | $—(t)C_4H_9$ | 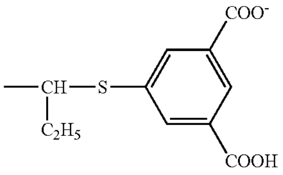 |
| D-13 | 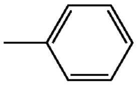 | Same as above | Same as above | 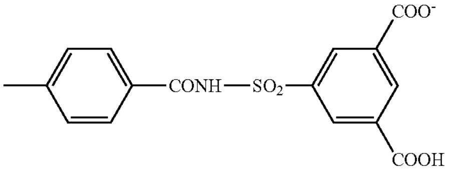 |
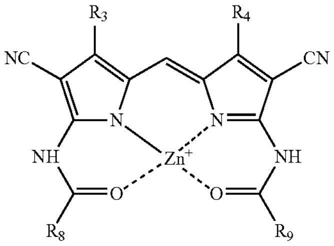
| | $R^3$ | $R^4$ | $R^8$ | $R^9$ |
|---|---|---|---|---|
| E-1 | 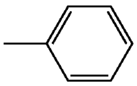 | 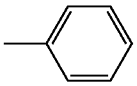 | $—(t)C_4H_9$ | 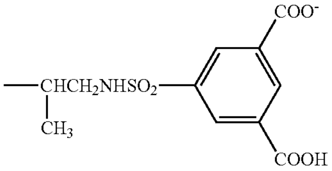 |
| E-2 | Same as above | Same as above | Same as above | 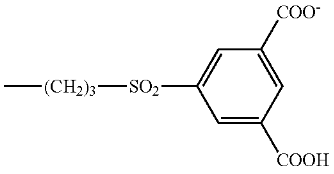 |
| E-3 | Same as above | Same as above | Same as above | 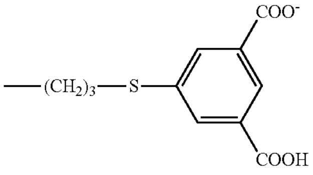 |

-continued
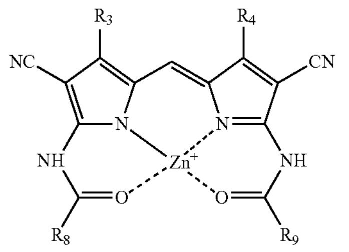
| | $R^3$ | $R^4$ | $R^8$ | $R^9$ |
|---|---|---|---|---|
| E-4 | Same as above | Same as above | 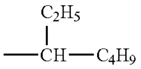 | Same as above |
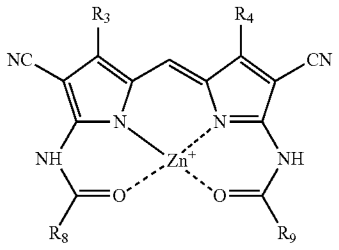
| | $R^3$ | $R^4$ | $R^8$ | $R^9$ |
|---|---|---|---|---|
| E-5 | 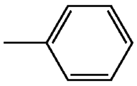 | 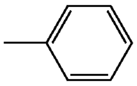 | 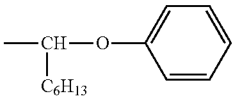 | 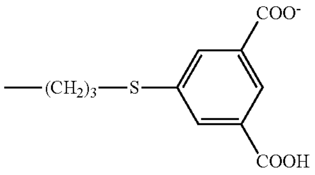 |
| E-6 | Same as above | Same as above | 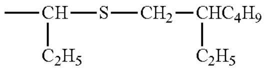 | Same as above |
| E-7 | Same as above | Same as above | 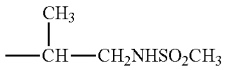 | Same as above |
| E-8 | Same as above | Same as above | 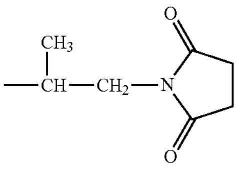 | Same as above |
| E-9 | Same as above | Same as above | 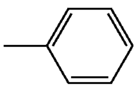 | Same as above |

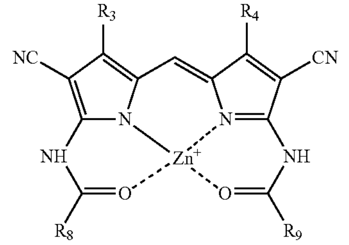
| | $R^3$ | $R^4$ | $R^8$ | $R^9$ |
|---|---|---|---|---|
| E-10 | 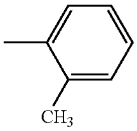 | 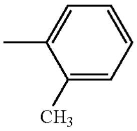 | 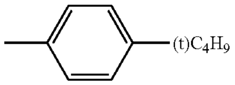 | 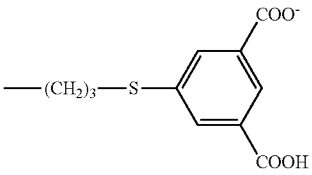 |
| E-11 | Same as above | Same as above | 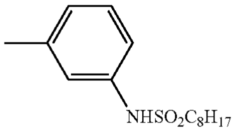 | Same as above |
| E-12 | Same as above | Same as above | 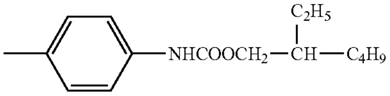 | Same as above |
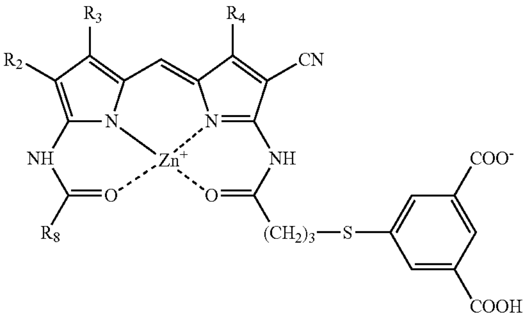
| | $R^2$ | $R^3$ | $R^4$ | $R^5$ | $R^8$ |
|---|---|---|---|---|---|
| F-1 | 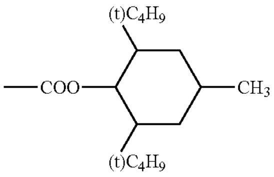 | $-CH_3$ | $-CH_3$ | $-SO_2CH_3$ | $-(t)C_4H_9$ |
| F-2 | Same as above | Same as above | Same as above | 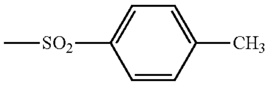 | Same as above |
| F-3 | Same as above | 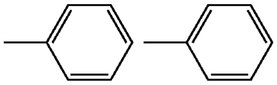 | | Same as above | Same as above |

-continued

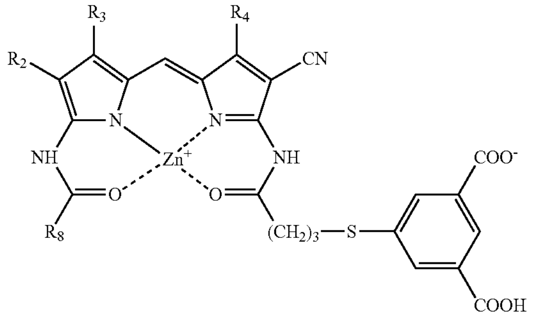

| | $R^2$ | $R^3$ | $R^4$ | $R^5$ | $R^8$ |
|---|---|---|---|---|---|
| F-4 | Same as above | Same as above | Same as above | Same as above | 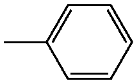 |

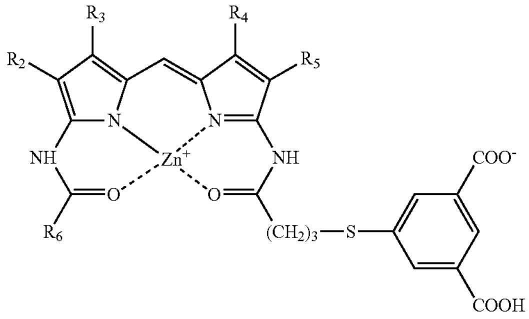

| | $R^2$ | $R^3$ | $R^4$ | $R^5$ | $R^8$ |
|---|---|---|---|---|---|
| F-5 | $—SO_2CH_3$ | 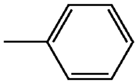 | 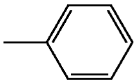 | 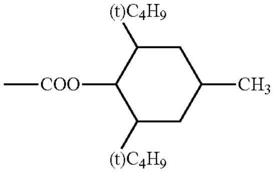 | 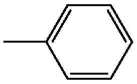 |
| F-6 | Same as above | Same as above | Same as above | Same as above | $—(t)C_4H_9$ |
| F-7 | Same as above | $—CH_3$ | $—CH_3$ | Same as above | Same as above |
| F-8 | 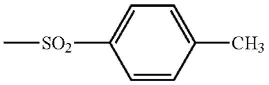 | Same as above | Same as above | Same as above | Same as above |
| F-9 | 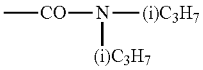 | 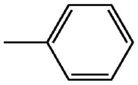 | 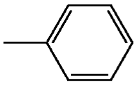 | Same as above | Same as above |
| F-10 | 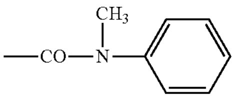 | Same as above | Same as above | Same as above | Same as above |

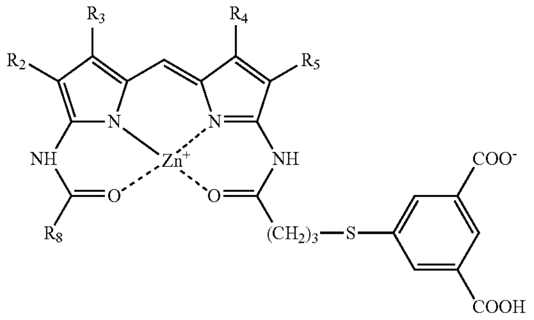
| | $R^2$ | $R^3$ | $R^4$ | $R^5$ | $R^8$ |
|---|---|---|---|---|---|
| F-11 | —$COOC_2H_5$ | 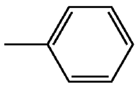 | 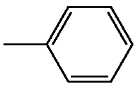 | 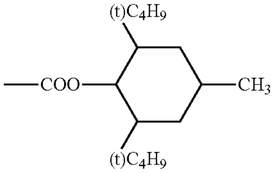 | —(t)$C_4H_9$ |
| F-12 | 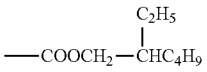 | Same as above | Same as above | Same as above | Same as above |
| F-13 | 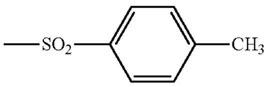 | Same as above | Same as above | Same as above | Same as above |
| F-14 | Same as above | Same as above | —$CH_3$ | Same as above | Same as above |
G-1
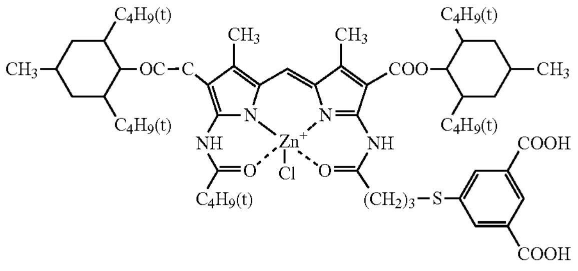
G-2
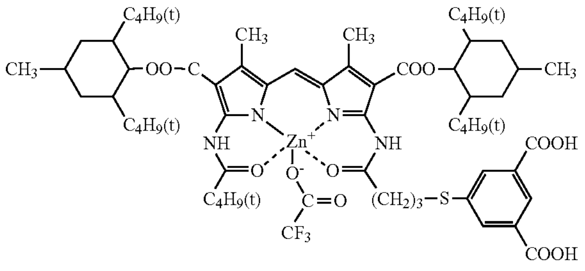
G-3
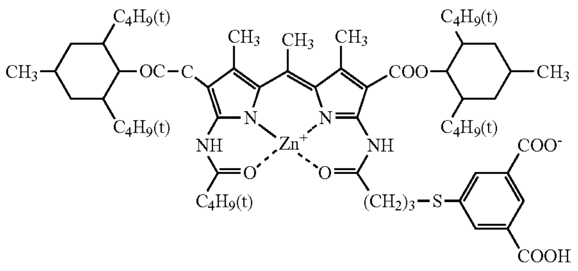
G-4
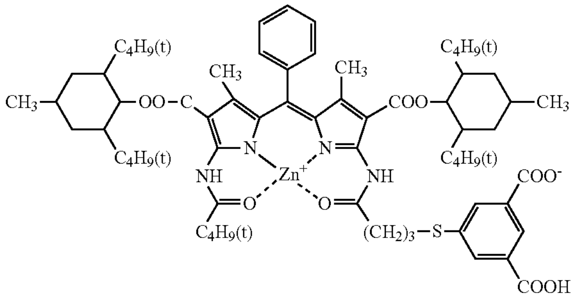

-continued
G-5
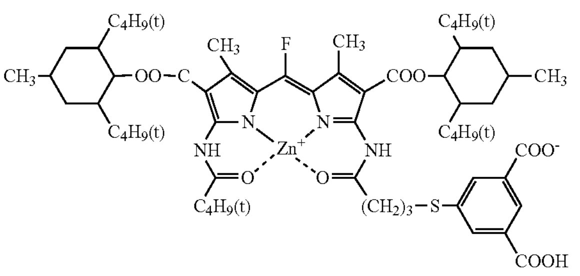
G-6
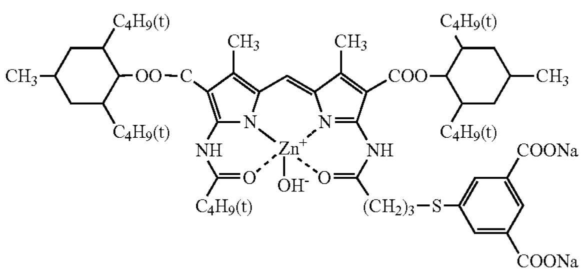
G-7
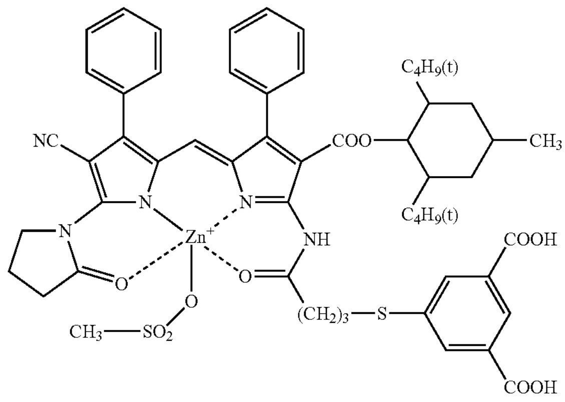
G-8
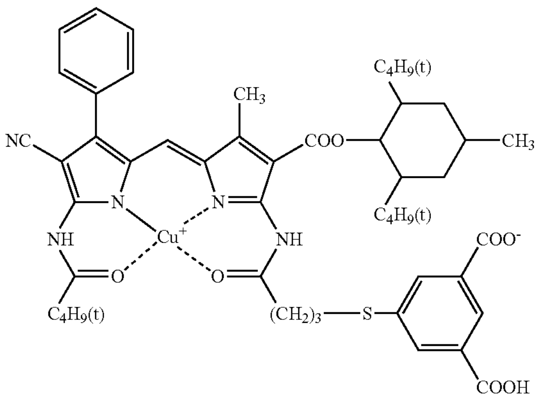
G-9
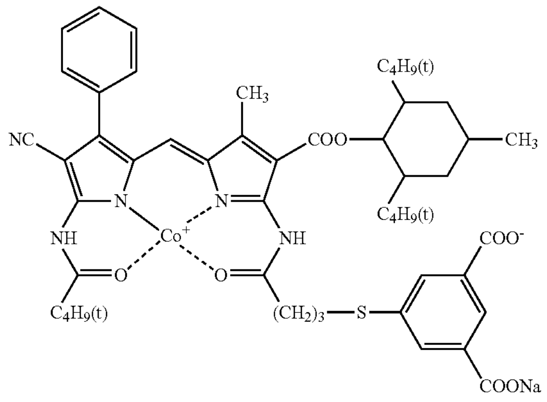
G-10
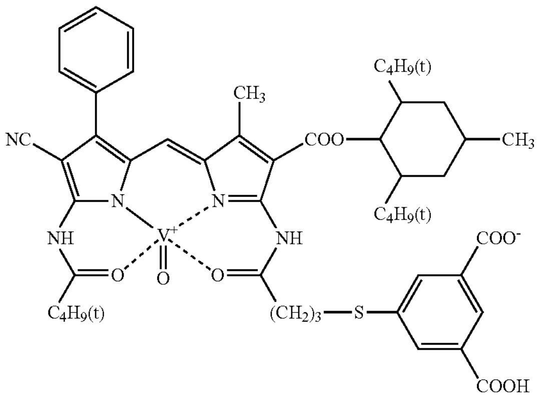
G-11
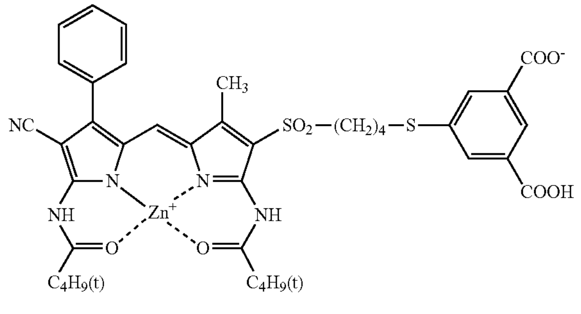
G-12
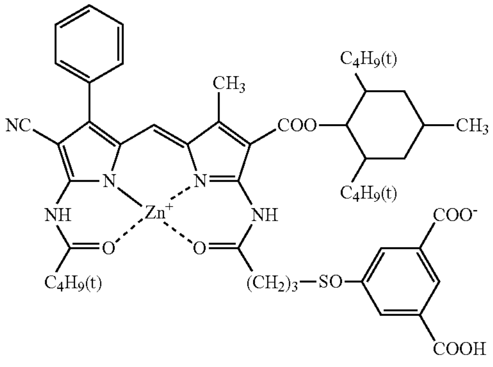

-continued
G-13
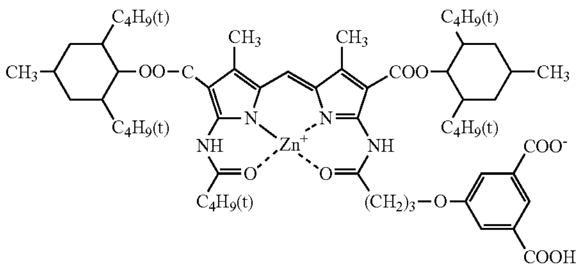
G-14
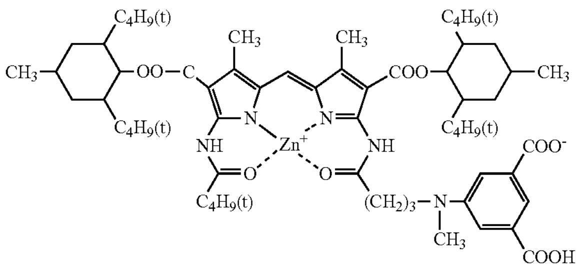
G-15
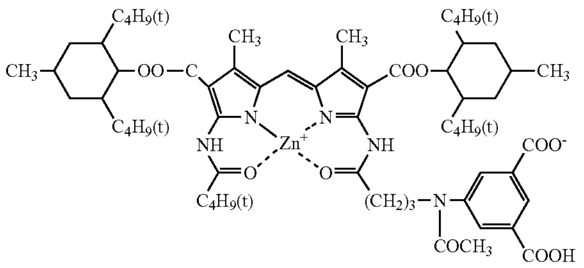
G-16
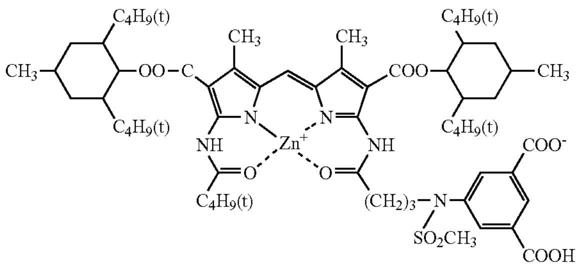
G-17
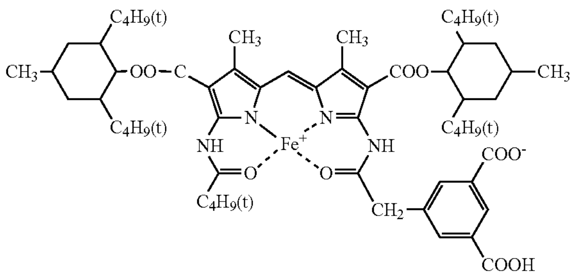
G-18
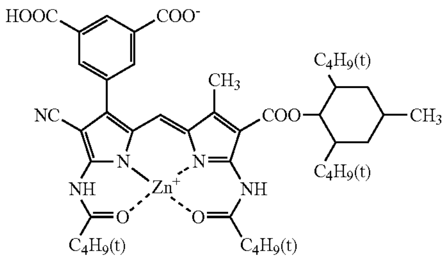
G-19
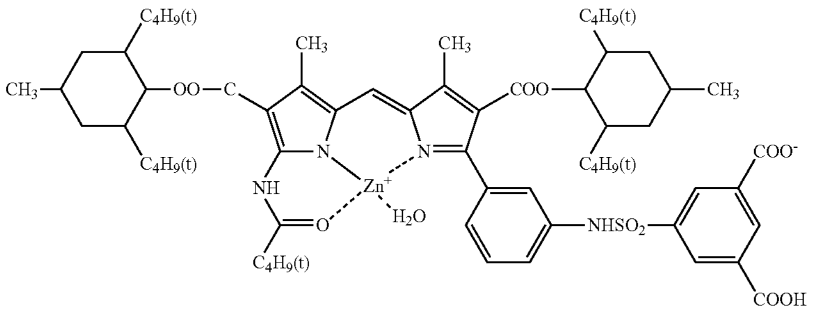
G-20
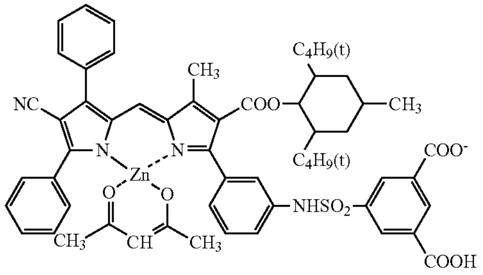
H-1
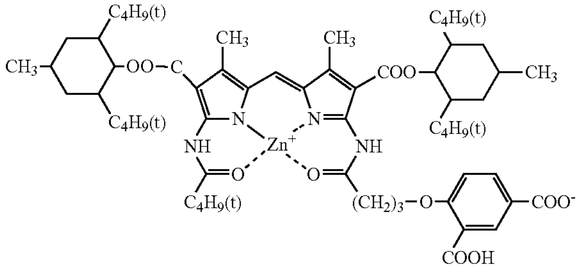

-continued
H-2
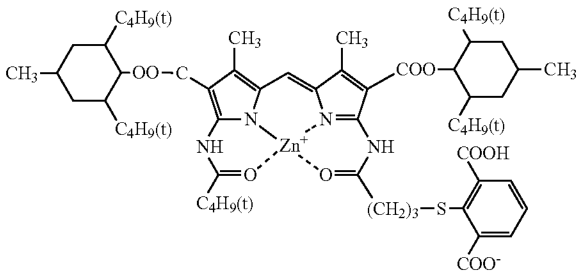
H-3
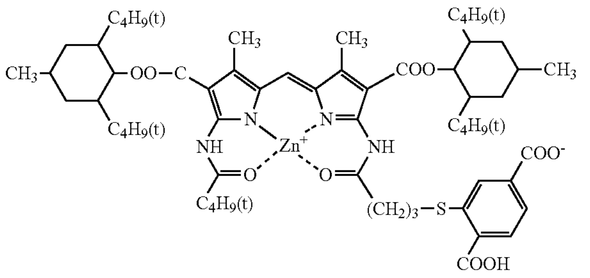
H-4
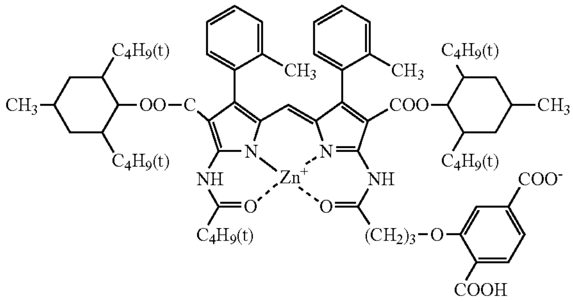
H-5
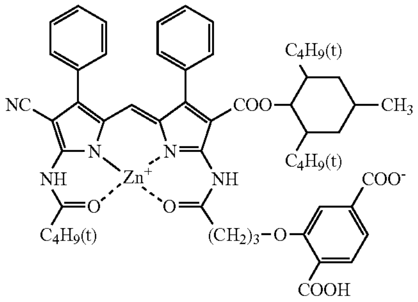
H-6
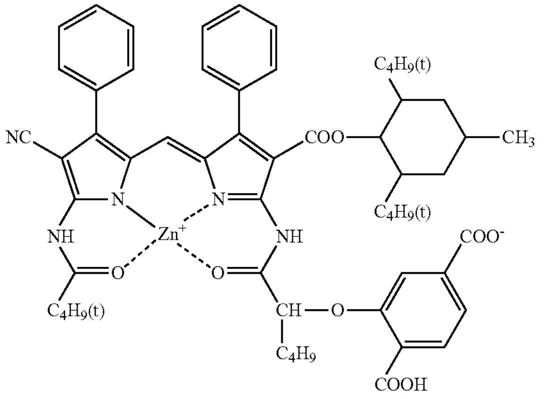
H-7
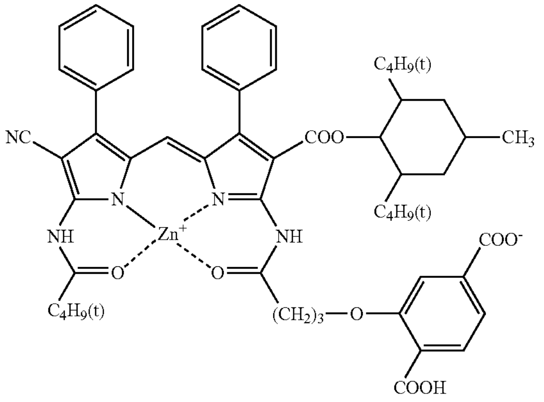
H-8
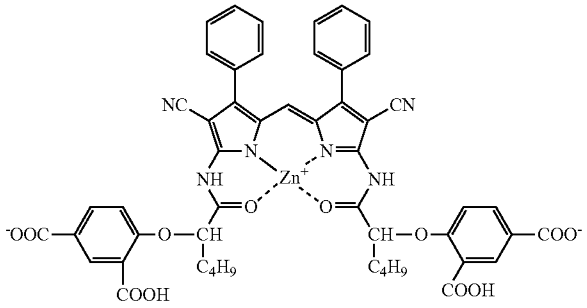
H-9
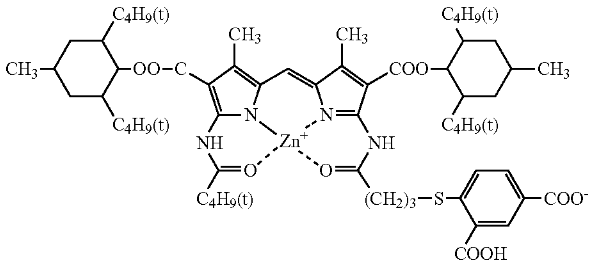

-continued
H-10
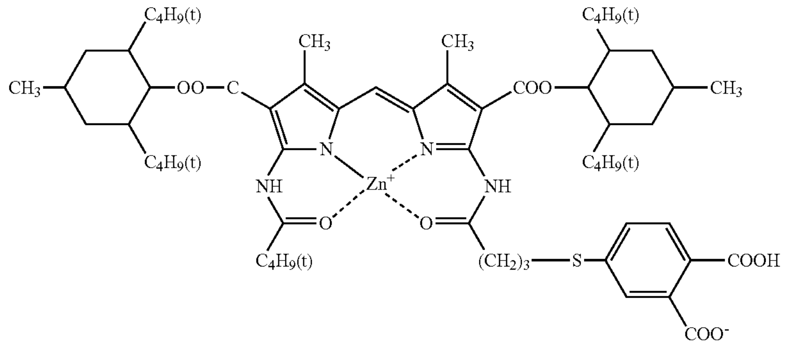
H-11
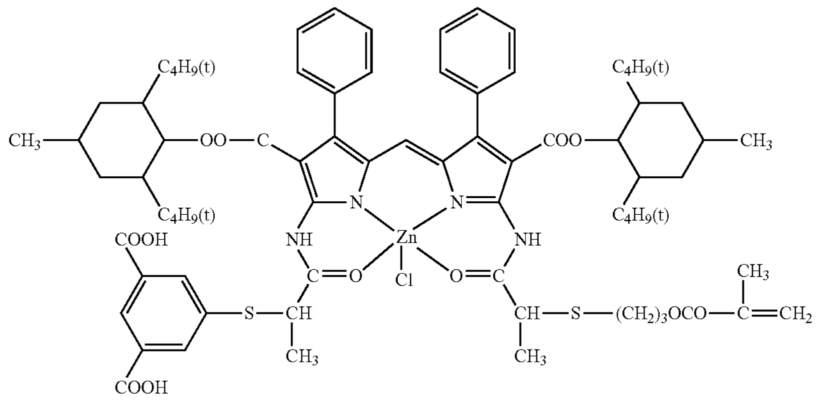
H-12
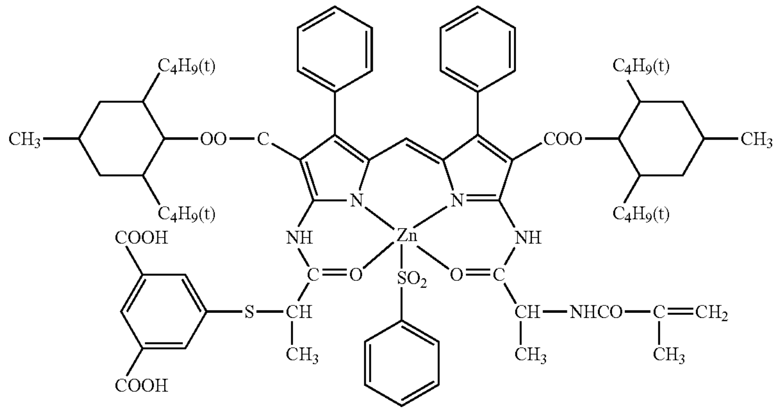
H-13
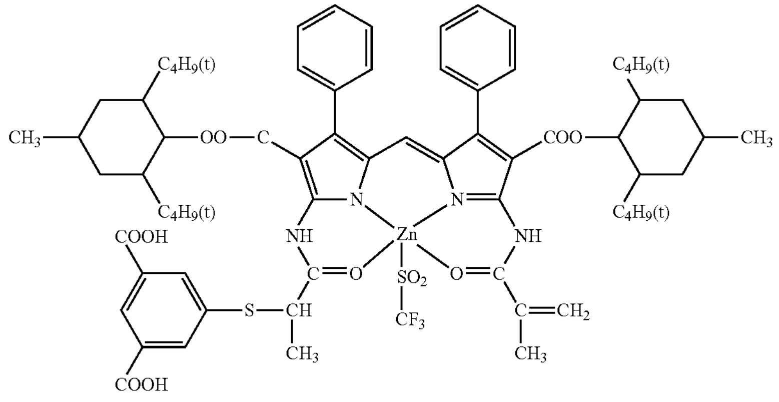

-continued

H-14

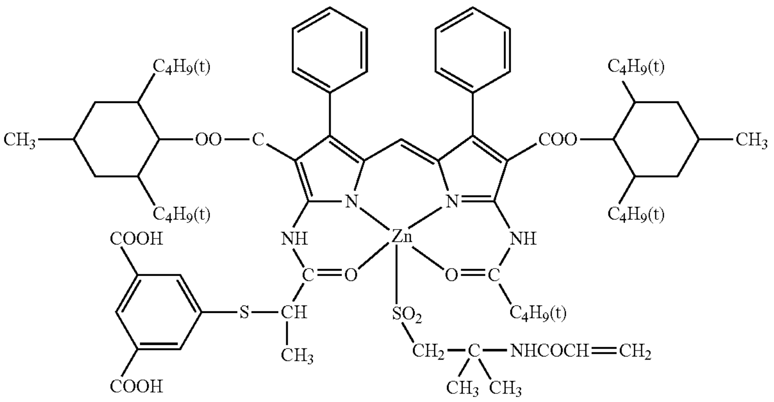

Compounds of Formula (A1), Formula (B1), Formula (C1), or Formula (D1) may be synthesized by the method described in US Application Publication No. 2008/0076044 A1.

The colored curable composition according to the first exemplary embodiment of the invention includes at least one compound selected from the compounds of Formula (A1) and Formula (B1) and tautomers thereof, and more preferably at least one compound selected from the compounds of Formula (C1) and Formula (D1) and tautomers thereof, and two or more of the compounds and tautomers may be used in combination.

The amount of at least one compound selected from the compounds of Formula (A1) and Formula (B1), which is included in the colored curable composition of the first exemplary embodiment of the invention, varies depending on a molecular weight and a molar absorption coefficient thereof, and is preferably from 0.5 to 80% by mass, more preferably from 0.5 to 60% by mass, and most preferably from 0.5 to 50% by mass, with respect to the total solid contents of the colored curable composition.

The colored curable composition according to the first exemplary embodiment of the invention and the color filter using the colored curable composition may include a phthalocyanine compound such as those disclosed in US Application Publication No. 2008/0076044 A1, a triarylmethane coloring agent having an absorption maximum at 550 to 650 nm such as C.I. Acid Blue 7, C.I. Acid Blue 83, C.I. Acid Blue 90, C.I. Solvent Blue 38, C.I. Acid Violet 17, C.I. Acid Violet 49 or C.I. Acid Green 3, in addition to the compounds of Formula (A1), Formula (B1), Formula (C1), and Formula (D1) and tautomers thereof.

Further, a xanthene colorant having an absorption maximum at 500 nm to 600 nm, for example, C. I. Acid. Red 289 may also be used.

The phthalocyanine coloring agent or the triarylmethane coloring agent may be used as long as the effect of the invention is not deteriorated, and the amount thereof is preferably from 0.5 to 50% by mass with respect to the total solid contents of the colored curable composition of the invention.

In order to manufacture a blue filter array, it is preferable that a mixture of a metal complex of the invention and at least one of the phthalocyanine coloring agents is used.

In this case, a proportion of them within the mixture varies depending on their molar absorption coefficients, spectrometric properties required, film thickness, and the like. Generally, the proportion (i.e., total amount of metal complex of the invention: phthalocyanine coloring agent) is from 10:1 to 1:20, and preferably in a range of from 5:1 to 1:10.

Colored Curable Composition of Second Exemplary Embodiment

The colored curable composition according to a second exemplary embodiment of the invention includes, as a coloring agent, at least one selected from the group consisting of a compound represented by Formula (A2), a compound represented by Formula (B2), and a tautomer thereof.

It is preferable that the colored curable composition according to the second exemplary embodiment of the invention is an ultraviolet-sensitive colored curable composition.

Formula (A2)

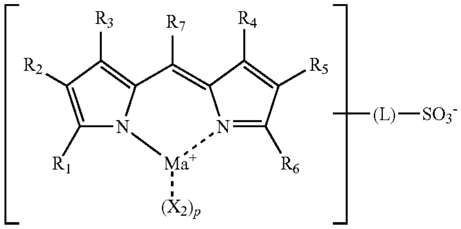

Formula (B2)

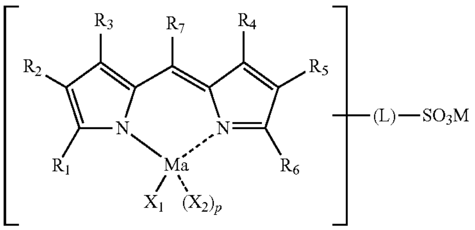

In Formula (A2) and Formula (B2), $R_1$ to $R_6$ each independently represent a hydrogen atom or a substituent, and $R_7$ represents a hydrogen atom, a halogen atom, an alkyl group, an aryl group, or a heterocyclic group, provided that any one of the substituents represented by $R_1$ to $R_6$ is a divalent linking group that binds to $-(L)-SO_3^-$ or $-(L)-SO_3M$. M represents a hydrogen atom, or an organic base or metal atom necessary for neutralizing a charge. L represents an alkylene group, an aralkylene group, or an arylene group, or a divalent group which may be formed by a combination of divalent groups selected from the group consisting of an alkylene group, an aralkylene group, an arylene group, —O—, —S—, —$SO_2$—, —N(Ra)—, —COO—, —OCO—, —CON(Rb)—, —N(Rb)CO—, —N(Rb)COO—, —OOCN(Rb)—, —N(Rb)CON(Rc)—, —$SO_2N$(Rb)—, and —N(Rb)$SO_2$—. Ra represents an alkyl group, an alkenyl group, an aryl group, a heterocyclic group, an acyl group, an alkylsulfonyl group, or an arylsulfonyl group; and Rb and Rc each independently represent a hydrogen atom, an alkyl group, an alkenyl group, an aryl group, or a heterocyclic group.

Ma represents a metal or a metal compound which may form a complex; $X_1$ represents a group necessary for neutralizing a charge; $X_2$ represents a group which may bind to Ma; and p represents 0 or 1. In Formula (B2), $X_1$ and $X_2$ may bind together to form a 5-membered, 6-membered, or 7-membered ring.

The compounds represented by Formula (A2) and Formula (B2), respectively, will be described in detail.

In a compound represented by Formula (A2) or Formula (B2), any one of the substituents represented by $R_1$ to $R_6$ is a divalent linking group that binds to -(L)-$SO_3^-$ or -(L)$SO_3$M, and explanation of any divalent group of $R_1$ to $R_6$ is expressed by substitution with a hydrogen atom for -(L)-$SO_3$—, and -(L)-$SO_3$M.

$R^1$ to $R^6$ in Formula (A2) or Formula (B2) each independently represents a hydrogen atom or a substituent. Examples of the substituent represented by any one of $R^1$ to $R^6$ include a halogen atom (for example, fluorine, chlorine, bromine), an alkyl group (for example, a straight, branched or cyclic alkyl group having preferably 1 to 48 carbon atoms, more preferably 1 to 24 carbon atoms; examples thereof include a methyl group, an ethyl group, a propyl group, an isopropyl group, a butyl group, a t-butyl group, a pentyl group, a hexyl group, a heptyl group, an octyl group, a 2-ethylhexyl group, a dodecyl group, a hexadecyl group, a cyclopropyl group, a cyclopentyl group, a cyclohexyl group, a 1-norbornyl group, and a 1-adamantyl group), an alkenyl group (for example, an alkenyl group having preferably 2 to 48 carbon atoms, more preferably 2 to 18 carbon atoms; examples thereof include a vinyl group, an allyl group, and a 3-buten-1-yl group), an aryl group (for example, an aryl group having preferably 6 to 48 carbon atoms, more preferably 6 to 24 carbon atoms; examples thereof include a phenyl group and a naphthyl group), a heterocyclic group (for example, a heterocyclic group having preferably 1 to 32 carbon atoms, more preferably 1 to 18 carbon atoms; examples thereof include a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group, and a benzotriazol-1-yl group), a silyl group (for example, a silyl group having preferably 3 to 38 carbon atoms, more preferably 3 to 18 carbon atoms; examples thereof include a trimethylsilyl group, a triethylsilyl group, a tributylsilyl group, a t-butyldimethylsilyl group, and a t-hexyldimethylsilyl group), a hydroxyl group, a cyano group, a nitro group, an alkoxy group (for example, an alkoxy group having preferably 1 to 48 carbon atoms, more preferably 1 to 24 carbon atoms; examples thereof include a methoxy group, an ethoxy group, a 1-butoxy group, a 2-butoxy group, an isopropoxy group, a t-butoxy group, a dodecyloxy group, and a cycloalkyloxy group such as a cyclopentyloxy group or a cyclohexyloxy group), an aryloxy group (for example, an aryloxy group having preferably 6 to 48 carbon atoms, more preferably 6 to 24 carbon atoms; examples thereof include a phenoxy group and a 1-naphthoxy group), a heterocyclic oxy group (for example, a heterocyclic oxy group having preferably 1 to 32 carbon atoms, more preferably 1 to 18 carbon atoms; examples thereof include a 1-phenyltetrazol-5-oxy group and a 2-tetrahydropyranyloxy group), a silyloxy group (for example, a silyloxy group having preferably 1 to 32 carbon atoms, more preferably 1 to 18 carbon atoms; examples thereof include a trimethylsilyloxy group, a t-butyldimethylsiliyloxy group, and a diphenylmethylsilyloxy group), an acyloxy group (for example, an acyloxy group having preferably 2 to 48 carbon atoms, more preferably 2 to 24 carbon atoms; examples thereof include an acetoxy group, a pivaloyloxy group, a benzoyloxy group, and a dodecanoyloxy group), an alkoxycarbonyloxy group (for example, an alkoxycarbonyloxy group having preferably 2 to 48 carbon atoms, more preferably 2 to 24 carbon atoms; examples thereof include an ethoxycarbonyloxy group, a t-butoxycarbonyloxy group, and a cycloalkyloxycarbonyloxy group such as a cyclohexyloxycarbonyloxy group), an aryloxycarbonyloxy group (for example, an aryloxycarbonyloxy group having preferably 7 to 32 carbon atoms, more preferably 7 to 24 carbon atoms; examples thereof include a phenoxycarbonyloxy group), a carbamoyloxy group (for example, a carbamoyloxy group having preferably 1 to 48 carbon atoms, more preferably 1 to 24 carbon atoms; examples thereof include a N,N-dimethylcarbamoyloxy group, a N-butylcarbamoyloxy group, N-phenylcarbamoyloxy group, and a N-ethyl-N-phenylcarbamoyloxy group), a sulfamoyloxy group (for example, a sulfamoyloxy group having preferably 1 to 32 carbon atoms, more preferably 1 to 24 carbon atoms; examples thereof include a N,N-diethylsulfamoyloxy group and a N-propylsulfamoyloxy group), an alkylsulfonyloxy group (for example, an alkylsulfonyloxy group having preferably 1 to 38 carbon atoms, more preferably 1 to 24 carbon atoms; examples thereof include a methylsulfonyloxy group, a hexadecylsulfonyloxy group, and a cyclohexylsulfonyloxy group), an arylsulfonyloxy group (for example, an arylsulfonyloxy group having preferably 6 to 32 carbon atoms, more preferably 6 to 24 carbon atoms; examples thereof include a phenylsulfonyloxy group), an acyl group (for example, an acyl group having preferably 1 to 48 carbon atoms, more preferably 1 to 24 carbon atoms; examples thereof include a formyl group, an acetyl group, a pivaloyl group, a benzoyl group, a tetradecanoyl group, and a cyclohexanoyl group), an alkoxycarbonyl group (for example, an alkoxycarbonyl group having preferably 2 to 48 carbon atoms, more preferably 2 to 24 carbon atoms; examples thereof include a methoxycarbonyl group, an ethoxycarbonyl group, an octadecyloxycarbonyl group, a cyclohexyloxycarbonyl group, and a 2,6-di-tert-butyl-4-methylcyclohexyloxycarbonyl group), an aryloxycarbonyl group (for example, an aryloxycarbonyl group having preferably 7 to 32 carbon atoms, more preferably 7 to 24 carbon atoms; examples thereof include a phenoxycarbonyl group), a carbamoyl group (for example, a carbamoyl group having preferably 1 to 48 carbon atoms, more preferably 1 to 24 carbon atoms; examples thereof include a carbamoyl group, a N,N-diethylcarbamoyl group, a N-ethyl-N-octylcarbamoyl group, a N,N-dibutylcarbamoyl group, a N-propylcarbamoyl group, a N-phenylcarbamoyl group, a N-methyl-N-phenylcarbamoyl group, and a N,N-dicyclohexylcarbamoyl group), an amino group (for example, an amino group having preferably 32 or less carbon atoms, more preferably 24 or less carbon atoms; examples thereof include an amino group, a methylamino group, a N,N-dibutylamino group, a tetradecylamino group, a 2-ethylhexylamino group, and a cyclohexylamino group), an anilino group (for example, an anilino group having preferably 6 to 32 carbon atoms, more preferably 6 to 24 carbon atoms; examples thereof include an anilino group and a N-methylanilino group), a heterocyclic amino group (for example, a heterocyclic amino group having preferably 1 to 32 carbon atoms, more preferably 1 to 18 carbon atoms; examples thereof include a 4-pyridyl amino group), a carbonamido group (for example, a carbonamido group having preferably 2 to 48 carbon atoms, more preferably 2 to 24 carbon atoms; examples thereof include an acetamide group, a benzamide group, a tetradecaneamido group, a pivaloylamido group, and a cyclohexaneamido group), a ureido group (for example, a ureido group having preferably 1 to 32 carbon atoms, more preferably 1 to 24 carbon atoms; examples thereof include a ureido group, a N,N-dimethylureido group, and a N-phenylureido group), an imido group (for example, an imido group having preferably 36 or less carbon atoms, more preferably 24 or less carbon atoms; examples thereof include a N-succinimido group and a N-phthalimido group), an alkoxycarbonylamino group (for example, an alkoxycarbonylamino group having preferably 2 to 48 carbon atoms, more preferably 2 to 24 carbon atoms; examples thereof include a methoxycarbonylamino group, an ethoxycarbonylamino group, a t-butoxycarbonylamino group, an octadecyloxycarbonylamino group, and a cyclohexyloxycarbonylamino group), an aryloxycarbonylamino group (for example, an aryloxycarbonylamino group having preferably 7 to 32 carbon atoms, more preferably 7 to 24 carbon atoms; examples thereof include a phenoxycarbonylamino group), a sulfonamido group (for example, a sulfonamido group having preferably 1 to 48 carbon atoms, more preferably 1 to 24 carbon atoms; examples thereof include a methanesulfonamido group, a butanesulfonamido group, a benzenesulfonamido group, a hexadecanesulfonamido group, and a cyclohexanesulfonamido group), a sulfamoylamino group (for example, a sulfamoylamino group having preferably 1 to 48 carbon atoms, more preferably 1 to 24 carbon atoms; examples thereof include a N,N-dipropylsulfamoylamino group and a N-ethyl-N-dodecylsulfamoylamino group), an azo group (for example, an azo group having preferably 1 to 32 carbon atoms, more preferably 1 to 24 carbon atoms; examples thereof include a phenylazo group and a 3-pyrazolylazo group), an alkylthio group (for example, an alkylthio group having preferably 1 to 48 carbon atoms, more preferably 1 to 24 carbon atoms; examples thereof include a methylthio group, an ethylthio group, an octylthio group, and a cyclohexylthio group), an arylthio group (for example, an arylthio group having preferably 6 to 48 carbon atoms, more preferably 6 to 24 carbon atoms; examples thereof include a phenylthio group), a heterocyclic thio group (for example, a heterocyclic thio group having preferably 1 to 32 carbon atoms, more preferably 1 to 18 carbon atoms; examples thereof include a 2-benzothiazolylthio group, a 2-pyridylthio group, and a 1-phenyltetrazolylthio group), an alkylsulfinyl group (for example, an alkylsulfinyl group having preferably 1 to 32 carbon atoms, more preferably 1 to 24 carbon atoms; examples thereof include a dodecanesulfinyl group), an arylsulfinyl group (for example, an arylsulfinyl group having preferably 6 to 32 carbon atoms, more preferably 6 to 24 carbon atoms; examples thereof include a phenylsulfinyl group), an alkylsulfonyl group (for example, an alkylsulfonyl group having preferably 1 to 48 carbon atoms, more preferably 1 to 24 carbon atoms; examples thereof include a methylsulfonyl group, an ethylsulfonyl group, a propylsulfonyl group, a butylsulfonyl group, an isopropylsulfonyl group, a 2-ethylhexylsulfonyl group, a hexadecylsulfonyl group, an octylsulfonyl group, and a cyclohexylsulfonyl group), an arylsulfonyl group (for example, an arylsulfonyl group having preferably 6 to 48 carbon atoms, more preferably 6 to 24 carbon atoms; examples thereof include a phenylsulfonyl group and a 1-naphthylsulfonyl group), a sulfamoyl group (for example, a sulfamoyl group having preferably 32 or less carbon atoms, more preferably 24 or less carbon atoms; examples thereof include a sulfamoyl group, a N,N-dipropylsulfamoyl group, a N-ethyl-N-dodecylsulfamoyl group, a N-ethyl-N-phenylsulfamoyl group, and a N-cyclohexylsulfamoyl group), a sulfo group, a phosphonyl group (for example, a phosphonyl group having preferably 1 to 32 carbon atoms, more preferably 1 to 24 carbon atoms; examples thereof include a phenoxyphosphonyl group, an octyloxyphosphonyl group, and a phenylphosphonyl group), a phosphinoylamino group (for example, a phosphinoylamino group having preferably 1 to 32 carbon atoms, more preferably 1 to 24 carbon atoms; examples thereof include a diethoxyphosphinoylamino group and a dioctyloxyphosphinoylamino group).

When the substituents represented by $R_1$ to $R_6$ in Formula (A2) or Formula (B2) may each further have at least one additional substituent, the additional substituent may be any one of the substituents represented by $R_1$ to $R_6$. When the substituents represented by $R_1$ to $R_6$ in Formula (A2) or Formula (B2) is each substituted with two or more additional substituents, the additional substituents may be the same as or different from each other, provided that any one of the substituents represented by $R_1$ to $R_6$ is a divalent linking group that binds to -(L)-$SO_3^-$ or -(L)-$SO_3$M.

When any one of the substituents represented by $R_1$ to $R_6$ is a divalent linking group, the divalent linking group may be a new divalent linking group formed by binding at least two substituents. For example, the new divalent linking group may be formed by binding at least two divalent linking groups selected from the group consisting of an alkylene group, an aralkylene group, an arylene group, a divalent heterocyclic group, —O—, —S—, —C(═O)O—, —OC(═O)—, —C(═O)—, —OC(═O)N(Rd)—, —C(═O)N(Rd)—, —N(Rd)C(═O)—, —N(Rd)C(═O)O—, —N(Rd)C(═O)N(Re)—, —C(═O)N(Rd)C(═O)—, —SO—, —$SO_2$—, —$SO_3$—, —$SO_2$N(Rd)—, —N(Rd)$SO_2$—, —C(═O)N(Rd)$SO_2$—, and —$SO_2$N(Rd)$SO_2$—.

Rd and Re each independently represent a hydrogen atom, an alkyl group, an aryl group, a heterocyclic group, an acyl group, an alkoxycarbonyl group, an alkylsulfonyl group, an arylsulfonyl group, a carbamoyl group, or a sulfamoyl group. These alkyl group, aryl group, heterocyclic group, acyl group, alkoxycarbonyl group, alkylsulfonyl group, arylsulfonyl group, carbamoyl group, and sulfamoyl group may each be substituted with an additional group which is any one of the substituents represented by $R_1$ to $R_6$, and when they are each substituted with 2 or more substituents, the additional substituents may be the same as or different from each other.

$R_7$ in Formula (A2) or Formula (B2) represents a hydrogen atom, a halogen atom, an alkyl group, an aryl group, or a heterocyclic group. The halogen group, the alkyl group, the aryl group, and the heterocyclic group of $R_7$ have the same meanings as the halogen atom, the alkyl group, the aryl group, and the heterocyclic group represented by any of $R_1$ to $R_6$, and the preferable ranges and examples thereof are also the same.

M in Formula (A2) or Formula (B2) represents a hydrogen atom, or an organic base or metal atom necessary for neutralizing a charge. Examples of the organic base include alkylamines, anilines, quaternary amines, guanidines, pyridines, and quinolines. Examples of the metal atom include alkali metal atoms. As M in Formula (A2) or Formula (B2), ammonia is also preferable. M is most preferably a hydrogen atom.

L in Formula (A2) or Formula (B2) represents an alkylene group, an aralkylene group, or an arylene group, or a divalent group which may be formed by a combination of divalent groups selected from the group consisting of an alkylene group, an aralkylene group, an arylene group, —O—, —S—, —$SO_2$—, —N(Ra)—, —COO—, —OCO—, —CON(Rb)—, —N(Rb)CO—, —N(Rb)COO—, —OOCN(Rb)—, —N(Rb)CON(Rc)—, —$SO_2$N(Rb)—, and —N(Rb)$SO_2$—. Ra represents an alkyl group, an alkenyl group, an aryl group, a heterocyclic group, an acyl group, an alkylsulfonyl group, or an arylsulfonyl group, and Rb and Rc each independently represent a hydrogen atom, an alkyl group, an alkenyl group, an aryl group, or a heterocyclic group.

The alkylene group represented by L is a straight, branched or cyclic alkylene group having preferably 1 to 18 carbon atoms, more preferably 1 to 12 carbon atoms, and examples thereof include a methylene group, an ethylene group, a propylene group, a butylene group, a cyclopropylene group, a cyclobutylene group, and a cyclohexylene group. The aralkylene group represented by L is an aralkylene group having preferably 7 to 18 carbon atoms, more preferably 7 to 16 carbon atoms, and examples thereof include a benzylene group and a phenethylene group. The arylene group represented by L is an arylene group having preferably 6 to 18 carbon atoms, more preferably 6 to 12 carbon atoms, and examples thereof include an o-phenylene group, a m-phenylene group, a p-phenylene group, and a 1,4-naphthylene group.

When the alkylene group, aralkylene group, or arylene group represented by L further has at least one additional substituent, the additional substituent may be any one of the substituents represented by $R_1$ to $R_6$, and when it is substituted with two or more additional substituents, the additional substituents may be the same as or different from each other.

L may be a divalent group formed by a combination of divalent groups selected from the group consisting of an alkylene group, an aralkylene group, an arylene group, —O—, —S—, —$SO_2$—, —N(Ra)-, —COO—, —OCO—, —CON(Rb)-, —N(Rb)CO—, —N(Rb)COO—, OOCN(Rb)-, —N(Rb)CON(Rc)-, —$SO_2$N(Rb)-, and —N(Rb)$SO_2$—. However, —O—, —S—, —$SO_2$—, —N(Ra)-, —COO—, —OCO—, —CON(Rb)-, —N(Rb)CO—, —N(Rb)COO—, —OOCN(Rb)-, —N(Rb)CON(Rc)-, —$SO_2$N(Rb)-, or —N(Rb)$SO_2$— does not directly bind to a —$SO_3^-$ or —$SO_3$M group, and —$SO_3^-$ or —$SO_3$M binds via the alkylene group, the aralkylene group, or the arylene group.

The alkyl group, the alkenyl group, the aryl group, the heterocyclic group, the acyl group, the alkylsulfonyl group, and the arylsulfonyl group represented by Ra have the same meanings as the alkyl group, the alkenyl group, the aryl group, the heterocyclic group, the acyl group, the alkylsulfonyl group, and the arylsulfonyl group represented by each of $R_1$ to $R_6$, and the preferable ranges and examples thereof are also the same.

When the alkyl group, the alkenyl group, the aryl group, the heterocyclic group, the acyl group, the alkylsulfonyl group, and the arylsulfonyl group represented by Ra each have at least one additional substituent, the additional substituent may be any one of the substituents represented by $R_1$ to $R_6$, and when they each are substituted with two or more additional substituents, the additional substituents may be the same as or different from each other.

The alkyl group, the alkenyl group, the aryl group, and the heterocyclic group represented by Rb have the same meanings as the alkyl group, the alkenyl group, the aryl group, and the heterocyclic group represented by $R_1$ to $R_6$, and the preferable ranges and examples thereof are also the same.

When the alkyl group, the alkenyl group, the aryl group, or the heterocyclic group represented by Rb has at least one additional substituent, the additional substituent may be any one of the substituents represented by $R_1$ to $R_6$, and when it is substituted with two or more additional substituents, the additional substituents may be the same as or different from each other.

Ma in Formula (A2) or Formula (B2) represents a metal or a metal compound which may form a complex. Examples of the metal and metal compound represented by Ma include divalent metal atoms, divalent metal oxides, divalent metal hydroxides, and divalent metal chlorides. For example, Ma may be any one of Zn, Mg, Si, Sn, Rh, Pt, Pd, Mo, Mn, Pb, Cu, Ni, Co, and Fe, a metal chloride such as AlCl, InCl, FeCl, $TiCl_2$, $SnCl_2$, $SiCl_2$, or $GeCl_2$, a metal oxide such as TiO or VO, or a metal hydroxide such as $Si(OH)_2$.

Among them, from the viewpoints of stability, spectrometric property, heat resistance, light resistance, and production suitability of the complex, Fe, Zn, Mg, Si, Pt, Pd, Mo, Mn, Cu, Ni, Co, TiO, or VO is preferable, Fe, Zn, Mg, Si, Pt, Pd, Cu, Ni, Co, or VO is more preferable, Fe, Zn, Co, or Cu is further preferable, and Zn is most preferable.

In Formula (A2) or Formula (B2), $X_1$ represents a group necessary for neutralizing a charge; $X_2$ represents a group which may bind to Ma; and p represents 0 or 1. $X_1$ and $X_2$ may bind together to form a 5-membered, 6-membered, or 7-membered ring.

$X_1$ in Formula (B2) represents a group necessary for neutralizing a charge, and examples thereof include a halogen, a hydroxy group, a carboxylic acid group, a phosphoric acid group, and a sulfonic acid group.

$X_2$ in Formula (A2) or Formula (B2) may be any group as long as it is a group which may bind to Ma, and examples thereof include water, alcohols (e.g. methanol, ethanol, propanol), and compounds described in "Metal Chelate" [1] Takeichi Sakaguchi, Keihei Ueno (1995, Nankodo Co., Ltd.), [2] (1996), and [3] (1997).

In Formula (A2) or Formula (B2), p represents 0 or 1.

$X_1$ and $X_2$ in Formula (A2) or Formula (B2) may bind to each other to form a 5-membered, 6-membered, or 7-membered ring with Ma. The 5-membered, 6-membered, or 7-membered ring may be a saturated or unsaturated ring. The 5-membered, 6-membered or 7-membered ring may contain only carbon atoms or may be a heterocyclic ring having at least one atom selected from nitrogen, oxygen and sulfur atoms.

From the viewpoints of synthesis suitability, and stability and fastness of a compound, the compound represented by Formula (A2) or Formula (B2), or the tautomer thereof is preferably a dipyrromethene metal complex represented by Formula (1-A2) or Formula (1-B2), or a tautomer thereof.

Formula (1-A2)

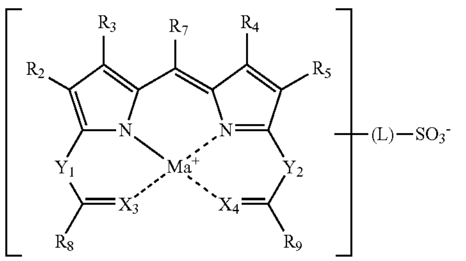

Formula (1-B2)

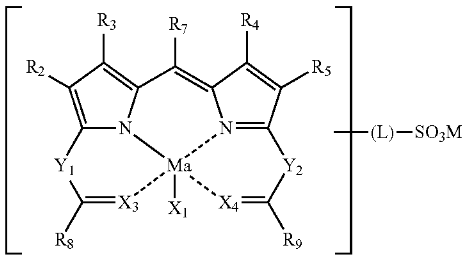

In Formulas (1-A2) and (1-B2), $R_2$ to $R_5$ each independently represent a hydrogen atom or a substituent; $R_7$ represents a hydrogen atom, a halogen atom, an alkyl group, an aryl group, or a heterocyclic group; and $R_8$ and $R_9$ each independently represent an alkyl group, an alkenyl group, an aryl group, a heterocyclic group, an alkoxy group, an aryloxy group, an amino group, an anilino group or a heterocyclic amino group; provided that any one of the substituents represented by $R_2$ to $R_5$, $R_8$ and $R_9$ is a divalent linking group to bind to -(L)-$SO_3^-$ or -(L)-$SO_3M$. M represents a hydrogen atom, or an organic base or metal atom necessary for neutralizing a charge. L represents an alkylene group, an aralkylene group, or an arylene group, or a divalent group which may be formed by a combination of divalent groups selected from the group consisting of an alkylene group, an aralkylene group, an arylene group, —O—, —S—, —$SO_2$—, —N(Ra)—, —COO—, —OCO—, —CON(Rb)—, —N(Rb)CO—, —N(Rb)COO—, —OOCN(Rb)—, —N(Rb)CON(Rc)—, —$SO_2$N(Rb)—, and —N(Rb)$SO_2$—. Ra represents an alkyl group, an alkenyl group, an aryl group, a heterocyclic group, an acyl group, an alkylsulfonyl group, or an arylsulfonyl group, and Rb and Rc each independently represent a hydrogen atom, an alkyl group, an alkenyl group, an aryl group, or a heterocyclic group.

Ma represents a metal or metal compound which may form a complex, and $X_1$ represents a group necessary for neutralizing a charge of Ma. $X_3$ and $X_4$ each independently represent NR (in which R represents a hydrogen atom, an alkyl group, an alkenyl group, an aryl group, a heterocyclic group, an acyl group, an alkylsulfonyl group, or an arylsulfonyl group; R and $R_8$ or $R_9$ may bind together to form a 5-membered, 6-membered, or 7-membered ring), an oxygen atom, or a sulfur atom; $Y_1$ and $Y_2$ each independently represent NR (in which R represents a hydrogen atom, an alkyl group, an alkenyl group, an aryl group, a heterocyclic group, an acyl group, an alkylsulfonyl group, or an arylsulfonyl group) or an oxygen atom; $R_8$ and $Y_1$ may bind together to form a 5-membered, 6-membered, or 7-membered ring; and $R_9$ and $Y_2$ may bind together to form a 5-membered, 6-membered, or 7-membered ring.

Next, Formula (1-A2) and Formula (1-B2) will be described in detail.

$R_2$ to $R_5$, $R_7$, M, L, Ma, and $X_1$ of Formula (1-A2) and Formula (1-B2) have the same meanings as those of Formula (A2) and Formula (B2), and the preferable ranges and examples thereof are also the same.

When any one of $R_8$ and $R_9$ in Formula (1-A2) or Formula (1-B2) is a divalent linking group that binds to -(L)-$SO_3^-$ or -(L)-$SO_3M$, the divalent linking group of $R_8$ or $R_9$ will be explained by substitution with a hydrogen atom for -(L)-$SO_3^-$ or -(L)-$SO_3M$.

$R_8$ and $R_9$ in Formula (1-A2) and Formula (1-B2) each independently represent an alkyl group, an alkenyl group, an aryl group, a heterocyclic group, an alkoxy group, an aryloxy group, an amino group, an anilino group, or a heterocyclic amino group.

The preferable ranges and examples of the alkyl group, the alkenyl group, the aryl group, the heterocyclic group, the alkoxy group, the aryloxy group, the amino group, the anilino group, and the heterocyclic amino group represented by each of $R_8$ and $R_9$ are the same as those of $R_1$ to $R_6$.

The alkyl group, the alkenyl group, the aryl group, the heterocyclic group, the alkoxy group, the aryloxy group, the amino group, the anilino group, and the heterocyclic amino group represented by $R_8$ and $R_9$ may each further have at least one additional substituent which is any one of the substituents represented by $R_1$ to $R_6$, and when they are substituted with two or more additional substituents, the additional substituents may be the same as or different from each other.

When any one of the substituents represented by $R_8$ and $R_9$ is a divalent linking group, the divalent linking group may be a new divalent linking group formed by binding at least two substituents. For example, the new divalent linking group may be formed by binding at least two divalent linking groups selected from the group consisting of an alkylene group, an aralkylene group, an arylene group, a divalent heterocyclic group, —O—, —S—, —C(═O)O—, —OC(═O)—, —C(═O)—, —OC(═O)N(Rd)—, —C(═O)N(Rd)—, —N(Rd)C(═O)—, —N(Rd)C(═O)O—, —N(Rd)C(═O)N(Re)—, —SO—, —$SO_2$—, —$SO_3$—, —$SO_2$N(Rd)—, —N(Rd)$SO_2$—, —C(═O)N(Rd)$SO_2$—, and —$SO_2$N(Rd)$SO_2$—.

Rd and Re each independently represent a hydrogen atom, an alkyl group, an aryl group, a heterocyclic group, an acyl group, an alkoxycarbonyl group, an alkylsulfonyl group, an arylsulfonyl group, a carbamoyl group, or a sulfamoyl group. These alkyl group, aryl group, heterocyclic group, acyl group, alkoxycarbonyl group, alklysulfonyl group, arylsulfonyl group, carbamoyl group, and sulfamoyl group may be substituted with an additional group which is any one of the substituents represented by $R_1$ to $R_6$, and when they are each substituted with two or more additional substituents, the additional substituents may be the same as or different from each other.

$X_3$ and $X_4$ in Formula (1-A2) or Formula (1-B2) each independently represent NR (in which R represents a hydrogen atom, an alkyl group, an alkenyl group, an aryl group, a heterocyclic group, an acyl group, an alkylsulfonyl group, or an arylsulfonyl group; and R and $R_8$ or $R_9$ may be taken together to form a 5-membered, 6-membered, or 7-membered ring), an oxygen atom, or a sulfur atom. The preferable ranges and examples of the alkyl group, the alkenyl group, the aryl group, the heterocyclic group, the acyl group, the alkylsulfonyl group, and the arylsulfonyl group represented by R are the same as those of the alkyl group, the alkenyl group, the aryl group, the heterocyclic group, the acyl group, the alkylsulfonyl group, and the arylsulfonyl group represented by any of $R_1$ to $R_6$.

When R is substituted with at least one additional substituent, the additional substituent may be any one of the substituents represented by $R_1$ to $R_6$, and when it is substituted with two or more additional substituents, the additional substituents may be the same as or different from each other.

$X_3$ and $X_4$ each preferably represent NR (in which R is a hydrogen atom, an alkyl group, an aryl group, an alkylsulfonyl group, or an arylsulfonyl group) or an oxygen atom, and, from the viewpoints of synthesis suitability and stability of a compound, an oxygen atom is most preferable.

$Y_1$ and $Y_2$ in Formula (1-A2) or Formula (1-B2) each independently represent NR (in which R is a hydrogen atom, an alkyl group, an alkenyl group, an aryl group, a heterocyclic group, an acyl group, an alkylsulfonyl group, or an arylsulfonyl group) or an oxygen atom, and R in NR has the same meaning as that of R in NR as an example of $X_3$ and $X_4$.

In Formula (1-A2) or Formula (1-B2), $R_8$ and $Y_1$ may bind together to form a 5-membered, 6-membered, or 7-membered ring, and $R_9$ and $Y_2$ may bind together to form a 5-membered, 6-membered, or 7-membered ring.

Ma represents a metal or metal compound which may form a complex, and $X_1$ represents a group necessary for neutralizing a charge of Ma.

From the viewpoints of synthesis suitability, and stability, and solubility in an organic solvent of a compound, Formula (1-A2) is further preferably represented by the following Formula (C2) or a tautomer thereof, and Formula (1-B2) is further preferably represented by the following Formula (D2) or a tautomer thereof.

Formula (C2)

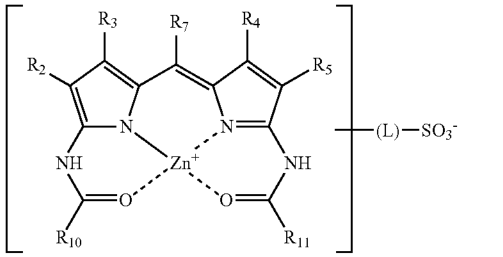

Formula (D2)

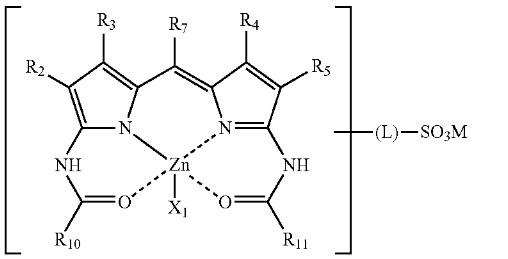

In Formula (C2) and Formula (D2), $R_2$ to $R_5$ each independently represent a hydrogen atom or a substituent; $R_7$ represents a hydrogen atom, a halogen atom, an alkyl group, an aryl group, or a heterocyclic group; and $R_{10}$ and $R_{11}$ each independently represent an alkyl group, an alkenyl group, an aryl group, a heterocyclic group, an alkoxy group, an aryloxy group, an amino group, an anilino group, or a heterocyclic amino group; provided that any one of the substituents represented by $R_2$ to $R_5$, $R_{10}$ and $R_{11}$ is a divalent linking group that binds to -(L)-$SO_3^-$ or -(L)-$SO_3M$. M represents a hydrogen atom, or an organic base or metal atom necessary for neutralizing a charge. L represents an alkylene group, an aralkylene group, or an arylene group, or a divalent group which may be formed by a combination of divalent groups selected from the group consisting of an alkylene group, an aralkylene group, an arylene group, —O—, —S—, —$SO_2$—, —N(Ra)—, —COO—, —OCO—, —CON(Rb)—, —N(Rb)CO—, —N(Rb)COO—, —OOCN(Rb)—, —N(Rb)CON(Rc)—, —$SO_2N$(Rb)—, and —N(Rb)$SO_2$—. Ra represents an alkyl group, an alkenyl group, an aryl group, a heterocyclic group, an acyl group, an alkylsulfonyl group, or an arylsulfonyl group, and Rb and Rc each independently represent a hydrogen atom, an alkyl group, an alkenyl group, an aryl group, or a heterocyclic group. $X_1$ represents a group necessary for neutralizing a charge of Zn.

$R_2$ to $R_5$, $R_7$, M, L, and $X_1$ in Formula (C2) or Formula (D2) have the same meanings as in Formula (A2), Formula (B2), Formula (1-A2), and Formula (1-B2), and the preferable ranges and examples thereof are also the same.

$R_{10}$ and $R_{11}$ each independently represent an alkyl group, an alkenyl group, an aryl group, a heterocyclic group, an alkoxy group, an aryloxy group, an amino group, an anilino group, or a heterocyclic amino group, provided that any one of the substituents represented by $R_2$ to $R_5$, $R_{10}$, and $R_{11}$ is a divalent linking group that binds to -(L)-$SO_3^-$ or -(L)-$SO_3M$.

When any one of $R_{10}$ and $R_{11}$ in Formula (C2) or Formula (D2) is a divalent linking group that binds to -(L)-$SO_3^-$ or -(L)-$SO_3M$, the divalent linking group represented by $R_{10}$ or $R_{11}$ is explained by substitution with a hydrogen atom for -(L)-$SO_3^-$ or -(L)-$SO_3M$.

$R_{10}$ and $R_{11}$ in Formula (C2) or Formula (D2) each independently represent an alkyl group, an alkenyl group, an aryl group, a heterocyclic group, an alkoxy group, an aryloxy group, an amino group, an anilino group, or a heterocyclic amino group.

The alkyl group, the alkenyl group, the aryl group, the heterocyclic group, the alkoxy group, the aryloxy group, the amino group, the anilino group, or the heterocyclic amino group represented by $R_{10}$ or $R_{11}$ may be further substituted with an additional substituent which is any one of the substituents represented by $R_1$ to $R_6$, and when it is substituted with two or more additional substituents, the additional substituents may be the same as or different from each other.

$R_{10}$ and $R_{11}$ each are preferably independently an alkyl group or an aryl group from the viewpoints of synthesis suitability and stability of a compound.

When any one of the substituents represented by $R_{10}$ and $R_{11}$ is a divalent linking group, the divalent linking group may be a new divalent linking group formed by binding at least two substituents. For example, the new divalent linking group may be formed by binding at least two divalent linking groups selected from the group consisting of an alkylene group, an aralkylene group, an arylene group, a divalent heterocyclic group, —O—, —S—, —C(═O)O—, —OC(═O)—, —C(═O)—, —OC(═O)N(Rd)—, —C(═O)N(Re)—, —N(Rd)C(═O)—, —N(Rd)C(═O)O—, —N(Rd)C(═O)N(Re)—, —SO—, —$SO_2$—, —$SO_3$—, —$SO_2N$(Rd)—, —N(Rd)$SO_2$—, —C(═O)N(Rd)$SO_2$—, and —$SO_2N$(Rd)$SO_2$—.

Rd and Re each independently represent a hydrogen atom, an alkyl group, an aryl group, a heterocyclic group, an acyl group, an alkoxycarbonyl group, an alkylsulfonyl group, an arylsulfonyl group, a carbamoyl group, or a sulfamoyl group. These alkyl group, aryl group, heterocyclic group, acyl group, alkoxycarbonyl group, alkylsulfonyl group, arylsulfonyl group, carbamoyl group, and sulfamoyl group may each be substituted with at least one additional substituent which is any one of the substituents of $R_1$ to $R_6$, and when they are substituted with two or more additional substituents, the additional substituents may be the same as or different from each other.

Tautomers of the compounds represented by Formula (1-A2), Formula (1-B2), Formula (C2), and Formula (D2), respectively, will be described.

Tautomers of compounds represented by Formula (1-A2), Formula (1-B2), Formula (C2), and Formula (D2), respectively, may be any tautomer as long as it is a compound having a structure which may be formed by movement of one hydrogen atom in the molecule of the compound. For example, the tautomers may have structures represented by the following Formula (a') to Formula (f').

Formula (a')

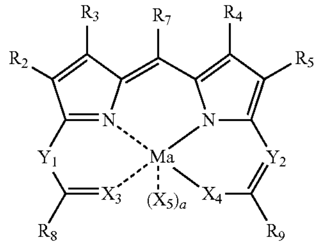

-continued

Formula (b')

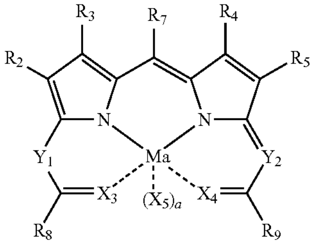

Formula (c')

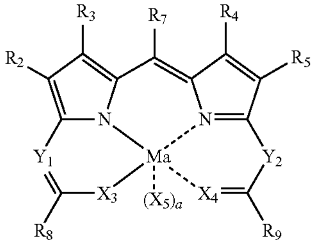

Formula (d')

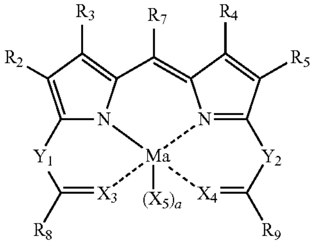

Formula (e')

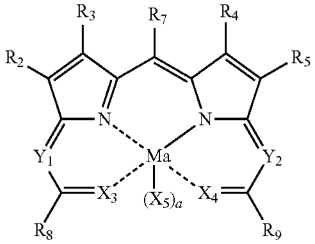

Formula (f')

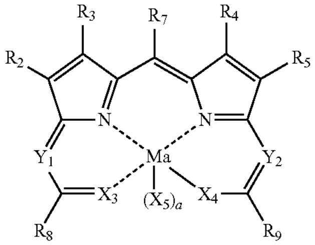

In Formulas (a') to (f'), $X_5$ is a group which may bind to Ma, and a is 0 or 1. Other substituents respectively have the same meanings as in Formula (1-A2), Formula (1-B2), Formula (C2), or Formula (D2).

Next, the preferable ranges and examples of the compounds of the invention will be described.

It is preferable that Formula (A2) is represented by Formula (1-A2), and Formula (B2) is represented by Formula (1-B2). It is more preferable that each Formula (A2) is represented by Formula (C2) and Formula (B2) is represented by Formula (D2).

L in Formula (1-A2), Formula (1-B2), Formula (C2), or Formula (D2) is preferably an alkylene group.

In Formula (A2) or Formula (B2), It is preferable that -(L)-$SO_3^-$ or -(L)-$SO_3M$ binds to a divalent linking group represented by $R_1$ or $R_6$. In Formula (1-A2) or Formula (1-B2), it is preferable that -(L)-$SO_3^-$ or -(L)-$SO_3M$ binds to a divalent linking group represented by $R_8$ or $R_9$. In Formula (C2) or Formula (D2), it is preferable that -(L)-$SO_3^-$ or -(L)-$SO_3M$ binds to a divalent linking group represented by $R_{10}$ or $R_{11}$.

When any one of $R_1$ to $R_6$ of Formula (A2) or Formula (B2) is a divalent linking group that binds to -(L)-$SO_3^-$ or -(L)-$SO_3M$, the divalent linking group is preferably an alkylene group, an aralkylene group, an arylene group, or a divalent heterocyclic group, or a divalent linking group formed by any one of an alkylene group, an aralkylene group, and an arylene group, and any one of —O—, —S—, —C(═O)O—, —OC(═O)—, —C(═O)—, —OC(═O)N(Rd)—, —C(═O)N(Re)—, —N(Rd)C(═O)—, —N(Rd)C(═O)O—, —N(Rd)C(═O)N(Re)—, —SO—, —$SO_2$—, —$SO_2$N(Rd)—, and —N(Rd)$SO_2$—. Further preferable is an alkylene group, an aralkylene group, or an arylene group.

When any one of $R_2$ to $R_5$, $R_8$, and $R_9$ in Formula (1-A2) or Formula (1-B2) is a divalent linking group that binds to -(L)-$SO_3^-$ or -(L)-$SO_3M$, the divalent linking group is preferably an alkylene group, an aralkylene group, an arylene group, or a divalent heterocyclic group, or a divalent linking group formed by any one of an alkylene group, an aralkylene group, and an arylene group, and any one of —O—, —S—, —C(═O)O—, —OC(═O)—, —C(═O)—, —OC(═O)N(Rd)-, —C(═O)N(Re)-, —N(Rd)C(═O)—, —N(Rd)C(═O)O—, —N(Rd)C(═O)N(Re)-, —SO—, —$SO_2$—, —$SO_2$N(Rd)-, and —N(Rd)$SO_2$—. An alkylene group, an aralkylene group, or an arylene group is more preferable.

When any one of $R_2$ to $R_5$, $R_{10}$, and $R_{11}$ in Formula (C2) or Formula (D2) is a divalent linking group that binds to -(L)-$SO_3^-$ or -(L)-$SO_3M$, the divalent linking group is preferably an alkylene group, an aralkylene group, an arylene group, or a divalent heterocyclic group, or a divalent linking group formed by any one of an alkylene group, an aralkylene group, and an arylene group, and any one of —O—, —S—, —C(═O)O—, —OC(═O)—, —C(═O)—, —OC(═O)N(Rd)—, —C(═O)N(Re)—, —N(Rd)C(═O)—, —N(Rd)C(═O)O—, —N(Rd)C(═O)N(Re)—, —SO—, —$SO_2$—, —$SO_2$N(Rd)—, and —N(Rd)$SO_2$—. Further preferable is an alkylene group, an aralkylene group, or an arylene group.

The preferable ranges of respective substituents of Formula (A1), Formula (B2), Formula (1-A2), Formula (1-B2), Formula (C2), and Formula (D2) will be described below; however, in a combination of a preferable range of each substituent with a preferable range of formulae, the respective more preferable ranges are more preferable.

$R_1$ and $R_6$ in Formula (A2) or Formula (B2) each are preferably independently an alkyl group, an aryl group, a heterocyclic group, a group represented by —$Y_1$—C(═$X_3$)—$R_8$ or a group represented by —$Y_2$—C(═$X_4$)$R_9$ shown in Formula (1-A2) or Formula (1-B2), or a group represented by —NH—C(═O)—$R_{10}$ or —NH—C(═O)—$R_{11}$ shown in Formula (C2) or Formula (D2).

More preferably, $R_1$ and $R_6$ are each a group represented by —$Y_1$—C(═$X_3$)—$R_8$ or a group represented by —$Y_2$—C(═$X_4$)—$R_9$ shown in Formula (1-A2) or Formula (1-B2), or a group represented by —NH—C(═O)—$R_{10}$ or —NH—C(═O)—$R_{11}$ shown in Formula (C2) or Formula (D2).

Most preferable is a group represented by —NH—C(═O)—$R_{10}$ or —NH—C(═O)—$R_{11}$ shown in Formula (C2) and Formula (D2).

$R_2$ and $R_5$ in Formula (A2), Formula (B2), Formula (1-A2), Formula (1-B2), Formula (C2), or Formula (D2) each are preferably independently an alkyl group, an aryl group, a heterocyclic group, an alkoxycarbonyl group, an aryloxycarbonyl group, a cyano group, a carboxyl group, an acyl group, a carbamoyl group, an alkylthio group, an arylthio group, a heterocyclic thio group, an alkylsulfonyl group, an arylsulfonyl group, a heterocyclic sulfonyl group, an alkylsulfinyl group, an arylsulfinyl group, or a sulfamoyl group; more preferably a perfluoroalkyl group, an aryl group, a heterocyclic group, an alkoxycarbonyl group, an aryloxycarbonyl group, a cyano group, a carboxyl group, an acyl group, a carbamoyl group, an alkylsulfonyl group, an arylsulfonyl group, a heterocyclic sulfonyl group, or a sulfamoyl group; further preferably a perfluoroalkyl group, an aryl group, a heterocyclic group, an alkoxycarbonyl group, an aryloxycarbonyl group, a cyano group, a carboxyl group, an acyl group, a carbamoyl group, an alkylsulfonyl group, an arylsulfonyl group, or a sulfamoyl group; and most preferably a perfluoroalkyl group, an alkoxycarbonyl group, an aryloxycarbonyl group, a cyano group, a carbamoyl group, an alkylsulfonyl group, or an arylsulfonyl group.

$R_3$ and $R_4$ in Formula (A2), Formula (B2), Formula (1-A2), Formula (1-B2), Formula (C2), or Formula (D2) are each preferably independently an alkyl group, an aryl group, a heterocyclic group, an alkoxycarbonyl group, a cyano group, or a carbamoyl group; more preferably an alkyl group, an aryl group, a heterocyclic group, or a cyano group; and most preferably an alkyl group, an aryl group, or a heterocyclic group.

$R_7$ in Formula (A2), Formula (B2), Formula (1-A2), Formula (1-B2), Formula (C2), or Formula (D2) is preferably a hydrogen atom, a halogen atom, an alkyl group, an aryl group, or a heterocyclic group; more preferably a hydrogen atom, an alkyl group, an aryl group, or a heterocyclic group; further preferably a hydrogen atom, an alkyl group, or an aryl group; and most preferably a hydrogen atom.

M in Formula (B2), Formula (1-B2), or Formula (D2) is preferably a hydrogen atom, a trialkylamine having 3 to 14 carbon atoms, a quaternary ammonium having 4 to 20 carbon atoms, a guanidine having 3 to 14 carbon atoms, or an alkali metal, more preferably a trialkylamine having 3 to 9 carbon atoms, a quaternary ammonium salt 4 to 8 carbon atoms, or an alkali metal, and further preferably an alkali metal.

$X_2$ in Formula (A2) or Formula (B2) is preferably water, alcohols (e.g. methanol, ethanol, propanol), or a compound described in "Metal Chelate" [1] Takeichi Sakaguchi/Keihei Ueno (1995, Nankodo Co., Ltd.), the same [2] (1996), and the same [3] (1997), and further preferably water or alcohols, and most preferably p is 0.

Ma in Formula (A2), Formula (B2), Formula (1-A2), or Formula (1-B2) is preferably Fe, Zn, Co, or Cu, further preferably Zn, Co, or Cu, and most preferably Zn.

$X_1$ in Formula (B2), Formula (1-B2), or Formula (D2) is preferably a halogen atom, a carboxylic acid group, a sulfonic acid group, or a phosphoric acid group, and more preferably a chlorine atom, a carboxylic acid group, or a sulfonic acid group.

$R_8$ and $R_9$ in Formula (1-A2) or Formula (1-B2) each are preferably independently an alkyl group, an alkenyl group, an aryl group, a heterocyclic group, an alkoxy group, an amino group, or an anilino group, more preferably an alkyl group, an aryl group, a heterocyclic group, an alkoxy group, an amino group, or an anilino group, further preferably an alkyl group, an aryl group, or a heterocyclic group, and most preferably an alkyl group or an aryl group.

$X_3$ and $X_4$ in Formula (1-A2) or Formula (1-B2) each are preferably independently NR (in which R represents a hydrogen atom, an alkyl group, an alkenyl group, an aryl group, a heterocyclic group, an acyl group, an alkylsulfonyl group, or an arylsulfonyl group), a sulfur atom, or an oxygen atom, more preferably —NH—, a sulfur atom, or an oxygen atom, and most preferably an oxygen atom.

$Y_1$ and $Y_2$ in Formula (1-A2) or Formula (1-B2) each are preferably independently NR (in which R is a hydrogen atom, an alkyl group, an alkenyl group, an aryl group, a heterocyclic group, an acyl group, an alkylsulfonyl group, or an arylsulfonyl group), more preferably NR (in which R is a hydrogen atom or an alkyl group), and most preferably a —NH— group.

$R_{10}$ and $R_{11}$ in Formula (C2) or Formula (D2) each are preferably independently an alkyl group, an aryl group, or a heterocyclic group, and more preferably an alkyl group or an aryl group.

Then, examples of the compounds represented by Formula (A2), Formula (B2), Formula (1-A2), Formula (1-B2), Formula (C2), and Formula (D2), respectively, will be shown below, but the invention is not limited to them.

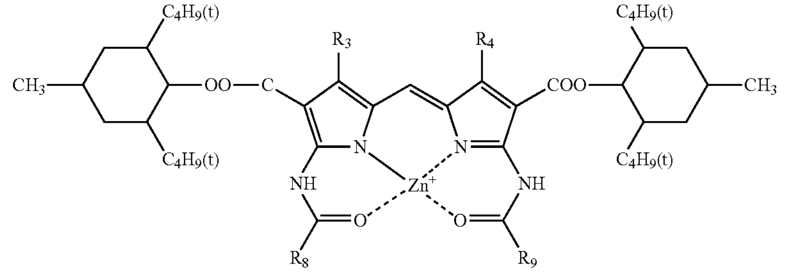

| Compound | $R_3$, $R_4$ | $R_8$ | $R_9$ |
|---|---|---|---|
| A'-1 | $—CH_3$ | $—CH_3$ | 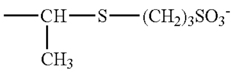 |
| A'-2 | Same as above | 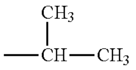 | Same as above |
| A'-3 | Same as above | $—C_4H_9(t)$ | Same as above |

-continued

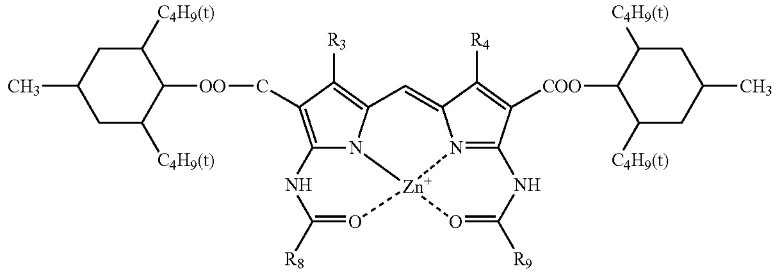

| Compound | $R_3$, $R_4$ | $R_8$ | $R_9$ |
|---|---|---|---|
| A'-4 | Same as above | 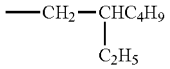 | Same as above |
| A'-5 | Same as above | 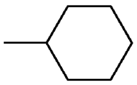 | 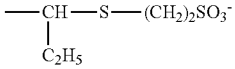 |
| A'-6 | Same as above | $-CH_2OCH_3$ | Same as above |
| A'-7 | Same as above | 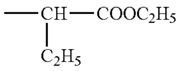 | Same as above |
| A'-8 | Same as above | $-CH_2OCH_2COOC_2H_5$ | Same as above |
| A'-9 | Same as above | 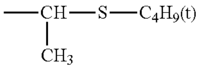 | Same as above |
| A'-10 | Same as above | 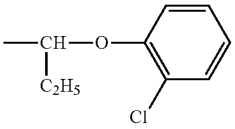 | Same as above |
| A'-11 | Same as above | 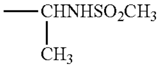 | Same as above |
| A'-12 | Same as above | 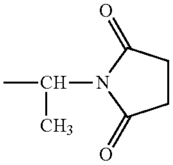 | Same as above |
| A'-13 | Same as above | 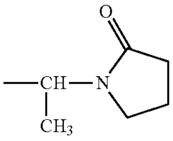 | Same as above |
| A'-14 | Same as above | $-CH_2OCH_2COOH$ | Same as above |
| A'-15 | Same as above | 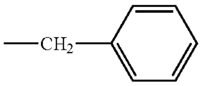 | Same as above |
| A'-16 | Same as above | $-CF_3$ | Same as above |
| A'-17 | Same as above | $-OC_2H_5$ | $-CH_2-S-(CH_2)_2SO_3^-$ |
| A'-18 | Same as above | $-NHC_4H_9$ | Same as above |
| A'-19 | $-C_2H_5$ | $-C_4H_9(t)$ | Same as above |

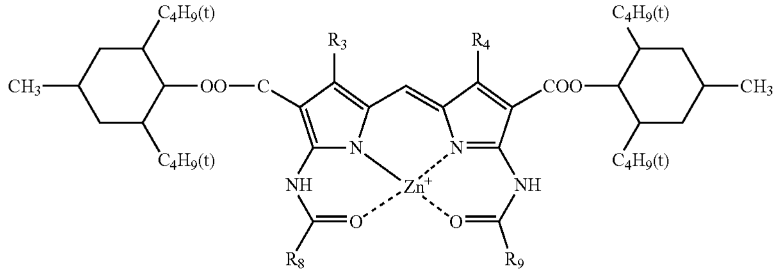

| Compound | $R_3$, $R_4$ | $R_8$ | $R_9$ |
|---|---|---|---|
| A'-20 | 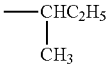 | $-C_4H_9(t)$ | 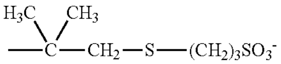 |
| A'-21 | 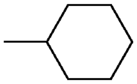 | Same as above | 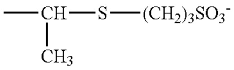 |
| A'-22 | $-CH_3$ | Same as above | 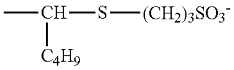 |
| A'-23 | Same as above | Same as above | $-(CH_2)_3S(CH_2)_3SO_3^-$ |
| A'-24 | Same as above | Same as above | 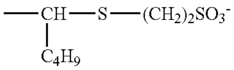 |
| A'-25 | Same as above | Same as above | $-(CH_2)_3SO_2(CH_2)_3SO_3^-$ |
| A'26 | Same as above | Same as above | 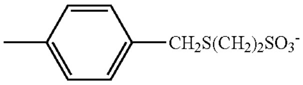 |
| A'-27 | Same as above | Same as above | 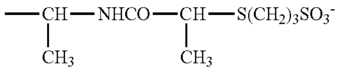 |
| A'-28 | Same as above | Same as above | 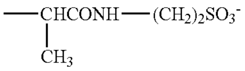 |
| A'-29 | Same as above | Same as above | 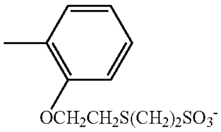 |
| A'-30 | Same as above | 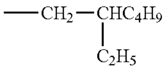 | 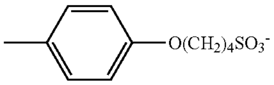 |
| A'-31 | Same as above | | 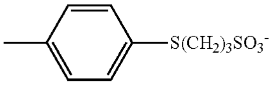 |
| A'-32 | Same as above | 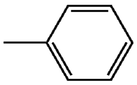 | Same as above |
| A'-33 | Same as above | Same as above | 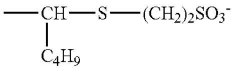 |

-continued
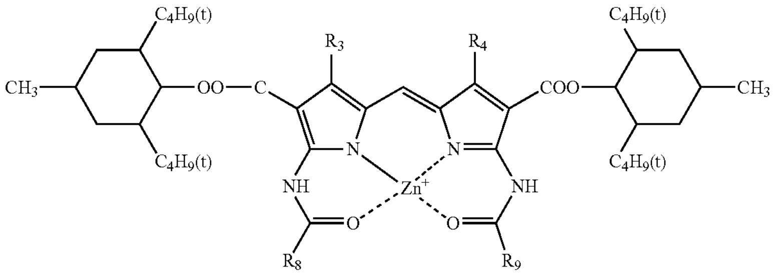
| Compound | $R_3$, $R_4$ | $R_8$ | $R_9$ |
|---|---|---|---|
| A'-34 | Same as above | 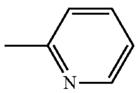 | Same as above |
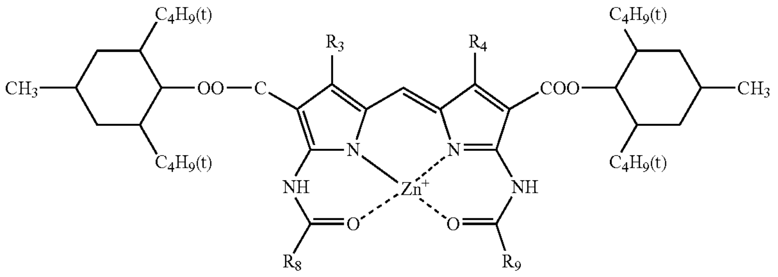
| Compound | $R_3$, $R_4$ | $R_8$ | $R_9$ |
|---|---|---|---|
| A'-35 | $-CH_3$ | 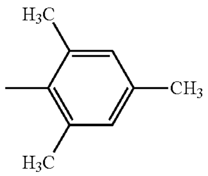 | 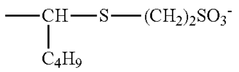 |
| A'-36 | Same as above | 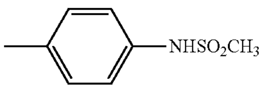 | Same as above |
| A'-37 | Same as above | 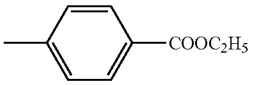 | Same as above |
| A'-38 | Same as above | 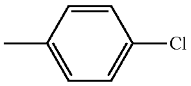 | Same as above |
| A'-39 | Same as above | 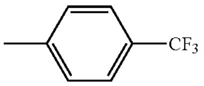 | Same as above |
| A'-40 | Same as above | 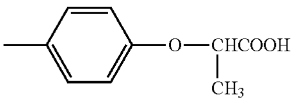 | Same as above |

-continued
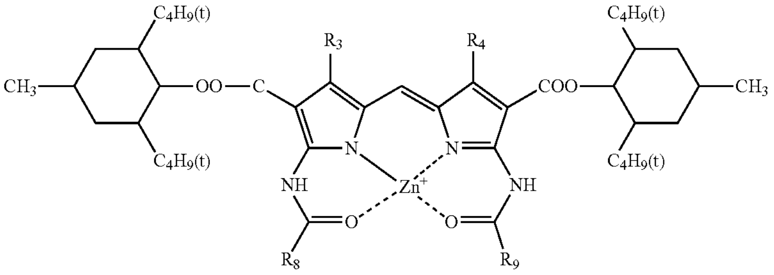
| Compound | $R_3$, $R_4$ | $R_8$ | $R_9$ |
|---|---|---|---|
| A'-41 | Same as above | 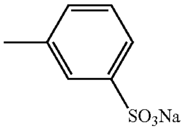 | Same as above |
| A'-42 | Same as above | 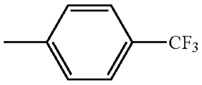 | 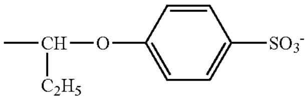 |
| A'-43 | Same as above | —$C_4H_9$(t) | 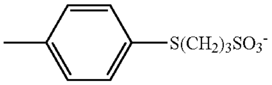 |
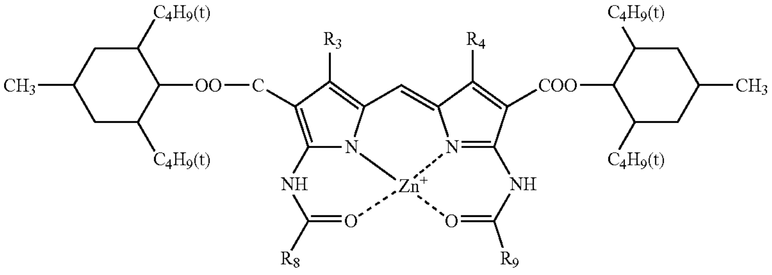
| Compound | $R_3$, $R_4$ | $R_8$ | $R_9$ |
|---|---|---|---|
| B'-1 | 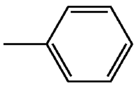 | —$C_4H_9$(t) | 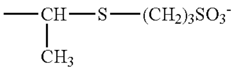 |
| B'-2 | 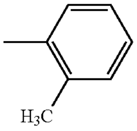 | Same as above | Same as above |
| B'-3 | 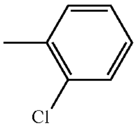 | Same as above | Same as above |
| B'-4 | 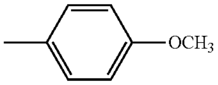 | Same as above | Same as above |

-continued
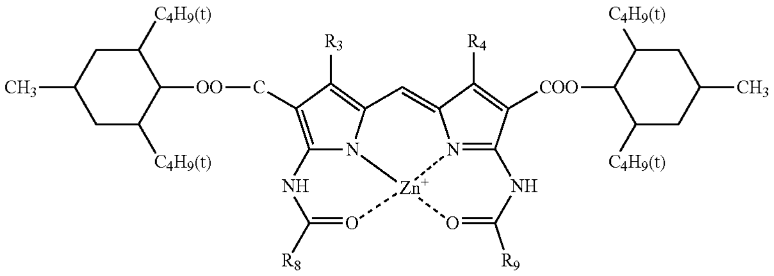
| Compound | $R_3$, $R_4$ | $R_8$ | $R_9$ |
|---|---|---|---|
| B'-5 | 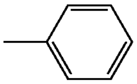 | 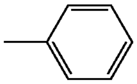 | Same as above |
| B'-6 | 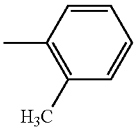 | 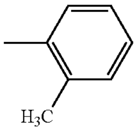 | Same as above |
| B'-7 | Same as above | 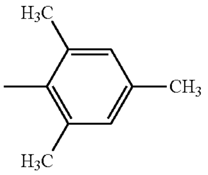 | Same as above |
| B'-8 | 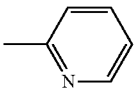 | $-C_4H_9(t)$ | Same as above |
| B'-9 | $-C_4H_9(t)$ | Same as above | Same as above |
| B'-10 | $-CH_3$ | 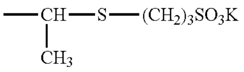 | Same as above |
| B'-11 | 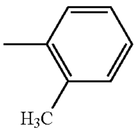 | 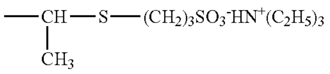 | Same as above |
| B'-12 | Same as above | $-(CH_2)_3S(CH_2)_3SO_3Na$ | $-(CH_2)_3S(CH_2)_3SO_3^-$ |
| B'-13 | Same as above | 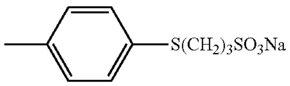 | 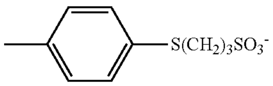 |
| B'-14 | $-CH_3$ | Same as above | Same as above |
| B'-15 | 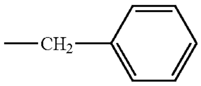 | $-(CH_2)_3S(CH_2)_3SO_3Na$ | $-(CH_2)_3S(CH_2)_3SO_3^-$ |
| B'-16 | 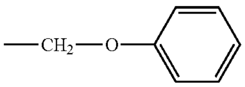 | 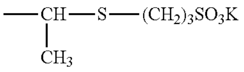 | 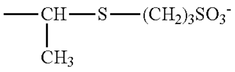 |

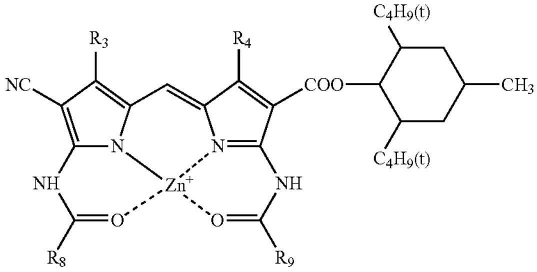

| Compound | $R_3$ | $R_4$ | $R_8$ | $R_9$ |
|---|---|---|---|---|
| C'-1 | 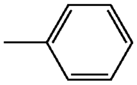 | $-CH_3$ | $-C_4H_9(t)$ | 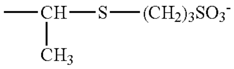 |
| C'-2 | 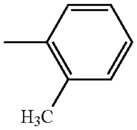 | Same as above | Same as above | Same as above |
| C'-3 | 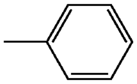 | 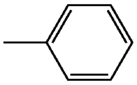 | Same as above | Same as above |
| C'-4 | Same as above | Same as above | 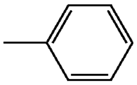 | Same as above |
| C'-5 | 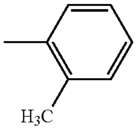 | 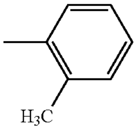 | 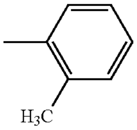 | Same as above |
| C'-6 | 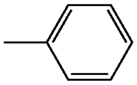 | 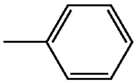 | 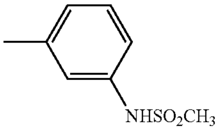 | Same as above |
| C'-7 | Same as above | Same as above | 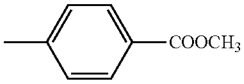 | Same as above |
| C'-8 | Same as above | Same as above | 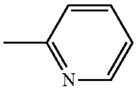 | Same as above |
| C'-9 | Same as above | Same as above | 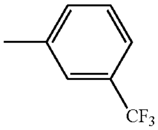 | Same as above |
| C'-10 | Same as above | Same as above | 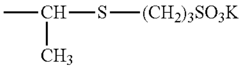 | Same as above |
| C'-11 | Same as above | Same as above | 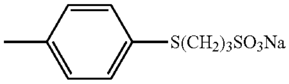 | 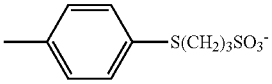 |
| C'-12 | Same as above | Same as above | $-(CH_2)_3S(CH_2)_3SO_3Na$ | $-(CH_2)_3S(CH_2)_3SO_3^-$ |

-continued

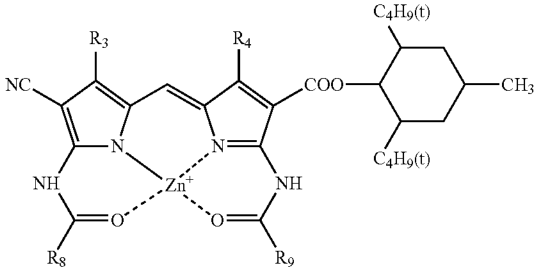

| Compound | $R_3$ | $R_4$ | $R_8$ | $R_9$ |
|---|---|---|---|---|
| C'-13 | $—CH_3$ | $—CH_3$ | 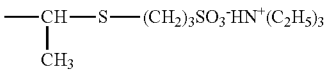 | 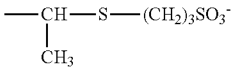 |
| C'-14 | 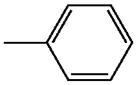 | $—CH_2OCH_3$ | Same as above | Same as above |
| C'-15 | 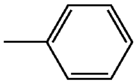 | $—(CH_2)_3S—C_8H_{17}$ | Same as above | Same as above |

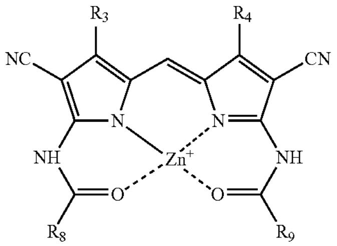

| Compound | $R_3$ | $R_4$ | $R_8$ | $R_9$ |
|---|---|---|---|---|
| D'-1 | 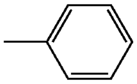 | 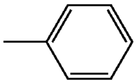 | $—C_4H_9(t)$ | 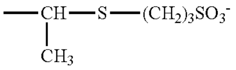 |
| D'-2 | Same as above | Same as above | $—CH_2(CH_2)_7CH{=}CH_2$ | Same as above |
| D'-3 | Same as above | Same as above | $—CH_2(CH_2)_5CH_2CH{=}CHCH_2C_5H_{11}$ | Same as above |
| D'-4 | Same as above | Same as above | 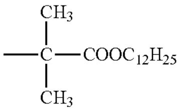 | Same as above |
| D'-5 | Same as above | Same as above | $—CH_2OCH_2COOH$ | Same as above |
| D'-6 | Same as above | Same as above | 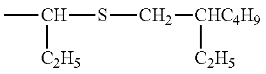 | Same as above |

-continued
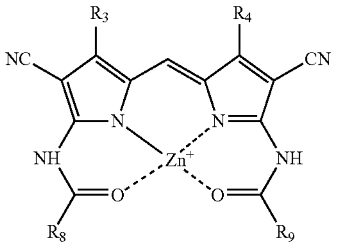
| Compound | $R_3$ | $R_4$ | $R_8$ | $R_9$ |
|---|---|---|---|---|
| D'-7 | Same as above | Same as above | 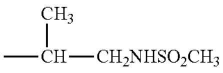 | Same as above |
| D'-8 | Same as above | Same as above | 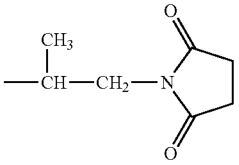 | Same as above |
| D'-9 | Same as above | Same as above | 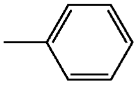 | Same as above |
| D'-10 | 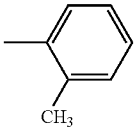 | 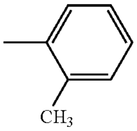 | 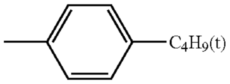 | Same as above |
| D'-11 | Same as above | Same as above | 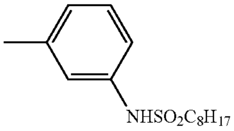 | Same as above |
| D'-12 | Same as above | Same as above | 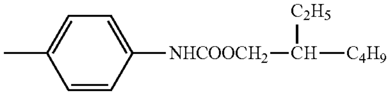 | Same as above |
| D'-13 | Same as above | Same as above | 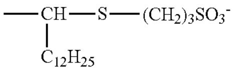 | 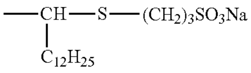 |
| D'-14 | $—CH_3$ | $—CH_3$ | Same as above | Same as above |

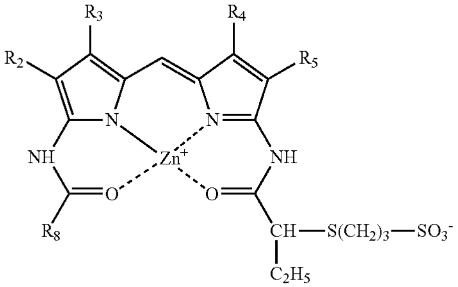

| Compound | $R_2$ | $R_3$ | $R_4$ | $R_5$ | $R_8$ |
|---|---|---|---|---|---|
| E'-1 | 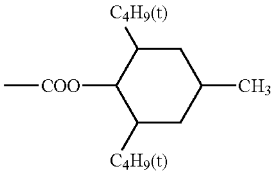 | —$CH_3$ | $CH_3$ | —$SO_2CH_3$ | —$C_4H_9$(t) |
| E'-2 | Same as above | Same as above | Same as above | 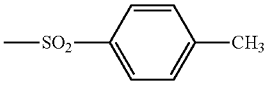 | Same as above |
| E'-3 | Same as above | 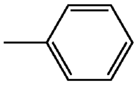 | 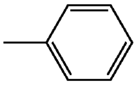 | Same as above | Same as above |
| E'-4 | Same as above | —$CH_3$ | —$CH_3$ | Same as above | 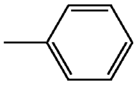 |
| E'-5 | —$SO_2CH_3$ | Same as above | Same as above | 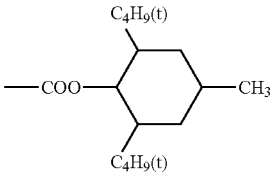 | Same as above |
| E'-6 | Same as above | Same as above | Same as above | Same as above | —$C_4H_9$(t) |
| E'-7 | —$SO_2C_4H_9$ | —$CH_3$ | —$CH_3$ | Same as above | Same as above |
| E'-8 | 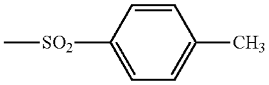 | Same as above | Same as above | Same as above | Same as above |
| E'-9 | 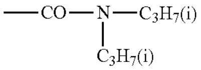 | 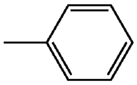 | 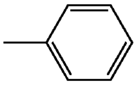 | Same as above | Same as above |
| E'-10 | 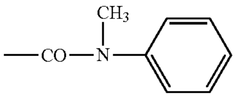 | Same as above | Same as above | Same as above | Same as above |
| E'-11 | —$COOC_2H_5$ | Same as above | Same as above | Same as above | Same as above |
| E'-12 | 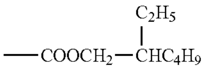 | Same as above | Same as above | Same as above | Same as above |
| E'-13 | 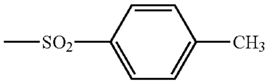 | Same as above | Same as above | 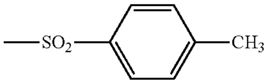 | Same as above |

-continued
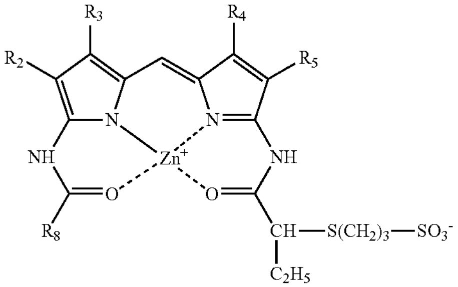
| Compound | $R_2$ | $R_3$ | $R_4$ | $R_5$ | $R_8$ |
| --- | --- | --- | --- | --- | --- |
| E'-14 | Same as above | $—CH_3$ | $—CH_3$ | Same as above | Same as above |
| E'-15 | $—COOC_2H_5$ | 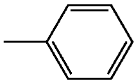 | 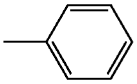 | $—COOC_2H_5$ | Same as above |
F'-1
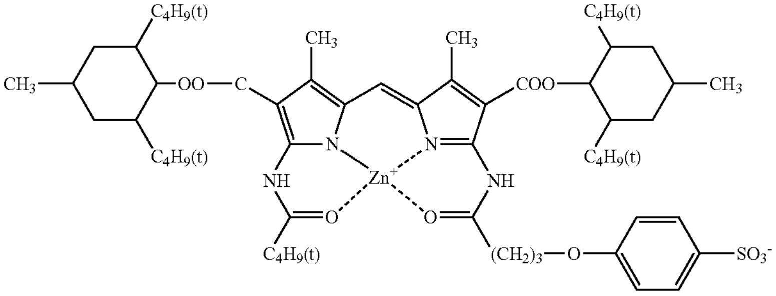
F'-2
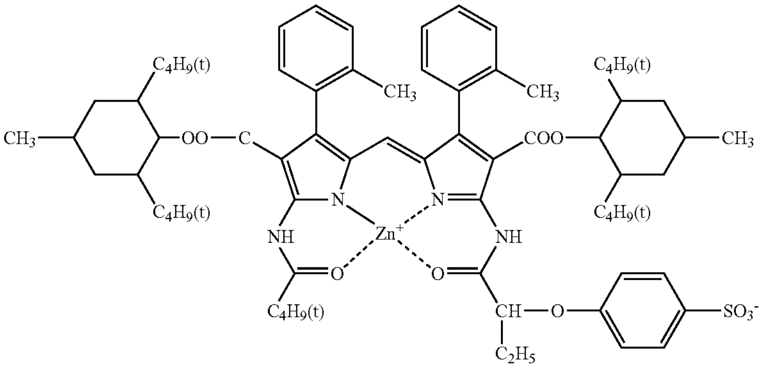
F'-3
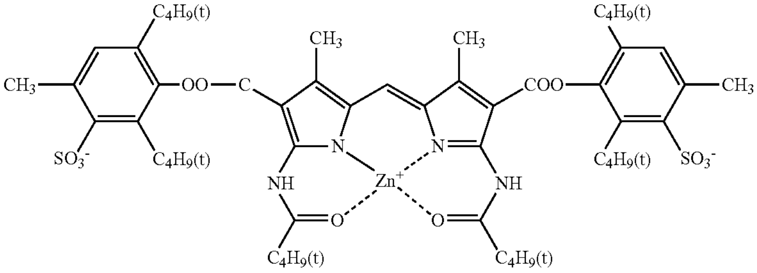

-continued
F'-4
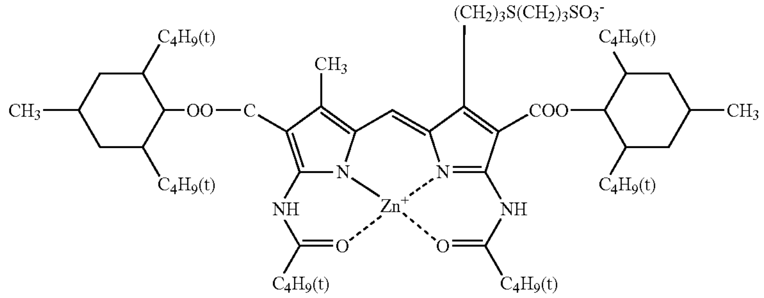
F'-5
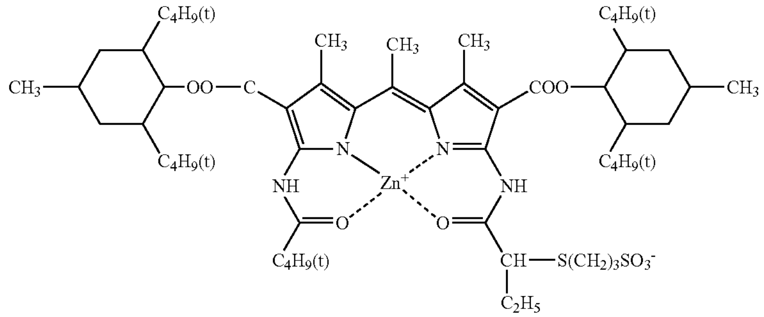
F'-6
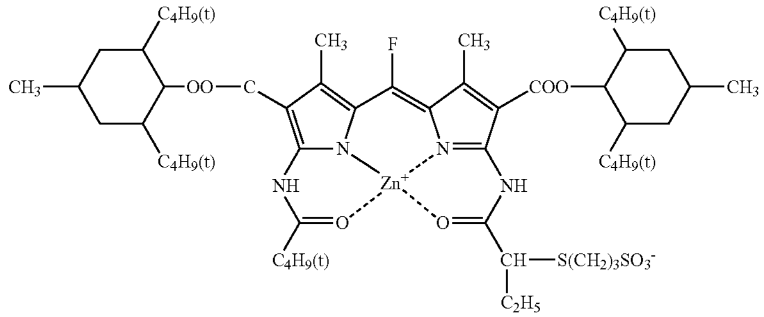
F'-7
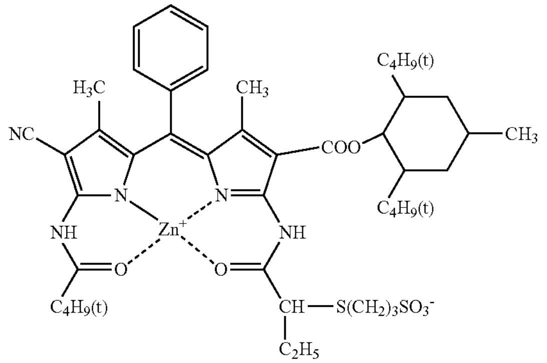
F'-8
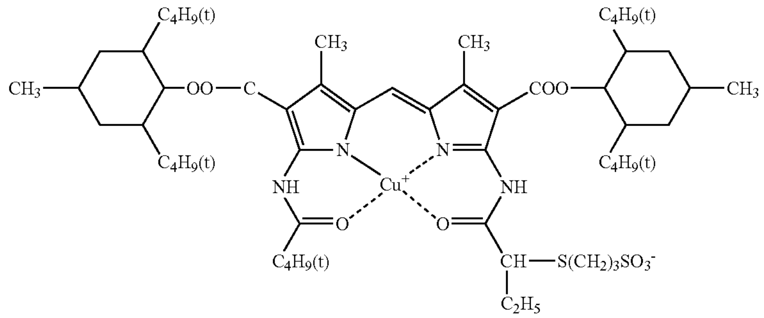

-continued
F'-9
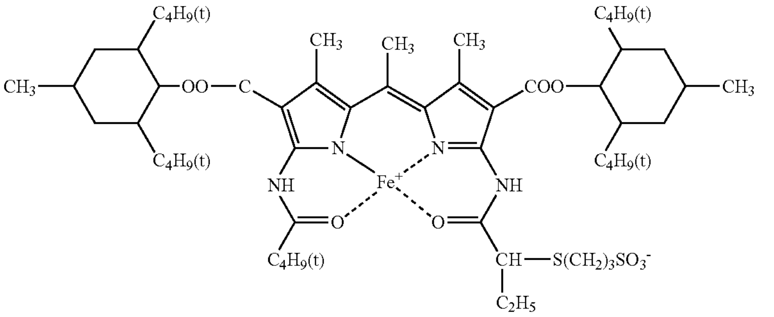
F'-10
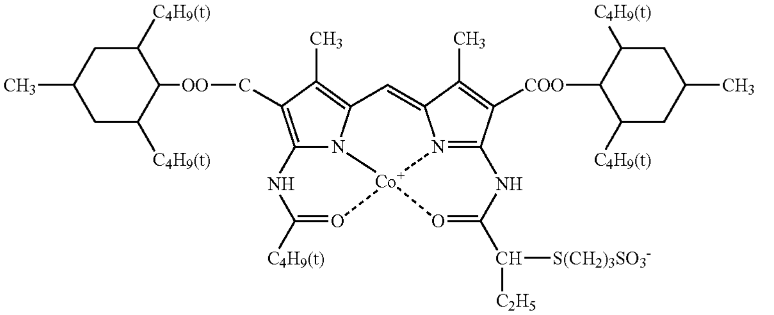
F'-11
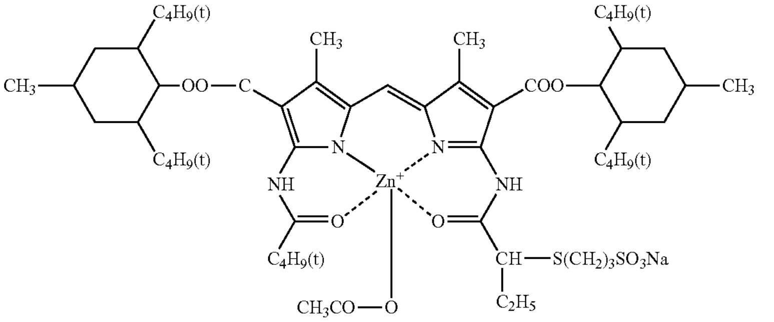
F'-12
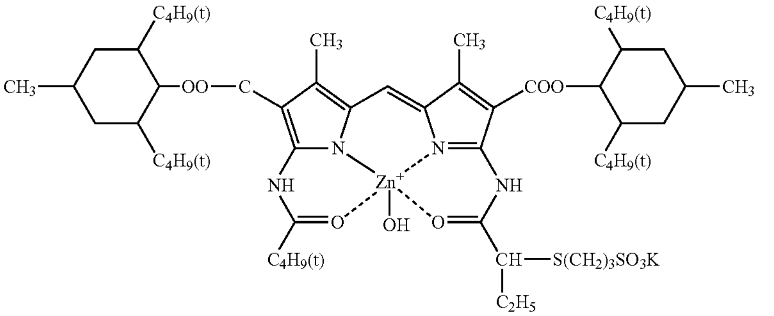
F'-13
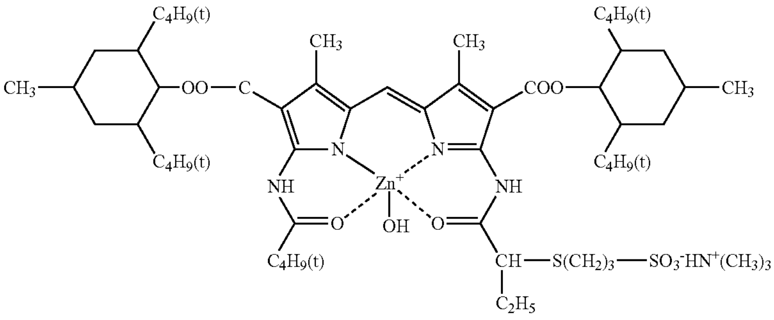

-continued

F'-14

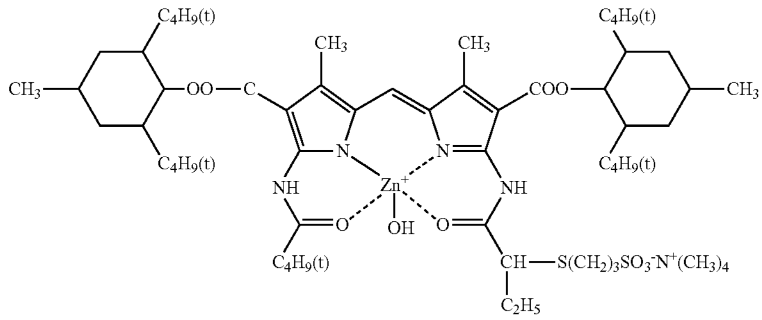

F'-15

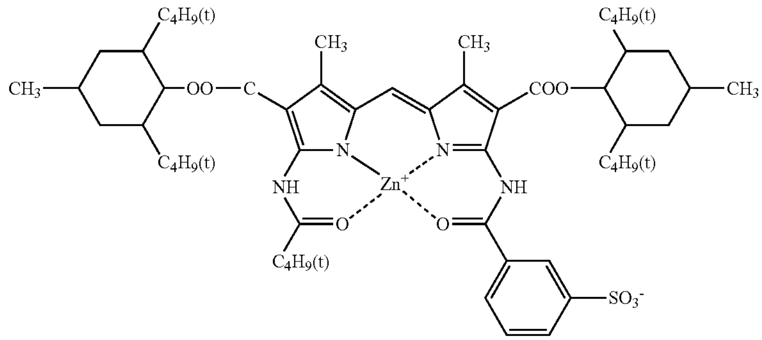

F'-16

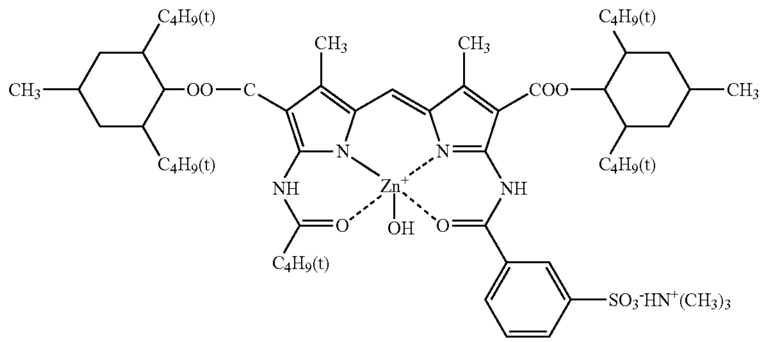

The compounds represented by Formula (A2), Formula (B2), Formula (C2), and Formula (D2), respectively, may each be synthesized by the method described in US Application Publication No. 2008/0076044 A1.

The amount of at least one compound selected from the compounds of Formula (A2) and Formula (B2), which is included in the colored curable composition of the second exemplary embodiment of the invention, varies depending on a molecular weight and a molar absorption coefficient thereof, and is preferably from 0.5 to 80% by mass, more preferably from 0.5 to 60% by mass, and most preferably from 0.5 to 50% by mass, with respect to the total solid contents of the colored curable composition.

The colored curable composition according to the second exemplary embodiment of the invention and the color filter using the colored curable composition may include a phthalocyanine compound such as those disclosed in US Application Publication No. 2008/0076044 A1, a triarylmethane coloring agent having an absorption maximum at 550 to 650 nm such as C.I. Acid Blue 7, C.I. Acid Blue 83, C.I. Acid Blue 90, C.I. Solvent Blue 38, C.I. Acid Violet 17, C.I. Acid Violet 49 or C.I. Acid Green 3, in addition to the compounds of Formula (A2), Formula (B2), Formula (C2), and Formula (D2) and tautomers thereof.

Further, a xanthene colorant having an absorption maximum at 500 nm to 600 nm, for example, C. I. Acid. Red 289 may also be used.

The phthalocyanine coloring agent or the triarylmethane coloring agent may be used as long as the effect of the invention is not deteriorated, and the amount thereof is preferably from 0.5 to 50% by mass with respect to the total solid contents of the colored curable composition of the invention.

In order to manufacture a blue filter array, it is preferable that a mixture of a metal complex of the invention and at least one of the phthalocyanine coloring agents is used.

In this case, a proportion of them within the mixture varies depending on their molar absorption coefficients, spectrometric properties required, film thickness, and the like. Generally, the proportion (i.e., total amount of metal complex of the invention: phthalocyanine coloring agent) is from 10:1 to 1:20, and preferably in a range of from 5:1 to 1:10.

Binder

It is preferable that the colored curable composition according to the first or second exemplary embodiment of the invention includes at least one binder. The binder used in the invention is not particularly limited as long as it is alkali-soluble, and is preferably selected from the viewpoints of heat resistance, developability, availability, and the like.

The alkali-soluble binder is preferably a linear organic polymer soluble in organic solvents and developable with an aqueous weakly alkaline solution. Examples of such linear organic polymer include polymers having a carboxylic acid at their side chain, for example methacrylic acid copolymers, acrylic acid copolymers, itaconic acid copolymers, crotonic acid copolymers, maleic acid copolymers and partially-esterified maleic acid copolymers as those described in the specifications of JP-A No. 59-44615 and JP-B Nos. 54-34327, 58-12577 and 54-25957. Acidic cellulose derivatives having a carboxylic acid at the side chain are particularly useful.

Other useful binders include polymers prepared by adding an acid anhydride to a polymer having a hydroxyl group, polyhydroxystyrene resins, polysiloxane resins, poly(2-hydroxyethyl (meth)acrylate), polyvinyl pyrrolidone, polyethylene oxide and polyvinyl alcohol.

Alternatively, the binder used in the invention may be a copolymer of monomers having a hydrophilic group, and examples of the monomers include alkoxyalkyl (meth)acrylate, hydroxyalkyl (meth)acrylate, glycerol (meth)acrylate, (meth)acrylamide, N-methylolacrylamide, secondary and tertiary alkylacrylamide, dialkylaminoalkyl (meth)acrylate, morpholino (meth)acrylate, N-vinylpyrrolidone, N-vinylcaprolactam, vinylimidazole, vinyltriazole, methyl (meth)acrylate, ethyl (meth)acrylate, branched or straight propyl (meth) acrylate, branched or straight butyl (meth)acrylate, and phenoxyhydroxypropyl (meth)acrylate.

As other monomers having a hydrophilic group, monomers containing a tetrahydrofurfuryl group, a phosphoric acid moiety, a phosphoric acid ester moiety, a quaternary ammonium salt moiety, an ethyleneoxy chain, a propyleneoxy chain, a sulfonic acid moiety and a salt thereof, or a morpholinoethyl group are also useful.

Alternatively, in order to improve the crosslinking efficacy, the binder may have a polymerizable group in a side chain thereof. For example, polymers containing an allyl group, a (meth)acryl group, an allyloxyalkyl group or the like are also useful.

Examples of the polymers having a polymerizable group include KS Resist-106 (trade name, manufactured by Osaka Organic Chemical Industry Ltd.), and CYCLOMER P series (registered name, manufactured by DICEL Chemical Industries, Ltd.).

Moreover, in order to increase the strength of a cured film, an alcohol-soluble nylon or polyether of 2,2-bis(4-hydroxyphenyl)-propane and epichlorohydrin is also useful.

Among the various binders, from a viewpoint of heat resistance, the binder to be used in the invention is preferably a polyhydroxystyrene resin, a polysiloxane resin, an acryl resin, an acrylamide resin, or an acryl/acrylamide copolymer resin. Alternatively, from a viewpoint of developability control, the binder to be used in the invention is preferably an acryl resin, an acrylamide resin, or an acryl/acrylamide copolymer resin.

Examples of the acryl resin preferably include a copolymer including a monomer selected from benzyl (meth)acrylate, (meth)acryl, hydroxyethyl (meth)acrylate, and (meth)acrylamide, KS-RESIST-106 (trade name, manufactured by Osaka Organic Chemical Industry Ltd.), and CYCLOMER P-series.

As the binder used in the invention, an alkali-soluble phenol resin may also be used. The alkali-soluble phenol resin may be preferably used when the composition of the invention is used as a positive-working composition. Examples of the alkali-soluble phenol resin include novolak resins and vinyl polymers.

Examples of the novolak resins include a product obtained by condensation of a phenol and an aldehyde in the presence of an acid catalyst. Examples of the phenol include phenol, cresol, ethylphenol, butylphenol, xylenol, phenylphenol, catechol, resorcinol, pyrogallol, naphthol, and bisphenol A.

Examples of the aldehyde include formaldehyde, paraformaldehyde, acetaldehyde, propionaldehyde, and benzaldehyde.

As the phenol, only one phenol compound, or alternatively a combination of two or more phenol compounds, may be used. As the aldehyde, only one aldehyde compound may be used, or alternatively a combination of two or more aldehyde compounds may be used.

Specific examples of the novolak resin include metacresol, paracresol, and condensation products of a mixture thereof with formalin.

The molecular weight distribution of the novolak resin may be regulated by fractionation or the like. Alternatively, a low-molecular weight component having a phenolic hydroxy group such as bisphenol C or bisphenol A may be mixed with the novolak resin.

The binder is preferably a polymer having a mass average molecular weight (in terms of polystyrene measured by GPC method) of from 1,000 to $2\times10^5$, further preferably from 2,000 to $1\times10^5$, and particularly preferably from 5,000 to $5\times10^4$.

The amount of the binder in the colored curable composition is preferably 10% by mass to 90% by mass, further preferably 20% by mass to 80% by mass, particularly preferably 30% by mass to 70% by mass, with respect to the total solid contents of the colored curable composition of the invention.

Crosslinking Agent

The colored curable composition according to the first exemplary embodiment of the invention includes, as a coloring agent, at least one selected from the group consisting of a compound of Formula (A1) and a compound of Formula (B1), and tautomers thereof. The colored curable composition according to the second exemplary embodiment of the invention includes, as a coloring agent, at least one selected from the group consisting of a compound of Formula (A2) and a compound of Formula (B2), and tautomers thereof. For this reason, the colored curable compositions of the first and second exemplary embodiments of the invention have excellent color purity, have a high adsorption coefficient even when the compositions are formed into a thin film, and have excellent fastness, as compared with the previous ones. When the compositions each further include the crosslinking agent, a highly cured film is obtained.

Any crosslinking agent may be used without particular limitation insofar as it can cure a film through a crosslinking reaction. Examples of the crosslinking agent include (a) an epoxy resin, (b) a melamine compound, guanamine compound, glycoluril compound, or urea compound substituted by at least one substituent selected from a methylol group, an alkoxymethyl group, and an acyloxymethyl group, and (c) a phenol compound, naphthol compound, or hydroxyanthracene compound substituted by at least one substituent selected from a methylol group, an alkoxymethyl group, and an acyloxymethyl group. Among the above, polyfunctional epoxy resins are particularly preferable.

As (a) the epoxy resin, any epoxy resin may be used as long as it has an epoxy group and crosslinking property. Examples thereof include divalent glycidyl group-containing low-molecular weight compounds such as bisphenol A glycidyl ether, ethylene glycol diglycidyl ether, butanediol diglycidyl ether, hexanediol diglycidyl ether, dihydroxybiphenyl diglycidyl ether, phthalic acid diglycidyl ester, or N,N-diglycidylaniline; trivalent glycidyl group-containing low-molecular weight compounds such as trimethylolpropane triglycidyl ether, trimethylolphenol triglycidyl ether, or TRIS P-PA triglycidyl ether; tetravalent glycidyl group-containing low-molecular weight compounds such as pentaerythritol tetraglycidyl ether or tetramethylol bisphenol A tetraglycidyl ether; polyvalent glycidyl group-containing low-molecular weight compounds such as dipentaerythritol pentaglycidyl ether or dipentaerythritol hexaglycidyl ether; glycidyl group-containing high-molecular weight compounds such as polyglycidyl (meth)acrylate or a 1,2-epoxy-4-(2-oxylanyl)cyclohexane adduct of 2,2-bis(hydroxymethyl)-1-butanol.

The number of substitution with the methylol group, the alkoxymethyl group, and/or the acyloxymethyl group included in the crosslinking agent (b) is 2 to 6 in the case of the melamine compound, and 2 to 4 in the case of the glycoluril compound, the guanamine compound, or the urea compound, preferably 5 to 6 in the case of the melamine compound, and 3 to 4 in the case of the glycoluril compound, the guanamine compound, or the urea compound.

The melamine compound, the guanamine compound, the glycoluril compound and the urea compound of (b) are collectively referred to as "compound(s) (b)" (or a methylol group-containing compound, alkoxymethyl group-containing compound, or acyloxymethyl group-containing compound) in some cases hereinafter.

The methylol group-containing compound of the compound (b) may be obtained by heating the alkoxymethyl group-containing compound of the compound (b) in an alcohol in the presence of an acid catalyst such as hydrochloric acid, sulfuric acid, nitric acid, or methanesulfonic acid. The acyloxymethyl group-containing compound of the compound (b) may be obtained by mixing and stirring the methylol group-containing compound of the compound (b) with acyl chloride in the presence of a basic catalyst.

Hereinafter, specific examples of the compound (b) having any of the substituents are described.

Examples of the melamine compound include a hexamethylol melamine, hexamethoxymethyl melamine, compounds in which 1 to 5 methylol groups of hexamethylol melamine are methoxymethylated or mixtures thereof, hexamethoxyethyl melamine, hexaacyloxymethyl melamine, and compounds in which 1 to 5 methylol groups of hexamethylol melamine are acyloxymethylated or mixtures thereof.

Examples of the guanamine compound include tetramethylol guanamine, tetramethoxymethyl guanamine, compounds in which 1 to 3 methylol groups of tetramethylol guanamine are methoxymethylated or mixtures thereof, tetramethoxyethyl guanamine, tetraacyloxymethyl guanamine, and compounds in which 1 to 3 methylol groups of tetramethylol guanamine are acyloxymethylated or mixtures thereof.

Examples of the glycoluril compound include tetramethylol glycoluril, tetramethoxymethyl glycoluril, compounds in which 1 to 3 methylol groups of tetramethylol glycoluril are methoxymethylated or mixtures thereof, and compounds in which 1 to 3 methylol groups of tetramethylol glycoluril are acyloxymethylated or mixtures thereof.

Examples of the urea compound include tetramethylolurea, tetramethoxymethylurea, compounds in which 1 to 3 methylol groups of tetramethylolurea are methoxymethylated or mixtures thereof, and tetramethoxyethylurea.

The compounds (b) may be used singly, or may be used in combination of two or more of them.

The crosslinking agent (c), that is, a phenol compound, naphthol compound, or hydroxyanthracene compound substituted with at least one group selected from a methylol group, an alkoxymethyl group, and an acyloxymethyl group suppresses intermixing with an overcoat photoresist, and further enhances a film strength by thermal crosslinking like the case of the crosslinking agent (b).

These compounds are collectively referred to as "compound(s) (c)" (or a methylol group-containing compound, an alkoxymethyl group-containing compound, or an acyloxymethyl group-containing compound) in some cases hereinafter.

The total number of methylol groups, acyloxymethyl groups, or alkoxymethyl groups included in the crosslinking agent (c) has to be at least 2 per molecule. For example, a compound in which a phenol compound, serving as a skeleton, is substituted at all of 2-positions and 4-positions is preferable from the viewpoints of thermal crosslinking properties and storage stability. When the skeleton is a naphthol compound or a hydroxyanthracene compound, all of ortho- and para-positions relative to the OH group in the compound is preferably substituted. The 3- or 5-position of the phenol compound as the skeleton may be unsubstituted or may have a substituent. Also in the naphthol compound as the skeleton, positions other than the ortho-position relative to the OH group may be unsubstituted or may have a substituent.

The methylol group-containing compound of the compound (c) may be obtained by using, as a raw material, a compound in which an ortho-position or a para-position (2-position or 4-position) of a phenolic OH group is a hydrogen atom, and subjecting this compound to a reaction with formalin in the presence of a basic catalyst such as sodium hydroxide, potassium hydroxide, ammonia, or tetraalkylammonium hydroxide.

The alkoxymethyl group-containing compound of the compound (c) may be obtained by heating the methylol group-containing compound of the compound (c) in an alcohol in the presence of an acid catalyst such as hydrochloric acid, sulfuric acid, nitric acid, or methanesulfonic acid.

The acyloxymethyl group-containing compound of the compound (c) may be obtained by subjecting the methylol group-containing compound of the compound (c) to a reaction with acyl chloride in the presence of a basic catalyst.

Examples of a skeleton compound in the crosslinking agent (c) include a phenol compound, a naphthol compound, and a hydroxyanthracene compound in each of which an ortho-position or a para-position of a phenolic OH group is unsubstituted. Examples thereof include respective isomers of phenol and cresol, 2,3-xylenol, 2,5-xylenol, 3,4-xylenol, 3,5-xylenol, bisphenols such as bisphenol A, 4,4'-bishydroxybiphenyl, TRIS P-PA (trade name, manufactured by Honsyu Chemical Industry Co Ltd.), naphthol, dihydroxynaphthalene, and 2,7-dihydroxyanthracene.

Specific examples of the crosslinking agent (c) include trimethylolphenol, tri(methoxymethyl)phenol, a compound in which 1 to 2 methylol groups of trimethylolphenol are methoxymethylated, trimethylol-3-cresol, tri(methoxymethyl)-3-cresol, a compound in which 1 to 2 methylol groups of trimethylol-3-cresol are methoxymethylated, dimethylolcresols such as 2,6-dimethylol-4-cresol, tetramethylolbisphenol A, tetramethoxymethylbisphenol A, a compound in which 1 to 3 methylol groups of tetramethylolbisphenol A are methoxymethylated, tetramethylol-4,4'-bishydroxybiphenyl, tetramethoxymethyl-4,4'-bishydroxybiphenyl, a hexamethylol of TRIS P-PA, a hexamethoxymethyl of TRIS P-PA, a compound in which 1 to 5 methylol groups of a hexamethylol of TRIS P-PA are methoxymethylated, and bishydroxymethylnaphthalene diol.

Examples of the hydroxyanthracene compound include 1,6-dihydroxymethyl-2,7-dihydroxyanthracene.

Examples of the acyloxymethyl group-containing compound include a compound in which a part or all of methylol groups of the methylol group-containing compound are acyloxymethylated.

Among these compounds, examples of a preferable compound include trimethylolphenol, bishydroxymethyl-p-cresol, tetramethylolbisphenol A, a hexamethylol of TRIS P-PA (manufactured by Honsyu Chemical Industry Co Ltd.), and a phenol compound in which methylol groups of them are substituted with an alkoxymethyl group, or both of methylol group and an alkoxymethyl group.

These compounds (c) may be used singly, or may be used in combination of two or more of them.

When a crosslinking agent is included, the total amount of the crosslinking agents (a) to (c) in the coloring agent-containing curable composition varies depending on a material, and is preferably 1 to 70% by mass, more preferably 5 to 50% by mass, particularly preferably 7 to 30% by mass, with respect to the total solid content (mass) of the composition. When the total amount is in this range, sufficient curing degree and dissolution property of an unexposed area may be retained, and deficiency of a curing degree at an exposed area, and remarkable reduction in dissolution property of an unexposed area may be prevented.

Polymerizable Monomer

It is preferable that the colored curable composition according to the first or second exemplary embodiment of the invention includes at least one polymerizable monomer. The colored curable composition includes a polymerizable monomer mainly when the colored curable composition is formed into a negative-working composition.

The polymerizable monomer together with a photopolymerization initiator described later may be included in a positive-working composition containing a naphthoquinonediazide compound described later, and, in this case, a curing degree of a formed pattern may be more increased. The polymerizable monomer will be described hereinbelow.

The polymerizable monomer is preferably a compound having a boiling point of 100° C. or higher under a normal pressure and having at least one addition-polymerizable ethylenic unsaturated group. Examples thereof include monofunctional acrylates and methacrylates such as polyethylene glycol mono(meth)acrylate, polypropylene glycol mono (meth)acrylate, and phenoxyethyl (meth)acrylate; polyfunctional acrylates and (meth)acrylates such as polyethylene glycol di(meth)acrylate, trimethylolethane tri(meth)acrylate, neopentylglycol di(meth)acrylate, pentaerythritol tri(meth) acrylate, pentaerythritol tetra(meth)acrylate, dipentaerythritol penta(meth)acrylate, dipentaerythritol hexa(meth)acrylate, hexanediol (meth)acrylate, trimethylolpropane tri (acryloyloxypropyl)ether, tri(acryloyloxyethyl) isocyanurate; compounds obtained by adding ethylene oxide or propylene oxide to a polyfunctional alcohol such as glycerin or trimethylol and (meth)acrylating this product; urethane acrylates such as those described in JP-B Nos. 48-41708, 50-6034, and JP-A No. 51-37193; and polyester acrylates and epoxy acrylates, which are reaction products of an epoxy resin and (meth)acrylic acid, described in JP-A No. 48-64183 and JP-B Nos. 49-43191 and 52-30490, and mixtures thereof.

Further, those disclosed as a photocurable monomer or oligomer in Journal of the Adhesion Society of Japan, Vol. 20, No. 7, pp. 300 to 308 is also used as the polymerizable monomer.

The amount of the polymerizable monomer in the colored curable composition is preferably 0.1% by mass to 90% by mass, further preferably 1.0% by mass to 80% by mass, particularly preferably 2.0% by mass to 70% by mass, with respect to the solid contents in the colored curable composition.

Radiation-Sensitive Compound

The colored curable composition according to the first or second exemplary embodiment of the invention includes at least one radiation-sensitive compound. The radiation-sensitive compound is able to effect chemical reactions such as generation of radicals, acids and bases in response to irradiation of UV light of which wavelength is 400 nm or less. The radiation-sensitive compound is used for making the alkali-soluble binder insoluble by cross-linking, polymerization, decomposition of acidic groups, or the like, or for making coating layers insoluble to an alkali developer by inducing polymerization of the polymerizable monomer and oligomer remaining in the coating layer or cross-linking of the cross-linking agent.

In particular, when the colored curable composition according to the first or second exemplary embodiment of the invention is composed in a negative-working composition, it is preferable that the colored curable composition includes a photopolymerization initiator. When the photosensitive colored curable composition is composed in a positive-working composition, it is preferred that the colored curable composition includes a naphthoquinonediazide compound.

Photopolymerization Initiator

Next, a photopolymerization initiator included in the colored curable composition of the first or second exemplary embodiment of the invention when the colored curable composition is a negative-working composition will be described.

The photopolymerization initiator is not particularly limited as long as it can polymerize the polymerizable monomer, and it is preferable that the initiator is selected from the viewpoints of properties, an initiation efficiency, an absorption wavelength, availability, and the cost.

The positive-working composition containing a naphthoquinonediazide compound may further include the photopolymerization initiator. In this case, a curing degree of a formed pattern may be more increased.

Examples of the photopolymerization initiator include at least one active halogen compound selected from a halomethyloxadiazole compound and a halomethyl-s-triazide compound, a 3-aryl-substituted coumarin compound, a lophine dimer, a benzophenone compound, an acetophenone compound and a derivative thereof, a cyclopentadiene-benzene-iron complex and a salt thereof, and an oxime compound.

Examples of the active halogen compound such as halomethyloxadiazole include 2-halomethyl-5-vinyl-1,3,4-oxadiazole compounds described in JP-B No. 57-6096, 2-trichloromethyl-5-styryl-1,3,4-oxadiazole, 2-trichloromethyl-5-(p-cyanostyryl)-1,3,4-oxadiazole, and 2-trichloromethyl-5-(p-methoxystyryl)-1,3,4-oxadiazole.

Examples of the halomethyl-s-triazine compound include a vinyl-halomethyl-s-triazine compound described in JP-B No. 59-1281, and 2-(naphtho-1-yl)-4,6-bis(halomethyl)-s-triazine compound and a 4-(p-aminophenyl)-2,6-bis(halomethyl)-s-triazine compound described in JP-A No. 53-133428.

Other examples of the photopolymerizable initiator include 2,4-bis(trichloromethyl)-6-p-methoxystyryl-s-triazine, 2,6-bis(trichloromethyl)-4-(3,4-methylenedioxyphenyl)-1,3,5-triazine, 2,6-bis(trichloromethyl)-4-(4-methoxyphenyl)-1,3,5-triazine, 2,4-bis(trichloromethyl)-6-(1-p-dimethylaminophenyl-1,3-butadienyl)-s-triazine, 2-trichloromethyl-4-amino-6-p-methoxystyryl-s-triazine, 2-(naphtho-1-yl)-4,6-bis(trichloromethyl)-s-triazine, 2-(4-methoxy-naphtho-1-yl)-4,6-bis(trichloromethyl)-s-triazine, 2-(4-ethoxy-naphtho-1-yl)-4,6-bis(trichloromethyl)-s-triazine, 2-(4-butoxy-naphtho-1-yl)-4,6-bis(trichloromethyl)-s-triazine, 2-[4-(2-methoxyethyl)-naphtho-1-yl]-4,6-bis(trichloromethyl)-s-triazine, 2-[4-(2-ethoxyethyl)-naphtho-1-yl]-4,6-bis(trichloromethyl)-s-triazine, 2-[4-(2-butoxyethyl)-naphtho-1-yl]-4,6-bis(trichloromethyl)-s-triazine, 2-(2-methoxy-naphtho-1-yl)-4,6-bis(trichloromethyl)-s-triazine, 2-(6-methoxy-5-methyl-naphtho-2-yl)-4,6-bis(trichloromethyl)-s-triazine, 2-(6-methoxy-naphtho-2-yl)-4,6-bis(trichloromethyl)-s-triazine, 2-(5-methoxy-naphtho-1-yl)-4,6-bis(trichloromethyl)-s-triazine, 2-(4,7-dimethoxy-naphtho-1-yl)-4,6-bis(trichloromethyl)-s-triazine, 2-(6-ethoxy-naphtho-2-yl)-4,6-bis(trichloromethyl)-s-triazine, 2-(4,5-dimethoxy-naphtho-1-yl)-4,6-bis(trichloromethyl)-s-triazine, 4-[p-N,N-bis(ethoxycarbonylmethyl)aminophenyl]-2-6-bis(trichloromethyl)-s-triazine, 4-[o-methyl-p-N,N-bis(ethoxycarbonylmethyl)aminophenyl]-2,6-bis(trichloromethyl)-s-triazine, 4-[p-N,N-bis(chloroethyl)aminophenyl]-2,6-bis(trichloromethyl)-s-triazine, 4-[o-methyl-p-N,N-di(chloroethyl)aminophenyl]-2,6-bis(trichloromethyl)-s-triazine, 4-(p-N-chloroethylaminophenyl)-2,6-bis(trichloromethyl)-s-triazine, 4-(p-N-ethoxycarbonylmethylaminophenyl)-2,6-bis(trichloromethyl)-s-triazine, 4-[p-N,N-di(phenyl)aminophenyl]-2,6-bis(trichloromethyl)-s-triazine, 4-(p-N-chloroethylcarbonylaminophenyl)-2,6-bis(trichloromethyl)-s-triazine, 4-[p-N-(p-methoxyphenyl)carbonylaminophenyl]-2,6-bis(trichloromethyl)-s-triazine, 4-[m-N,N-bis(ethoxycarbonylmethyl)aminophenyl]-2,6-bis(trichloromethyl)-s-triazine, 4-[m-bromo-p-N,N-bis(ethoxycarbonylmethyl)aminophenyl]-2,6-bis(trichloromethyl)-s-triazine, 4-[m-chloro-p-N,N-bis(ethoxycarbonylmethyl)aminophenyl]-2,6-bis(trichloromethyl)-s-triazine, 4-[m-fluoro-p-N,N-bis(ethoxycarbonylmethyl)aminophenyl]-2,6-bis(trichloromethyl)-s-triazine, 4-[o-bromo-p-N,N-bis(ethoxycarbonylmethyl)aminophenyl]-2,6-bis(trichloromethyl)-s-triazine, 4-[o-chloro-p-N,N-bis(ethoxycarbonylmethyl)aminophenyl]-2,6-bis(trichloromethyl)-s-triazine, 4-[o-fluoro-p-N,N-bis(ethoxycarbonylmethyl)aminophenyl]-2,6-bis(trichloromethyl)-s-triazine, 4-[o-bromo-p-N,N-bis(chloroethyl)aminophenyl]-2,6-bis(trichloromethyl)-s-triazine, 4-[o-chloro-p-N,N-bis(chloroethyl)aminophenyl]-2,6-bis(trichloromethyl)-s-triazine, 4-[o-fluoro-p-N,N-bis(chloroethyl)aminophenyl]-2,6-bis(trichloromethyl)-s-triazine, 4-[m-bromo-p-N,N-di(chloroethyl)aminophenyl]-2,6-bis(trichloromethyl)-s-triazine, 4-[m-chloro-p-N,N-bis(chloroethyl)aminophenyl]-2,6-bis(trichloromethyl)-s-triazine, 4-[m-fluoro-p-N,N-bis(chloroethyl)aminophenyl]-2,6-bis(trichloromethyl)-s-triazine, 4-(m-bromo-p-N-ethoxycarbonylmethylaminophenyl)-2,6-bis(trichloromethyl)-s-triazine, 4-(m-chloro-p-N-ethoxycarbonylmethylaminophenyl)-2,6-bis(trichloromethyl)-s-triazine, 4-(m-fluoro-p-N-ethoxycarbonylmethylaminophenyl)-2,6-bis(trichloromethyl)-s-triazine, 4-(o-bromo-p-N-ethoxycarbonylmethylaminophenyl)-2,6-bis(trichloromethyl)-s-triazine, 4-(o-chloro-p-N-ethoxycarbonylmethylaminophenyl)-2,6-bis(trichloromethyl)-s-triazine, 4-(o-fluoro-p-N-ethoxycarbonylmethylaminophenyl)-2,6-bis(trichloromethyl)-s-triazine, 4-(m-bromo-p-N-chloroethylaminophenyl)-2,6-bis(trichloromethyl)-s-triazine, 4-(m-chloro-p-N-chloroethylaminophenyl)-2,6-bis(trichloromethyl)-s-triazine, 4-(m-fluoro-p-N-chloroethylaminophenyl)-2,6-bis(trichloromethyl)-s-triazine, 4-(o-bromo-p-N-chloroethylaminophenyl)-2,6-bis(trichloromethyl)-s-triazine, 4-(o-chloro-p-N-chloroethylaminophenyl)-2,6-bis(trichloromethyl)-s-triazine, and 4-(o-fluoro-p-N-chloroethylaminophenyl)-2,6-bis(trichloromethyl)-s-triazine.

In addition, TAZ Series such as TAZ-107, TAZ-110, TAZ-104, TAZ-109, TAZ-140, TAZ-204, TAZ-113 and TAZ-123 (all trade names, manufactured by Midori Kagaku Co., Ltd.), T Series such as T-OMS, T-BMP, T-R, and T-B (all trade names, manufactured by PANCHIM, Irgacure Series), IRGACURE Series such as IRGACURE 369, IRGACURE 784, IRGACURE 651, IRGACURE 184, IRGACURE 500, IRGACURE 1000, IRGACURE 149, IRGACURE 819, and IRGACURE 261, Darocure Series such as DAROCURE 1173 (all registered names, manufactured by Ciba-Geigy), 4,4'-bis(diethylamino)-benzophenone, 2-(O-benzoyloxime)-1-[4-(phenylthio)phenyl]-1,2-octanedione, 1-(O-acetyloxime)-1-[9-ethyl-6-(2-methylbenzoyl)-9H-carbazol-3-yl]ethanone, 2-benzyl-2-dimethylamino-4-morpholinobutyrophenone, 2,2-dimethoxy-2-phenylacetophenone, 2-(o-chlorophenyl)-4,5-diphenylimidazolyl dimer, 2-(o-fluorophenyl)-4,5-diphenylimidazolyl dimer, 2-(o-methoxyphenyl)-4,5-diphenylimidazolyl dimer, 2-(p-methoxyphenyl)-4,5-diphenylimidazolyl dimer, 2-(p-dimethoxyphenyl)-4,5-diphenylimidazolyl dimer, 2-(2,4-dimethoxyphenyl)-4,5-diphenylimidazolyl dimer, 2-(p-methylmercaptophenyl)-4,5-diphenylimidazolyl dimer, and benzoin isopropyl ether are usefully used.

Particularly preferable examples include oxime-O-acyl compounds such as 2-(O-benzoyloxime)-1-[4-(phenylthio)phenyl]-1,2-octanedione and 1-(O-acetyloxime)-1-[9-ethyl-6-(2-methylbenzoyl)-9H-carboazol-3-yl]ethanone.

In the photosensitive colored curable composition of the first or second exemplary embodiment of the invention, any of other known photopolymerization initiators may be used in combination with the aforementioned photopolymerization initiator.

Specifically, examples of the other known photopolymerization initiators include a vicinal polyketolaldonyl compound such as those disclosed in U.S. Pat. No. 2,367,660, an α-carbonyl compound such as those disclosed in U.S. Pat. Nos. 2,367,661 and 2,367,670, an acyloin ether such as those disclosed in U.S. Pat. No. 2,448,828, an aromatic acyloin compound substituted with a-hydrocarbon such as those disclosed in U.S. Pat. No. 2,722,512, a polynuclear quinone compound such as those disclosed in U.S. Pat. Nos. 3,046,127 and 2,951,758, a combination of triallylimidazole dimer/p-aminophenyl ketone such as those disclosed in U.S. Pat. No. 3,549,367, and benzothiazole compound/trihalomethyl-s-triazine compound such as those disclosed in JP-B No. 51-48516.

The amount of the photopolymerization initiator in the colored curable composition according to the first or second exemplary embodiment of the invention is preferably 0.01 to 50% by mass, more preferably 1 to 30% by mass, particularly preferably 1 to 20% by mass, with respect to the solid content of the polymerizable monomer. When the amount is in this range, polymerization proceeds good, and an excellent film strength is obtained.

A sensitizer and/or a light stabilizer may be used together with the photopolymerization initiator.

Examples thereof include benzoin, benzoin methyl ether, 9-fluorenone, 2-chloro-9-fluorenone, 2-methyl-9-fluorenone, 9-anthrone, 2-bromo-9-anthrone, 2-ethyl-9-anthrone, 9,10-anthraquinone, 2-ethyl-9,10-anthraquinone, 2-t-butyl-9,10-anthraquinone, 2,6-dichloro-9,10-anthraquinone, xanthone, 2-methylxanthone, 2-methoxyxanthone, 2-ethoxyxanthone, thioxanthone, 2,4-diethylthioxanthone, acridone, 10-butyl-2-chloroacridone, benzil, dibenzalacetone, p-(dimethylamino)phenyl styryl ketone, p-(dimethylamino)phenyl-p-methyl styryl ketone, benzophenone, p-(dimethylamino) benzophenone (or Michler's ketone), p-(diethylamino) benzophenone, benzoanthrone, a benzothiazole compound such as those described in JP-B No. 51-48516, Tinuvin 1130, and Tinuvin 400.

Besides, it is preferable to further add a thermal polymerization inhibitor such as hydroquinone, p-methoxyphenol, di-t-butyl-p-cresol, pyrogallol, t-butylcatechol, benzoquinone, 4,4'-thiobis(3-methyl-6-t-butylphenol), 2,2'-methylenebis(4-methyl-6-t-butylphenol), or 2-mercaptobenzimidazole.

Naphthoquinonediazide Compound

Next, a naphthoquinonediazide compound included in the colored curable composition according to the first or second exemplary embodiment of the invention when the curable composition is formed into a positive-working composition will be described.

The naphthoquinonediazide compound refers to a compound containing at least one o-quinonediazide group. Examples thereof include o-naphthoquinonediazide-5-sulfonic acid ester, o-naphthoquinonediazide-5-sulfonic acid amide, o-naphthoquinonediazide-4-sulfonic acid ester, and o-naphthoquinonediazide-4-sulfonic acid amide. These esters and amide compounds may be produced by known methods using, for example, a phenol compound represented by Formula (1) described in JP-A Nos. 2-84650 and 3-49437.

When the colored curable composition of the first or second exemplary embodiment of the invention is formed into a positive-working composition, it is preferable that the alkali-soluble phenol resin and the crosslinking agent are usually dissolved in an organic solvent at proportions of about 2 to 50% by mass and about 2 to 30% by mass, respectively. In the case of the colored curable composition of the first exemplary embodiment, the amount of the naphthoquinonediazide compound is preferably about 2% by mass to 30% by mass, and the amount of one or more compounds (colorants) selected from Formula (A1) and Formula (B1) is preferably about 2% by mass to 50% by mass, with respect to a solution in which the binder and the crosslinking agent are dissolved. In the case of the colored curable composition of the second exemplary embodiment, the amount of the naphthoquinonediazide compound is preferably about 2% by mass to 30% by mass, and the amount of one or more compounds (colorants) selected from Formula (A2) and Formula (B2) is preferably about 2% by mass to 50% by mass, with respect to a solution in which the binder and the crosslinking agent are dissolved.

Solvent

Upon preparation of the colored curable composition of the first or second exemplary embodiment of the invention, generally, a solvent may be used. The solvent to be used is not basically particularly limited as long as it satisfies solubility of respective components of the composition, and coating property of the photosensitive colored curable composition of the first or second exemplary embodiment, and the solvent is preferably selected in view of solubility, coating property, and safety of the binder.

Examples of the solvent include esters, for example, ethyl acetate, n-butyl acetate, isobutyl acetate, amyl formate, isoamyl acetate, isobutyl acetate, butyl propionate, isopropyl butyrate, ethyl butyrate, butyl butyrate, alkyl esters, methyl lactate, ethyl lactate, methyl oxyacetate, ethyl oxyacetate, butyl oxyacetate, methyl methoxyacetate, ethyl methoxyacetate, butyl methoxyacetate, methyl ethoxyacetate, ethyl ethoxyacetate, 3-oxypropionic acid alkyl esters such as methyl 3-oxypropionate and ethyl 3-oxypropionate (e.g. methyl 3-methoxypropionate, ethyl 3-methoxypropionate, methyl 3-ethoxypropionate, ethyl 3-ethoxypropionate), 2-oxypropionic acid alkyl esters such as methyl 2-oxypropionate, ethyl 2-oxypropionate, and propyl 2-oxypropionate (e.g. methyl 2-methoxypropionate, ethyl 2-methoxypropionate, propyl 2-methoxypropionate, methyl 2-ethoxypropionate, ethyl 2-ethoxypropionate, methyl 2-oxy-2-methylpropionate, ethyl 2-oxy-2-methylpropionate, methyl 2-methoxy-2-methylpropionate, ethyl 2-ethoxy-2-methylpropionate), methyl pyruvate, ethyl pyruvate, propyl pyruvate, methyl acetoacetate, ethyl acetoacetate, methyl 2-oxobutanoate, and ethyl 2-oxobutanoate; ethers, for example, diethylene glycol dimethyl ether, tetrahydrofuran, ethylene glycol monomethyl ether, ethylene glycol monoethyl ether, methylcellosolve acetate, ethylcellosolve acetate, diethylene glycol monomethyl ether, diethylene glycol monoethyl ether, diethylene glycol monobutyl ether, propylene glycol methyl ether, propylene glycol methyl ether acetate, propylene glycol ethyl ether acetate, and propylene glycol propyl ether acetate; ketones, for example, methyl ether ketone, cyclohexanone, and 2-heptanone, and 3-heptanone; and aromatic hydrocarbons, for example, toluene and xylene.

Among them, methyl 3-ethoxypropionate, ethyl 3-ethoxypropionate, ethylcellosolve acetate, ethyl lactate, diethylene glycol dimethyl ether, butyl acetate, methyl 3-methoxypropionate, 2-heptanone, cyclohexanone, ethylcarbitol acetate, butylcarbitol acetate, propylene glycol methyl ether, and prolylene glycol methyl ether acetate are more preferable.

Additives

If necessary, the colored curable composition of the first or second exemplary embodiment of the invention may further include any of various additives, for example, fillers, polymer compounds other than the aforementioned polymer compounds, surfactants, adhesion promoters, antioxidants, ultraviolet absorbing agents, and aggregation inhibitors.

Specific examples of the various additives include fillers such as glass or alumina; polymer compounds other than binder resins, such as polyvinyl alcohol, polyacrylic acid, polyethylene glycol monoalkyl ether, and polyfluoroalkyl acrylate; nonionic surfactants, cationic surfactants, or anionic surfactants; adhesion promoters such as vinyltrimethoxysilane, vinyltriethoxysilane, vinyltris(2-methoxyethoxy)silane, N-(2-aminoethyl)-3-aminopropylmethyldimethoxysilane, N-(2-aminoethyl)-3-aminopropyltrimethoxysilane, 3-aminopropyltriethoxysilane, 3-glycidoxypropyltrimethoxysilane, 3-glycidoxypropylmethyldimethoxysilane, 2-(3,4-epoxycyclohexyl)ethyltrimethoxysilane, 3-chloropropylmethyldimethoxysilane, 3-chloropropyltrimethoxysilane, 3-methacryloxypropyltrimethoxysilane, and 3-mercaptopropyltrimethoxysilane; antioxidants such as 2,2-thiobis(4-methyl-6-t-butylphenol) and 2,6-di-t-butylphenol; ultraviolet absorbing agents such as 2-(3-t-butyl-5-methyl-2-hydroxyphenyl)-5-chlorobenzotriazole and alkoxybenzophenone; and aggregation inhibitors such as sodium polyacrylate.

Alternatively, when alkali dissolution property of a region to be development-removed (for example, in the case of a negative-working composition, an uncured area), and developability of the photosensitive colored curable composition of the first or second exemplary embodiment of the invention is intended to be further improved, an organic carboxylic acid, preferably a low-molecular weight organic carboxylic acid having a molecular weight of 1,000 or less may be added to the composition. Examples thereof include aliphatic monocarboxylic acids such as formic acid, acetic acid, propionic acid, butyric acid, valeric acid, pivalic acid, caproic acid, diethylacetic acid, enanthic acid, and caprylic acid; aliphatic dicarboxylic acids such as oxalic acid, malonic acid, succinic acid, glutaric acid, adipic acid, pimelic acid, suberic acid, azelaic acid, sebacic acid, brassilic acid, methylmalonic acid, ethylmalonic acid, dimethylmalonic acid, methylsuccinic acid, tetramethylsuccinic acid, and citraconic acid; aliphatic tricarboxylic acids such as tricarballilic acid, aconitic acid, and camphoronic acid; aromatic monocarboxylic acids such as benzoic acid, toluic acid, cuminic acid, hemellitic acid, and mesitylene acid; aromatic polycarboxylic acids such as phthalic acid, isophthalic acid, terephthalic acid, trimellitic acid, trimesic acid, mellophanic acid, and pyromellitic acid; and other carboxylic acids such as phenylacetic acid, hydratropic acid, hydrocinnamic acid, mandelic acid, phenylsuccinic acid, atropic acid, cinnamic acid, methyl cinnamate, benzyl cinnamate, cinnamilydeneacetic acid, coumaric acid, and umbellic acid.

The colored curable composition of the first or second exemplary embodiment of the invention may be suitably used for forming a coloring pixel of a color filter used in a liquid crystal display device (LCD) or a solid-state imaging device (e.g. CCD, CMOS etc.), or for producing a printing ink, an ink jet ink, or a paint. Particularly, the composition may be suitably used for forming a coloring pixel for a solid-state imaging device such as CCD and CMOS.

The colored curable composition of the invention is preferably used for forming a coloring pattern which is fine and thin, and is particularly suitable for forming a color filter for a solid-state imaging device requiring a good rectangular cross-section profile. Specifically, when the size of a pixel pattern (side length of a pixel pattern seen from a substrate normal line direction) constituting the color filter is 2 μm or less (e.g. 0.5 to 2.0 μm), since the coloring agent amount is increased and further, the hue is a blue system, line width sensitivity is deteriorated, and the DOF margin becomes narrow and, as a result, pattern forming properties are easily impaired. This becomes particularly pronounced when the size of the pixel pattern is 1.0 to 1.7 μm (or, further, 1.2 to 1.5 μm). On the other hand, in the case of a thin film having a thickness of 1 μm or less, the amount of components other than the coloring agent in the film contributing to photolithography properties is relatively decreased, and increase in the coloring agent amount further decreases the amount of other components, whereby sensitivity is reduced and, at a low light exposure amount region, a pattern is easily peeled off. In such a case, thermal sagging is easily caused by thermal treatment such as post-baking. These defects are particularly pronounced when the film thickness is 0.005 μm to 0.9 μm (or, further, 0.1 μm to 0.7 μm).

Color Filter and Method of Producing the Same

The color filter of the first or second exemplary embodiment of the invention will be described in detail through a method of producing the same.

In the method of producing the color filter of the first or second exemplary embodiment of the invention, the colored curable composition of the first or second exemplary embodiment of the invention is used. The color filter of the first or second exemplary embodiment of the invention has a negative-working or positive-working colored pattern (resist pattern) image formed in such a manner that the colored curable composition of the first or second exemplary embodiment of the invention is applied on a support by a coating method such as rotation coating, casting coating or roll coating to form a radiation-sensitive composition layer, and the layer is irradiated with light via a predetermined mask pattern, followed by development using a developer.

A light source for light exposure, which may be applied to the colored curable composition of the first or second exemplary embodiment of the invention is not particularly limited, but may be a light source having a wavelength of 400 nm or less. For example, lamp light sources such as a xenon lamp, a halogen lamp, a tungsten lamp, a high pressure mercury lamp, a ultrahigh pressure mercury lamp, a metal halide lamp, a medium pressure mercury lamp, a low pressure mercury lamp, a carbon arc, and a fluorescent lamp, an Ar ion laser (364 nm, 351 nm, 10 mW to 1 W), a Kr ion laser (356 nm, 351 nm, 10 mW to 1 W), a solid laser such as a combination of Nd:YAG (YVO4) and SHG crystal×two times (355 nm, 5 mW to 1 W), a combination of a waveguide wavelength conversion element and AlGaAs, or a waveguide wavelength conversion element and an AlGaInP or AlGaAs semiconductor (300 nm to 350 nm, 5 mW to 100 mW), or a pulse laser such as a N2 laser (337 nm, pulse 0.1 to 10 mJ) or XeF (351 nm, pulse 10 to 250 mJ) may be utilized. When only a specified wavelength is used, an optical filter may be utilized.

Further, ultraviolet rays such as an ArF excimer laser (wavelength 193 nm), a KrF excimer laser (wavelength 248 nm), and an i-ray (wavelength 365 nm) may be used. From the viewpoints of the cost and the light exposure energy, a particularly preferable light exposure light source is ultraviolet ray, particularly an i-ray.

Further, a curing process of curing a formed pattern by heating and/or light exposure, if necessary, may be provided. As light or radiation used thereupon, radiation such as i-ray is particularly preferably used.

In production of the color filter according to the first or second exemplary embodiment of the invention, it is possible to prepare a color filter in a desired number of colors, by repeating the image-forming process (and as needed curing process) multiple times according to the desired number of colors in the case of a negative-working color filter and by repeating the image-forming process and the post-baking process multiple times according to the desired number of colors in the case of a positive-working color filter.

Examples of the substrates for use include soda-lime glass, Pyrex (registered tradename) glass, and quartz glass used, for example, in liquid-crystal display elements; and those having a transparent conductive film formed thereon, photoelectric converting device substrates, such as silicon substrate, used for example in image sensors; complimentary metal oxide semiconductors (CMOS); and the like. The substrate may have a black stripe formed thereon for separation of pixels.

In addition, an undercoat layer may be formed on the substrate as needed, from the viewpoints of improvement in adhesiveness to the upper layer, prevention of material diffusion, or planarization of the substrate surface.

As the developer used in the method of producing the coloring filter of the first or second exemplary embodiment of the invention, any developer may be used as long as it has such a formulation that it dissolves an area to be removed during development of the colored curable composition of the first or second exemplary embodiment of the invention (uncured portion, in the case of a negative-working composition), and, on the other hand, does not dissolve other areas (i.e., a cured portion in the case of a negative-working composition). Specifically, a combination of various organic solvents, or an alkaline aqueous solution may be used. Examples of the organic solvent include the aforementioned solvents which are used upon preparation of the composition of the first or second exemplary embodiment of the invention.

As the alkaline aqueous solution, an alkaline aqueous solution is used in which an alkaline compound such as sodium hydroxide, potassium hydroxide, sodium carbonate, sodium silicate, sodium metasilicate, aqueous ammonium, ethylamine, diethylamine, dimethylethanolamine, tetramethylammonium hydroxide, tetraethylammonium hydroxide, choline, pyrrole, piperidine, or 1,8-biazabicyclo-[5.4.0]-7-undecene at a concentration of 0.001 to 10% by mass, preferably 0.01 to 1% by mass. When the developer including such an alkaline aqueous solution is used, generally, the color filter is washed with water after development.

The color filter of the first or second exemplary embodiment of the invention may be used in a liquid crystal display device or a solid-state imaging device such as CCD, and is particularly suitable for a CCD device or a CMOS device having high resolution exceeding one million pixels. The color filter of the first or second exemplary embodiment of the invention may be used, for example, as a color filter which is arranged between a light-receiving portion of each pixel of a CCD, and a microlens that collects light.

EXAMPLES

The present invention will be specifically described below by referring to Examples, but the invention is not limited by them. Unless otherwise indicated, "part" and "%" are on mass basis.

Examples Relating to First Exemplary Embodiment

Synthesis Example A1

Synthesis of Exemplified Compound A-3

According to the following Reaction Scheme A1, Exemplified Compound A-3 which is a dipyrromethene metal complex compound according to the first exemplary embodiment of the invention was synthesized.

Reaction Scheme A1

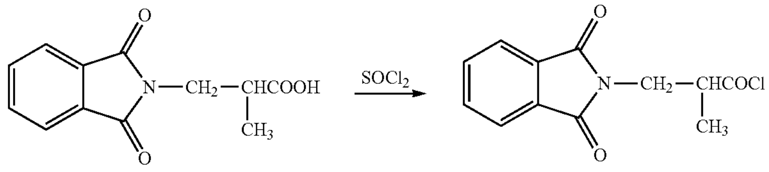

Intermediate A

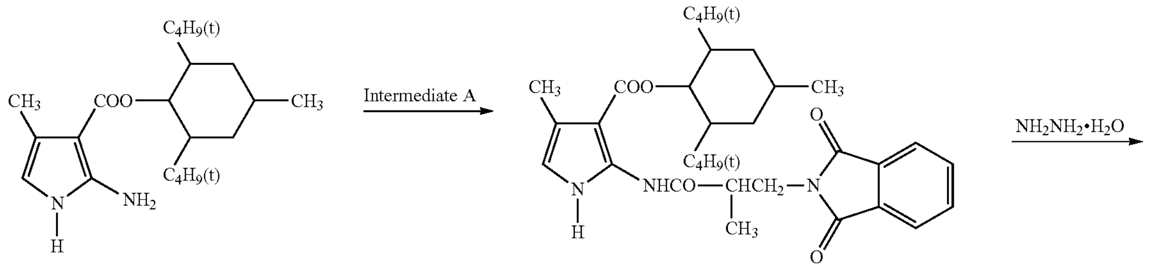

Intermediate B

Intermediate C

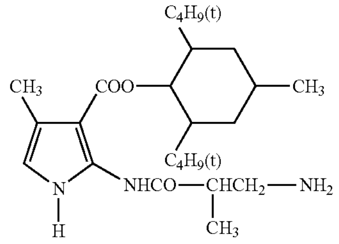

Intermediate D

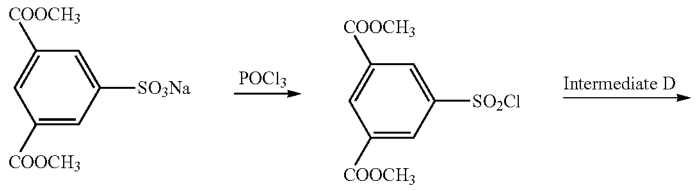

Intermediate E

-continued
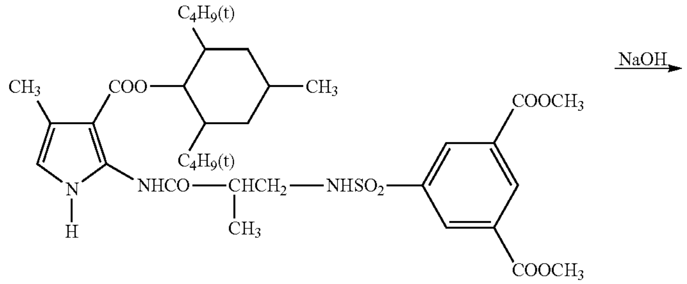
Intermediate F
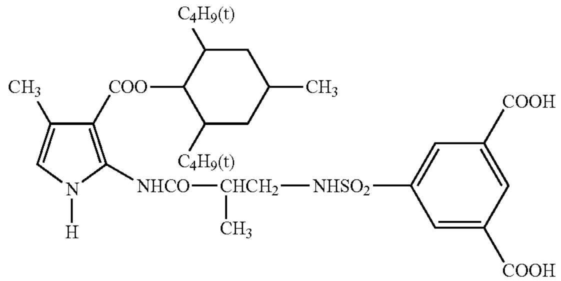
Intermediate G
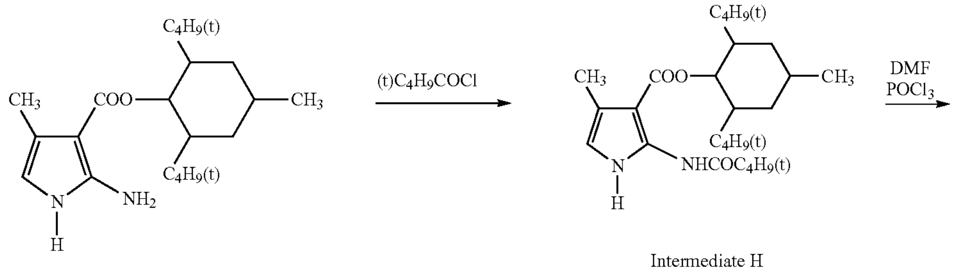
Intermediate B
Intermediate H
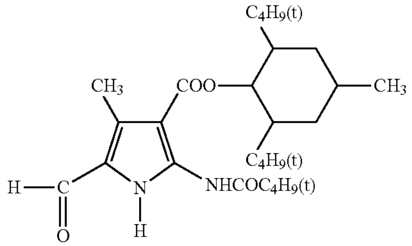
Intermediate I
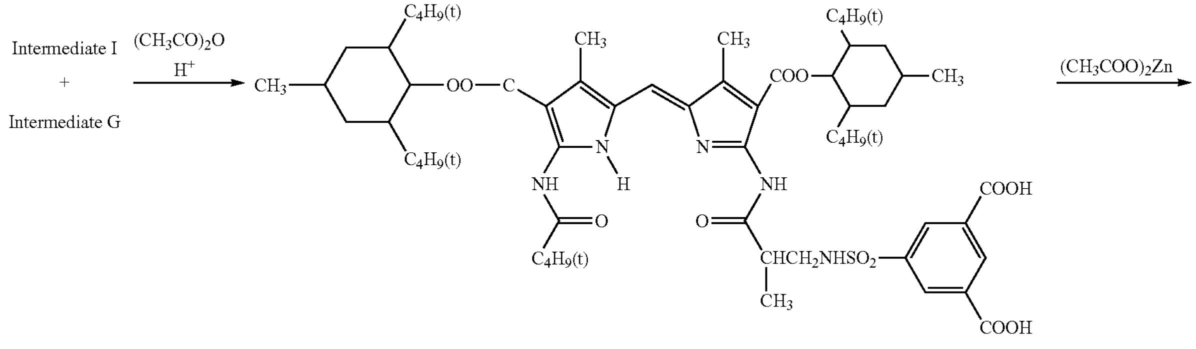
Intermediate J -continued

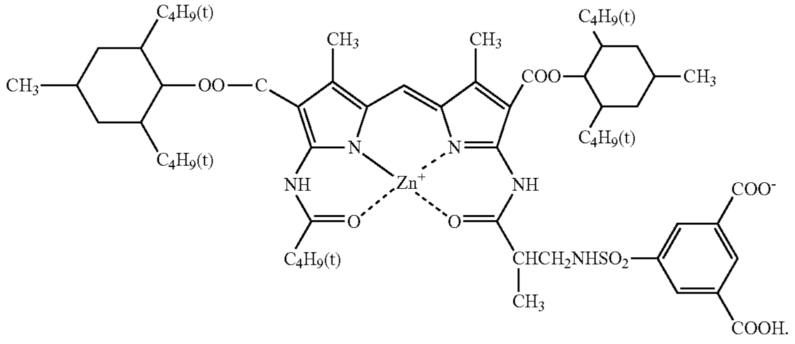

Exemplified Compound A-3

Synthesis of Intermediate A

To 23.3 g (0.1 mol) of 2-methyl-3-phthaloylpropionic acid, 150 ml of toluene was added, and the mixture was heated to 80° C. to 90° C. and stirred. To this solution, 17.8 g of thionyl chloride was added by dropping. After completion of the addition, stirring was performed at 80° C. to 90° C. for 3 hours to complete the reaction. After completion of the reaction, the reaction solution was subjected to reduced pressure to distill off toluene, thereby obtaining Intermediate A. To this residue was added 100 ml of acetonitrile to dissolve it, and the resultant solution was used for synthesis of Intermediate C.

Synthesis of Intermediate C

To 31.4 g (0.09 mol) of Intermediate B synthesized according to the method described in JP-A No. 10-316654 was added 150 ml of acetonitrile, and the mixture was stirred under heating refluxing. To this solution, an acetonitrile solution of Intermediate A obtained by the aforementioned method was added by dropping. After completion of the addition, stirring was performed for 5 hours under heating refluxing, to complete the reaction. This reaction solution was cooled to room temperature, and poured into 1,000 ml of water under stirring, to precipitate a crystal. This crystal was filtered, washed with water, and dried, thereby obtaining 57.2 g of Intermediate C (yield: 97.3%).

Synthesis of Intermediate D

To 39.5 g (0.07 mol) of Intermediate C obtained by the aforementioned method was added 250 ml of 2-propanol, and the mixture was stirred under heating refluxing. To this solution, 5.0 g (0.1 mol) of hydrazine monohydrate was added by dropping. After completion of the addition, stirring under heating refluxing was performed for 4 hours to complete the reaction. After completion of the reaction, this reaction solution was subjected to extraction by adding 500 ml of ethyl acetate and 1,000 ml of a 3% aqueous sodium bicarbonate solution. This ethyl acetate solution was washed with a 3% aqueous sodium bicarbonate solution, followed by drying with anhydrous sodium sulfate. This ethyl acetate solution was subjected to reduced pressure to distill off ethyl acetate. To the resultant residue was added 300 ml of n-hexane, and the mixture was stirred to precipitate a crystal. This crystal was filtered, and dried, thereby obtaining 23.9 g of Intermediate D (yield: 78.7%).

Synthesis of Intermediate E

To 59.2 g (0.2 mol) of sodium 3,5-dimethoxycarbonylbenzenesulfonate were added 100 ml of acetonitrile and 60 ml of dimethylacetamide, followed by stirring at room temperature. To this solution, 36 ml of phosphorus oxychloride was added by dropping while the temperature of the reaction solution was adjusted to 40° C. or lower. After completion of the addition, the reaction solution was heated to 40° C. to 45° C. and stirred for 3 hours, to complete the reaction. This reaction solution was cooled to room temperature, and poured into 1,200 ml of ice water to precipitate a crystal. This crystal was filtered, washed with water, and dried, thereby obtaining 43.5 g of Intermediate E (yield: 74.4%).

Synthesis of Intermediate F

To 21.7 g (0.05 mol) of Intermediate D obtained by the aforementioned method was added 65 ml of dimethylacetamide, and the mixture was cooled to 0° C. to 10° C. and stirred. To this solution, 16.8 g (0.0575 mol) of Intermediate E obtained by the aforementioned method was added bit by bit. After completion of the addition, 8.5 ml of triethylamine was added by dropping to the reaction solution. The reaction temperature was retained at 10° C. or lower. After completion of the addition, the reaction solution was stirred at 10° C. or lower for 1 hour, and stirred at room temperature for 2 hours to complete the reaction. This reaction solution was poured into 1,200 ml of water while stirring, to precipitate a crystal. This crystal was filtered, washed with water, and dried, thereby obtaining 30.6 g of Intermediate F (yield: 88.7%).

Synthesis of Intermediate G

To 34.5 g (0.05 mol) of Intermediate F obtained by the aforementioned method was added 350 ml of methanol, and the mixture was stirred at room temperature. To this solution was added 150 ml of a 10% aqueous sodium hydroxide solution. After completion of the addition, the mixture was stirred at room temperature for 3 hours to complete the reaction. After completion of the reaction, 1,000 ml of water was added to this reaction solution, and the resultant solution was neutralized using an aqueous 35% hydrochloric acid solution. The precipitated crystal was filtered, washed with water, and dried, thereby obtaining 28.4 g of Intermediate G (yield: 85.8%).

Synthesis of Intermediate H

To 34.9 g (0.1 mol) of Intermediate B was added 100 ml of N-methylpyrrolidone, and the mixture was cooled to 5° C. to 10° C. and stirred. To this solution, 14.5 g (0.12 mol) of pivaloyl chloride was added by dropping. After completion of the addition, the mixture was stirred at 5° C. to 10° C. for 2 hours to complete the reaction. After completion of the reaction, this reaction solution was poured into 1,000 ml of water while stirring, to precipitate a crystal. This crystal was filtered, washed with water, and dried, thereby obtaining 36.2 g of Intermediate H (83.7%).

Synthesis of Intermediate I

Dimethylacetamide (30 ml) was cooled to 0° C. to 5° C., followed by stirring. To this solution, 20 g of phosphorus oxychloride was added by dropping. After completion of the addition, the mixture was stirred at 0° C. to 5° C. for 1 hour. Then, to this solution, a solution in which 36.2 g (0/126 mol) of Intermediate H obtained by the aforementioned method had been dissolved in 100 ml of dimethylacetamide was added by dropping. After completion of the addition, 20 ml of phosphorus oxychloride was further added by dropping. After completion of the addition, the mixture was stirred at 10° or lower for 2 hours to complete the reaction. After completion of the reaction, this reaction solution was poured into 1,500 ml of water under stirring, and then, a 10% sodium hydroxide aqueous solution was added to adjust the pH of the solution to 9 to 10. This solution was stirred at room temperature for 2 hours to complete the reaction. After completion of the reaction, the reaction solution was neutralized with an aqueous 35% hydrochloric acid solution, and subjected to extraction by adding 250 ml of ethyl acetate. This ethyl acetate solution was washed with an aqueous saturated sodium chloride solution, and dried with anhydrous sodium sulfate. Ethyl acetate was distilled off under reduced pressure, and 100 ml of acetonitrile was added to the residue to precipitate a crystal. This crystal was filtered, and dried, thereby obtaining Intermediate I at 28.0% (quantitative).

Synthesis of Intermediate J

To 18.4 g (0.04 mol) of Intermediate I obtained by the aforementioned method were added 36.0 ml of acetic anhydride and 13.5 g of trifluoroacetic acid, and the mixture was cooled to 5° C. to 10° C. and stirred. To this solution, 26.5 g (0.04 mol) of Intermediate G obtained by the aforementioned method was slowly added in several portions. After completion of the addition, the reaction solution was adjusted to room temperature, and stirred for 2 hours to complete the reaction. After completion of the reaction, this reaction solution was slowly poured into an aqueous solution obtained by adding 1,500 ml of water to 100 g of sodium bicarbonate, while stirring. Then, to this solution were added 300 ml of ethyl acetate and 100 ml of acetonitrile, and the mixture was stirred at room temperature for 2 hours. Then, 35% hydrochloric acid was added to this solution for neutralization, and the resultant mixture was subjected to extraction. This ethyl acetate solution was washed with water, and dried with anhydrous sodium sulfate. Ethyl acetate was distilled off under reduced pressure, and the residue was separated and purified by silica gel column chromatography (eluent: ethyl acetate). The eluant was concentrated, and to the residue was added 100 ml of acetonitrile to precipitate a crystal. This crystal was filtered and dried, thereby obtaining 25.8 g of Intermediate J (yield: 58.3%).

Synthesis of Exemplified Compound A-3

To 11.0 g (0.01 mol) obtained by the aforementioned method was added 100 ml of methanol, and the mixture was stirred at room temperature. To this solution was added 2.20 g of zinc acetate dihydrate, and the mixture was stirred at room temperature for 3 hours. Then, 50 ml of acetonitrile was slowly added by dropping to the reaction solution to precipitate a crystal. This crystal was filtered, and dried, thereby obtaining 10.2 g of Exemplified Compound A-3 (yield: 87.3%).

An absorption spectrum of Exemplified Compound A-3 in an ethyl acetate solution was measured. As a result, a maximum adsorption wavelength (λmax) in a visible region was 533.4 nm, and a molar absorption coefficient (ε) was 114100.

Synthesis Example A2

Synthesis of Exemplified Compound A-38

According to the following reaction scheme B1, Exemplified Compound A-38 was synthesized.

Reaction Scheme B1

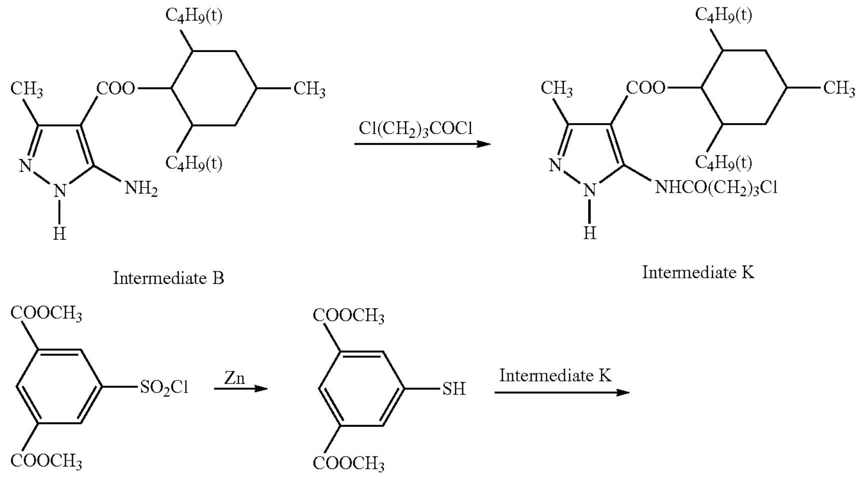

Intermediate B

Intermediate K

Intermediate E

Intermediate L

-continued

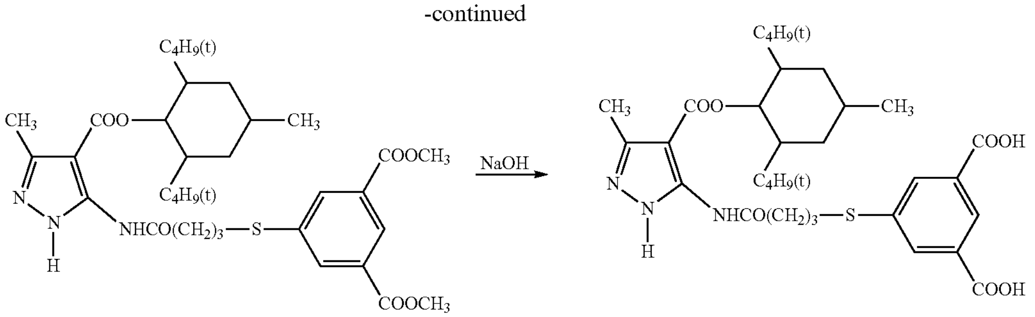

Intermediate M

Intermediate N

Intermediate I

+

Intermediate N

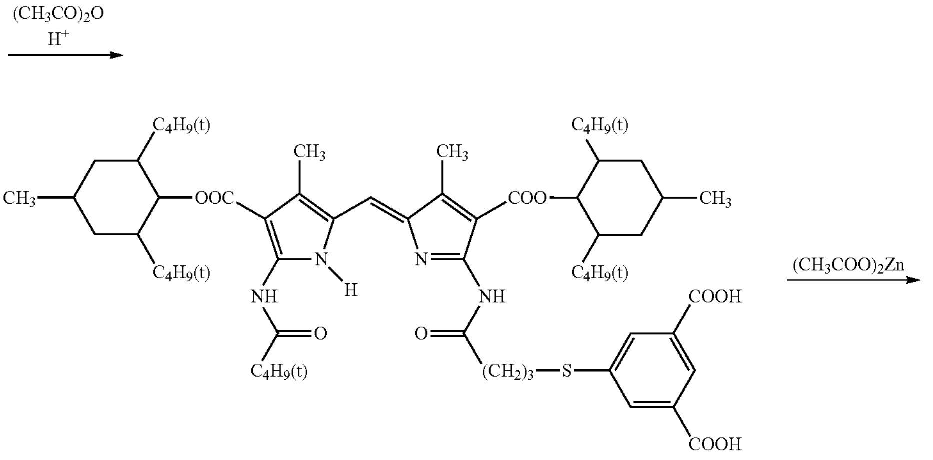

Intermediate O

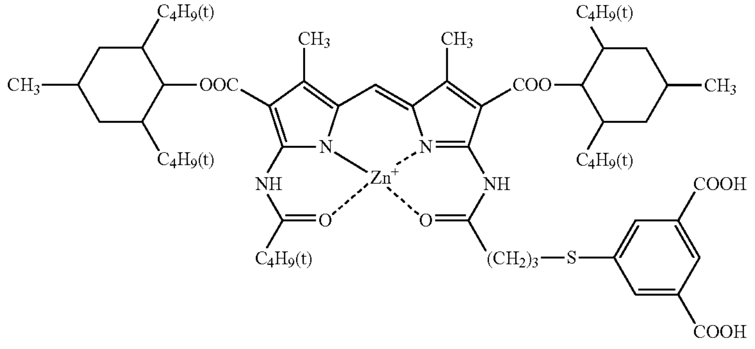

Exemplified Compound A-38

Synthesis of Intermediate K

To 34.8 g (0.1 mol) of Intermediate B was added 150 ml of N-methylpyrrolidone, and the mixture was cooled to 5° C. to 10° C., and stirred. To this solution, 14.8 g (0.105 mol) of 4-chlorobutanoic acid chloride was added by dropping. After completion of the addition, the temperature of the solution was returned to room temperature, and stirring was performed for 2 hours to complete the reaction. After completion of the reaction, the reaction solution was poured into 1,500 ml of water while stirring, to precipitate a crystal. This crystal was filtered, washed with water, and dried, thereby obtaining 42.4 g of Intermediate K (yield: 93.6%).

Synthesis of Intermediate L

To 75 g of a zinc powder was added 450 ml of methanol, and the mixture was cooled to 0° C. to 5° C. and stirred. To this dispersion was added 47.5 g (0.162 mol) of Intermediate E. After completion of the addition, 36.5 ml of concentrated sulfuric acid was slowly added thereto by dropping. After completion of the addition, the mixture was stirred at 10° C. to 15° C. for 1 hour, stirred at room temperature for 1 hour, and then stirred for 1 hour under heating refluxing. Then, 35 ml of concentrated sulfuric acid was slowly added thereto by dropping. After completion of the addition, stirring under heating refluxing was performed for 2 hours to complete the reaction. After completion of the reaction, the reaction solution was cooled to room temperature, and poured into 1,500 ml of water to precipitate a crystal. This crystal was filtered, and washed with water. This crystal was dissolved in 500 ml of ethyl acetate, and the mixture was subjected to filtration to remove insolubles (i.e., Zn). The resultant ethyl acetate solution was concentrated to dryness under reduced pressure, and the residue was crystallized, thereby obtaining 30.6 g of Intermediate L (yield: 83.5%).

Synthesis of Intermediate M

To 27.2 g (0.06 mol) of Intermediate K and 15.6 g (0.069 mol) of Intermediate L obtained by the aforementioned methods were added 100 ml of dimethylacetamide, and the mixture was stirred at room temperature. To this solution, 11.0 g of 1,8-diazabicyclo[5.4.0]-7-undecene (DBU) was added by dropping. After completion of the addition, the mixture was stirred at room temperature for 3 hours to complete the reaction. After completion of the reaction, this reaction solution was poured into 1,000 ml of water while stirring, and then, 35% hydrochloric acid was added thereto to adjust the pH of the solution to 4. The precipitated crystal was filtered, washed with water, and dried, thereby obtaining 28.3 g of Intermediate M (yield: 73.4%).

Synthesis of Intermediate N

To 19.3 g (0.03 mol) of Intermediate M obtained by the aforementioned method was added 200 ml of methanol, and the mixture was stirred at room temperature. To this solution was added an aqueous solution obtained by dissolving 7.2 g of sodium hydroxide in 75 ml of water. After completion of the addition, the mixture was stirred at room temperature for 3 hours to complete the reaction. After completion of the reaction, 35% hydrochloric acid was added to the reaction solution to adjust the pH of the solution to 3. The precipitated crystal was filtered, washed with water, and dried, thereby obtaining 15.8 g of Intermediate N (yield: 85.9%).

Synthesis of Intermediate O

To 18.4 g (0.04 mol) of Intermediate I were added 80.0 ml of acetic anhydride and 15.0 g of trifluoroacetic acid, and the mixture was cooled to 5° C. to 10° C. and stirred. To this solution, 24.6 g (0.04 mol) of Intermediate N obtained by the aforementioned method was slowly added in several portions. After completion of the addition, the reaction solution was adjusted to room temperature, and stirred for 2 hours to complete the reaction. After completion of the reaction, this reaction solution was slowly poured into an aqueous solution obtained by adding 2,000 ml of water to 180 g of sodium dicarbonate, while stirring. Then, to this solution were added 300 ml of ethyl acetate and 100 ml of acetonitrile, and the mixture was stirred at room temperature for 2 hours. Then, to this solution was added 35% hydrochloric acid to neutralize, followed by extraction. This ethyl acetate solution was washed with water, and dried with anhydrous sodium sulfate. Ethyl acetate was distilled off under reduced pressure, and the residue was separated and purified by silica gel column chromatography (eluent: ethyl acetate). The eluant was concentrated, and acetonitrile was added to the residue to precipitate a crystal. This crystal was filtered, and dried, thereby obtaining 22.3 g of Intermediate O (yield: 52.7%).

Synthesis of Exemplified Compound A-38

To 10.6 g (0.01 mol) of Intermediate O obtained by the aforementioned method was added 100 ml of methanol, and the mixture was stirred at room temperature. To this solution was added 2.2 g of zinc acetate dihydrate, and the mixture was stirred at room temperature for 3 hours. Then, to this reaction solution, 100 ml of acetonitrile was slowly added by dropping to precipitate a crystal. This crystal was filtered, and dried, thereby obtaining 9.4 g of Exemplified Compound A-38 (yield: 83.9%).

An absorption spectrum of Exemplified Compound A-38 in an ethyl acetate solution was measured. As a result, a maximum absorption wavelength (λmax) in a visible region was 533.8 nm, and a molar absorption coefficient (ε) was 131100.

Synthesis Examples A3 to A18

Molar absorption coefficients of Exemplified Compounds synthesized according to the methods of Synthesis Example A1 and Synthesis Example A2 in an ethyl acetate solution were measured using a spectrophotometer UV-2400PC (trade name, manufactured by Shimadzu Corporation). Maximum absorption wavelengths (λmax) and molar absorption coefficients (ε) are shown in the following Table 1.

Example 1

The following Exemplified Compounds were produced in accordance with the aforementioned Reaction Schemes, and molar absorption coefficients thereof in an organic solution (organic solvent: ethyl acetate) were respectively measured using a spectrophotometer UV-2400PC (trade name, manufactured by Shimadzu Corporation). The maximum absorption wavelengths (λmax) and molar absorption coefficients (ε) are shown in the following Table 1. In addition, absorbance (Abs) at a measured maximum absorption wavelength (λmax) of each colorant was normalized to 1.0, and absorption at 450 nm was assessed. Results are shown in Table 1.

TABLE 1

| Exemplified Compound No. | λmax (nm) | ε | Abs value at 450 nm when normalized with Abs = 1.0 at λmax |
|---|---|---|---|
| A-1 | 532.8 nm | 121000 | 0.010 |
| A-2 | 533.3 nm | 118300 | 0.013 |
| A-3 | 533.4 nm | 114100 | 0.011 |
| A-7 | 533.0 nm | 117100 | 0.011 |
| A-21 | 534.2 nm | 123000 | 0.010 |
| A-29 | 538.7 nm | 128300 | 0.009 |
| A-34 | 540.2 nm | 107900 | 0.012 |
| A-38 | 533.8 nm | 131100 | 0.011 |
| A-42 | 546.8 nm | 118200 | 0.007 |
| A-43 | 540.5 nm | 105800 | 0.012 |
| D-1 | 523.3 nm | 82600 | 0.011 |
| D-2 | 562.6 nm | 82700 | 0.010 |
| D-6 | 561.4 nm | 94200 | 0.018 |
| D-11 | 538.3 nm | 87000 | 0.015 |
| G-13 | 533.5 nm | 119500 | 0.008 |
| G-17 | 533.8 nm | 120800 | 0.009 |
| H-1 | 532.1 nm | 109800 | 0.008 |
| H-3 | 532.5 nm | 113100 | 0.008 |
| H-11 | 549.0 nm | 132600 | 0.007 |
| H-12 | 549.3 nm | 128100 | 0.009 |
| H-13 | 546.3 nm | 145700 | 0.012 |
| H-14 | 548.5 nm | 127400 | 0.009 |

The results of Table 1 show that the compounds of the invention have high molar absorption coefficients, and low absorbances at 450 nm, and are excellent in color separation, and each are a compound suitable for a color filter.

Example 2

1) Preparation of Resist Solution

The following compounds were mixed and dissolved to prepare a resist solution.

| | |
|---|---|
| Propylene glycol monomethyl ether acetate (PGMEA) | 5.20 parts |
| Cyclohexanone | 52.6 parts |
| Binder: (benzyl methacrylate/methacrylic acid/2-hydroxyethyl methacrylate) copolymer (molar ratio = 60:20:20) 41% ethyl lactate solution (EL solution) | 30.5 parts |
| Dipentaerythritol hexaacrylate | 10.2 parts |
| Polymerization inhibitor (p-methoxyphenol) | 0.006 part |
| Fluorine-containing surfactant | 0.80 part |
| Photopolymerization initiator (TAZ-107, trade name, manufactured by Midori Kagaku Co. Ltd.) | 0.58 part |

2) Preparation of Glass Substrate Having Undercoat Layer

A glass substrate (Corning 1737) was ultrasonicated in 0.5% aqueous NaOH solution, washed with water, dehydrated, and baked at 200° C. for 20 minutes.

The resist solution of section 1) was then applied on the clean glass substrate to a film thickness of 2.0 μm using a spin coater, and the plate was dried under heat at 220° C. for 1 hour, to prepare a cured film (i.e., undercoat layer).

3) Preparation of Colored Resist Solution (Negative-Working Colored Curable Composition)

Compounds described in the following formulation were mixed and dissolve to prepare a colored curable composition X-1.

Colored Curable Composition X-1

| | |
|---|---|
| Ethyl lactate | 40 parts |
| Methyl isobutyl ketone | 40 parts |
| Exemplified Compound (A-1) | 2.95 parts |
| Polymerizable compound (KARAYAD DPHA manufactured by Nippon Kayaku Co., Ltd.) | 5.89 parts |
| Photopolymerization initiator (CGI-242, manufactured by Ciba Specialty Chemicals) | 1.50 parts |
| Surfactant (F-781, manufactured by DIC Corporation) | 0.02 part |

4) Coating, Light Exposure, and Development of Colored Resist Solution (Negative-Working Colored Curable Composition)

The colored curable composition X-1 prepared in section 3) was applied on the undercoat layer of the glass substrate having an undercoat layer, which had been obtained in section 2), using a spin coater so that a dry thickness of this coated film became 1.0 μm, to form a photocurable coated film. Then, heat treatment (pre-baking) was performed for 120 seconds using a hot plate at 100° C. to produce colored filters having any one color from magenta to violet.

Then, using a light exposing apparatus, the coated film was irradiated with a light at a wavelength of 365 nm at an exposure amount of 500 $mJ/cm^2$ through a mask of a line width of 2 mm. After the exposure, using a 60% CD-2000 developer (manufactured by Fuji Film Electronics Materials), and a 6% CD-2000 developer obtained by diluting 10-fold a 60% CD-2000 with water, the film was developed under the conditions of 25° C. and 40 seconds, respectively. Thereafter, the film was rinsed with flowing water for 30 seconds, and spray-dried.

By the above procedure, a pattern suitable for a coloring color filter was obtained.

5) Evaluation

Storage stability of the colored resist solution prepared above, and spectroscopic properties of the coated film applied on the glass substrate using the colored resist solution were evaluated. In addition, developability at use of the 60% CD-2000 developer, and developability at use of the 6% developer were evaluated. Evaluation results are shown in Table 2.

Storage Stability

After the colored resist solution was stored at room temperature for one month, a precipitation degree of a foreign matter therein was assessed by visual observation according to the following evaluation criteria.

Evaluation Criteria

A: No precipitation was recognized.

B: Slight precipitation was recognized.

C: Precipitation was recognized.

Transmittance Evaluation

A transmission spectrum of the color filter obtained above was measured, and a transmittance at 450 nm was assessed. The larger transmittance indicates a higher amount of transmission of blue light, and indicates that the colorant is excellent as a magenta to violet colorant (i.e., a colorant having any one color from magenta to violet) usable in a blue color filter.

Evaluation Criteria

A transmittance at 450 nm when a transmittance at a maximum absorption wavelength of each colorant was corrected (normalized) to 5% was determined.

A: transmittance at 450 nm≥90%

B: 80%≤transmittance at 450 nm<90%

C: transmittance at 450 nm<80%

Evaluation of Developability

An absorbance at 550 nm of an unexposed area when the 60% CD-2000 was used as the developer, and an absorbance at 550 nm of an unexposed area when the developer diluted to 6% was used were assessed. That is, in the color filter using the colored curable composition having good developability, a colored substance does not remain at an unexposed area, and alkali developability is excellent; as a result, an absorbance at 550 nm is reduced.

Evaluation Criteria

A: absorbance at 550 nm<0.01

B: 0.01≤absorbance at 550 nm<0.1

C: 0.1≤absorbance at 550 nm

Examples 3 to 36

Examples 3 to 36 were performed in the same manner as those of Example 2 except that Exemplified Compound A-1 used in section 3) "preparation of colored resist solution" of Example 2 was replaced with an equivalent mol of Exemplified Compounds shown in the following Table 2, respectively. Results are shown in Table 2.

Comparative Examples 1 to 4

Comparative Examples 1 to 4 were performed in the same manner as those of Example 2 except that Exemplified Compound A-1 used in section 3) "preparation of colored resist solution" of Example 2 was replaced with an equivalent mol of the compounds shown in the following Table 2, respectively. Results are shown in Table 2.

Comparative Compound 1

Compound III-1 disclosed in US Patent Application Publication No. 2008/0076044 A1

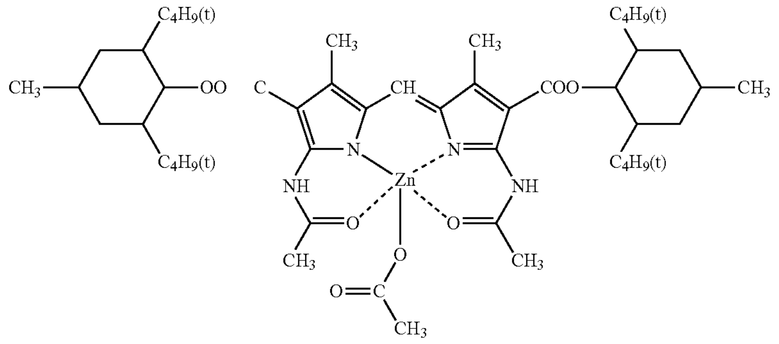

Comparative Compound 2

Compound I-4 disclosed in US Patent Application Publication No. 2008/0076044 A1

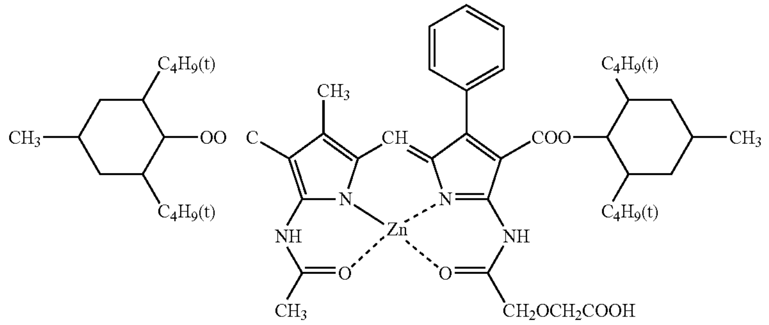

TABLE 2

| | | Storage | | Developer concentration dependency | | |
|---|---|---|---|---|---|---|
| Example No. | Compound No. | stability | Transmittance | 60% CD-2000 | 6% CD-2000 | Remark |
| Example 2 | A-1 | A | A | A | A | Invention |
| Example 3 | A-2 | A | A | A | A | Invention |
| Example 4 | A-3 | A | A | A | A | Invention |
| Example 5 | A-7 | A | A | A | A | Invention |
| Example 6 | A-20 | A | A | A | A | Invention |
| Example 7 | A-21 | A | A | A | A | Invention |
| Example 8 | A-29 | A | A | A | A | Invention |
| Example 9 | A-34 | A | A | A | A | Invention |
| Example 10 | A-38 | A | A | A | A | Invention |
| Example 11 | A-42 | A | A | A | A | Invention |
| Example 12 | A-43 | A | A | A | A | Invention |
| Example 13 | B-1 | A | A | A | A | Invention |
| Example 14 | B-6 | A | A | A | A | Invention |
| Example 15 | B-8 | A | A | A | A | Invention |
| Example 16 | B-9 | B | A | A | A | Invention |
| Example 17 | C-6 | A | A | A | A | Invention |
| Example 18 | D-1 | B | A | A | A | Invention |
| Example 19 | D-2 | A | A | A | A | Invention |
| Example 20 | D-6 | A | A | A | A | Invention |
| Example 21 | D-11 | A | A | A | A | Invention |
| Example 22 | E-6 | B | B | A | A | Invention |
| Example 23 | E-10 | B | B | A | A | Invention |
| Example 24 | F-2 | A | A | A | A | Invention |
| Example 25 | F-5 | B | A | A | A | Invention |
| Example 26 | F-12 | A | A | A | A | Invention |
| Example 27 | F-13 | A | A | A | A | Invention |
| Example 28 | G-1 | A | A | A | A | Invention |
| Example 29 | G-2 | A | A | A | A | Invention |
| Example 30 | G-11 | A | B | A | A | Invention |
| Example 31 | G-13 | A | A | A | A | Invention |
| Example 32 | G-17 | A | A | A | A | Invention |

TABLE 2-continued

| Example No. | Compound No. | Storage stability | Transmittance | Developer concentration dependency 60% CD-2000 | 6% CD-2000 | Remark |
|---|---|---|---|---|---|---|
| Example 33 | G-18 | B | B | A | A | Invention |
| Example 34 | G-19 | B | B | A | A | Invention |
| Example 35 | H-1 | A | A | A | A | Invention |
| Example 36 | H-3 | A | A | A | A | Invention |
| Example 37 | H-11 | A | A | A | A | Invention |
| Example 38 | H-12 | A | A | A | A | Invention |
| Example 39 | H-13 | A | B | A | A | Invention |
| Example 40 | H-14 | B | A | A | A | Invention |
| Comparative Example 1 | C. I. Acid Violet-17 | C | C | A | B | Comparative Example |
| Comparative Example 2 | C. I. Acid Violet 49 | C | C | A | C | Comparative Example |
| Comparative Example 3 | Comparative compound 1 | A | A | C | C | Comparative Example |
| Comparative Example 4 | Comparative compound 2 | A | A | C | C | Comparative Example |

The results of Table 2 show that the colored curable compositions including the coloring agent of the invention have excellent storage properties in a resist solution, and the coated films formed from the compositions become a film suitable for a color filter, which is excellent in spectroscopic property (color separation). In addition, it was seen that there is no developer concentration dependency, and pattern forming property (developability) is excellent.

Examples 37 to 72

Coating, Light Exposure and Development of Resist Solution (Image Formation)

1) Production of Silicon Wafer Substrate Having Undercoat Layer

A six-inch silicon wafer was heat-treated in an oven at 200° C. for 30 minutes. Then, this silicon wafer was coated with the resist solution prepared in section 1) of Example 2 so that a dry film thickness became 1.0 μm. The wafer was dried in an oven at 220° C. for 1 hour to form an undercoat layer, thereby obtaining a silicon wafer substrate having an undercoat layer.

The colored curable compositions of Examples 2 to 37 were each applied on the undercoat layer of the silicon wafer substrate having an undercoat layer obtained section 1) so that a dry thickness of each coated film became 0.8 μm, to form a photocurable coated film. Then, heat treatment (pre-baking) was performed using a hot plate at 100° C. for 120 seconds. Then, using an i-ray stepper light exposing apparatus (FPA-3000i5+, manufactured by Canon), the film was irradiated with light having a wavelength of 365 nm through an island pattern mask having a pattern of 1.2 $\mu m^2$ in such a manner that the exposure amount was changed by 100 $mJ/cm^2$ within a range of from 100 to 2500 $mJ/cm^2$. Thereafter, a silicon wafer substrate on which the irradiated coated film had been formed was placed on a horizontal rotating table of a spin shower developing machine (DW-30, manufactured by Chemitronics Co., Ltd.), and paddle development was performed at 23° C. for 60 seconds using 60% CD-2000 (manufactured by Fuji Film Electronics Materials) to form a colored pattern on a silicon wafer substrate.

Formation of Color Filter

The silicon wafer substrate on which the colored pattern had been formed was fixed on the horizontal rotating table in a vacuum chuck manner, pure water was supplied from an ejection nozzle by showering from above a rotation center to perform rinse treatment while the silicon wafer substrate is rotated with a rotating device at a rotation number of 50 rpm, and thereafter, this was spray-dried, thereby obtaining a color filter.

The formed pattern image having any one color from magenta to violet showed such a good profile that it had a rectangular cross-section of a square, which is suitable for an imaging device.

Example 73

1) Preparation of Positive-Working Colored Curable Composition

| | |
|---|---|
| Ethyl lactate (EL) | 30 parts |
| Resin P-1 (described below) | 3.0 parts |
| Naphthoquinone diazide compound N-1 (described below) | 1.8 parts |
| Crosslinking agent: hexamethoxymethylolated melamine | 0.6 part |
| Photo acid generator: TAZ-107 (manufactured by Midori Kagaku Co., Ltd) | 1.2 parts |
| Fluorine-containing surfactant (F-475, manufactured by DIC) | 0.0005 part |
| Colorant: Exemplified Compound A-3 (compound of the invention) | 0.3 part |

These compounds were mixed and dissolved, to obtain a positive-working colored curable composition.

The positive-working colored curable composition thus obtained was evaluated in the same manner as that of Example 2. As a result, the positive-working colored curable composition was found to have excellent storage stability and excellent transmittance.

Resin P-1 and the naphthoquinonediazide compound (N-1) were synthesized in the following manners.

2) Synthesis of Resin P-1

70.0 g of benzyl methacrylate, 13.0 g of methacrylic acid, 17.0 g of 2-hydroxyethyl methacrylate, and 600 g of 2-methoxypropanol were placed in a three-neck flask which was attached with a stirrer, a reflux condenser tube, and a thermometer. The mixture was mixed with a catalytic quantity of a polymerization initiator (trade name: V-65, made by Wako Pure Chemical Industries, Inc.), and was stirred for 10 hours at 65° C. in a nitrogen stream. The resin solution obtained was dripped into 20 L of ion-exchange water with vigorous stirring, and a white powder was obtained. The white powder was dried at 40° C. for 24 hours in a vacuum, and 145 g of Resin P-1 was obtained. The molecular weight was measured by GPC, which showed the weight average molecular weight Mw=28,000, and number average molecular weight Mn=11,000.

3) Synthesis of Naphthoquinone Diazide Compound (N-1)

42.45 g of Trisp-PA (made by Honshu Chemical Co.), 61.80 g of o-naphthoquinone diazide-5-sulfonylchloride, and 300 ml of acetone were placed in a three-neck flask, into which 24.44 g of triethylamine was added by dropping at room temperature for 1 hour. After the dripping, it was stirred for another 2 hours. Then, the reaction solution was poured into a large volume of water with stirring. Precipitated naphthoquinone diazide sulfonic acid ester was collected by suction filtration, and dried in a vacuum at 40° C. for 24 hours, to obtain photosensitive compound N-1.

Examples Relating to Second Exemplary Embodiment

Compounds represented by Formula (A2), Formulae (B2), Formula (C2) and Formula (D2), respectively, may be synthesized by the method described in US Patent Application Publication No. 2008/0076044 A1.

A method of synthesizing a dipyrromethene metal complex compound according to the second exemplary embodiment of the invention is described in detail by referring to the following Reaction Scheme A2 using an example of synthesis of Exemplified Compound A'-3.

Reaction Scheme A2

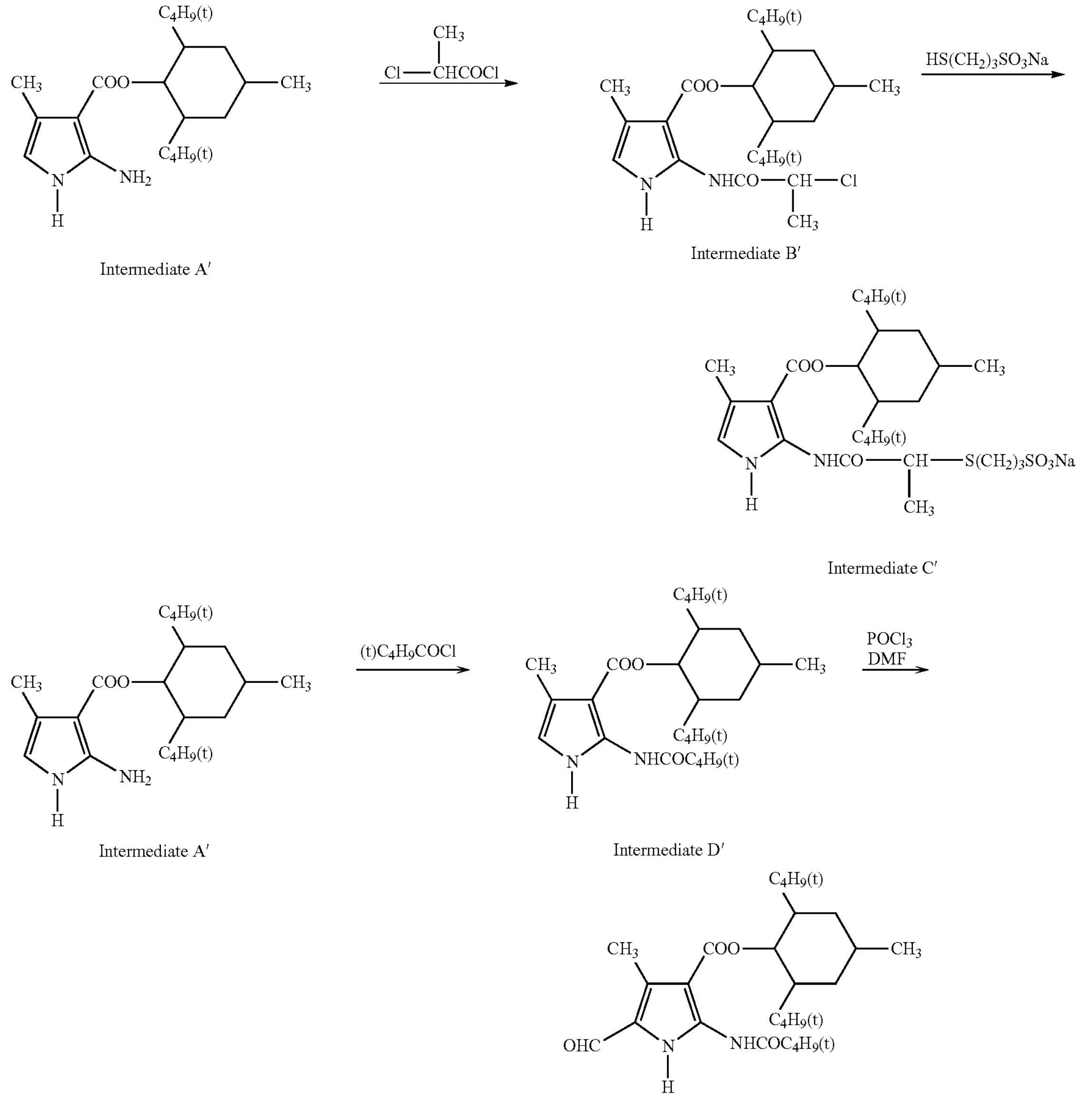

Intermediate A' → Intermediate B' → Intermediate C'

Intermediate A' → Intermediate D' → Intermediate E'

-continued

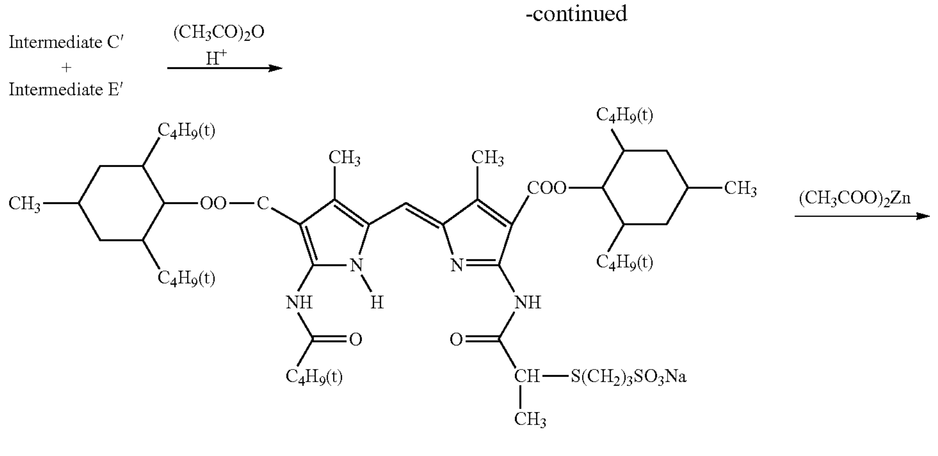

Intermediate F′

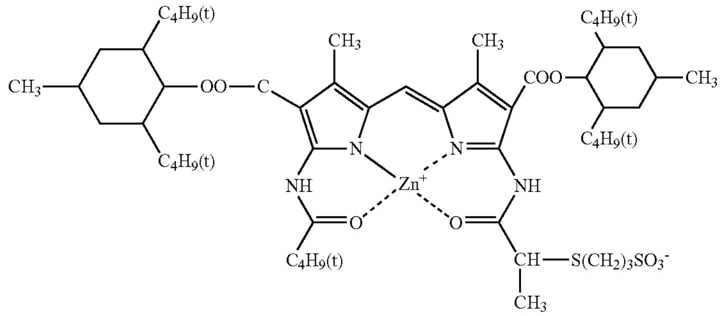

Exemplified Compound A′-3

Synthesis Example B1

Synthesis of Exemplified Compound A'-3

Synthesis of Intermediate B'

To 17.4 g (0.05 mol) of Intermediate A' synthesized according to a method described in JP-A No. 10-316654 was added 50 ml of N-methylpyrrolidone (NMP), and the mixture was cooled to 5° C. and stirred. To this solution, 7.62 g (0.06 mol) of 2-chloropropionyl chloride was added by dropping. After completion of the addition, this reaction solution was poured into 800 ml of water while stirring, to precipitate a crystal. The crystal was filtered, and washed with water. Then, this crystal was dispersed in 250 ml of acetonitrile, and the dispersion was stirred for 2 hours, and subjected to filtration, thereby obtaining 16.5 g of Intermediate B' (yield: 75.2%).

Synthesis of Intermediate C'

To 13.0 g (0.03 mol) of the intermediate B' obtained by the aforementioned method and 8.0 g (0.045 mol) of sodium 3-mercaptopropanesulfonate was added 50 ml of NMP, and the mixture was stirred under a nitrogen stream. To this dispersion, 5.5 g (0.036 mol) of 1,8-diazabicyclo[5.4.0]-7-undecene (DBU) was added by dropping. After completion of the addition, the mixture was stirred at room temperature for 4 hours to complete the reaction. After completion of the reaction, this reaction solution was poured into 700 ml of an aqueous saturated sodium chloride solution and 500 ml of ethyl acetate while stirring. The aqueous sodium chloride solution was removed, and the ethyl acetate solution was washed with an aqueous saturated sodium chloride solution, followed by drying with anhydrous sodium sulfate. Ethyl acetate was concentrated under reduced pressure, and 500 ml of acetonitrile was added to the residue to precipitate a crystal. This crystal was filtered, and dried, thereby obtaining 16.9 g of Intermediate C' (yield: 97.1%).

Synthesis of Intermediate D'

To 34.9 g (0.1 mol) of Intermediate A' synthesized according to the method described in JP-A No. 10-316654 was added 100 ml of NMP, and the mixture was cooled to 10° C. and stirred. To this solution, 14.5 g (0.12 mol) of pivaloyl chloride was added by dropping. After completion of the addition, the mixture was stirred at room temperature for 2 hours to complete the reaction. This reaction solution was poured into 1,000 ml of water while stirring, to precipitate a crystal. This crystal was filtered, washed with water, and dried. To this crystal was added 500 ml of acetonitrile, and the mixture was heated to 50° C., followed by stirring for 1 hour. This dispersion was cooled to room temperature, filtered, and dried, thereby obtaining 36.2 g of Intermediate D' (yield: 83.7%).

Synthesis of Intermediate E'

Dimethylformamide (DMF) (100 ml) was cooled to 5° C., and 19.3 g of phosphorus oxychloride was added by dropping thereto while stirring. After completion of the addition, the mixture was stirred at 5 C to 10° C. for 1 hour, and a solution obtained by dissolving 36.2 g (0.084 mol) of Intermediate D' obtained by the aforementioned method in 100 ml of DMF was added by dropping thereto. After the mixture was stirred at 10° C. to 15° C. for 1 hour, 19.3 g of phosphorus oxychloride was further added by dropping thereto. After completion of the addition, the mixture was stirred at 10° C. to 15° C. for 2 hours to complete the reaction. After completion of the reaction, this reaction solution was poured into 1,000 ml of water while stirring. Then, to this aqueous solution was added by dropping an aqueous solution obtained by dissolving 40 g of sodium hydroxide in 300 ml of water, until the pH of the solution became 7. After completion of the addition, the mixture was stirred at room temperature for 2 hours to precipitate a crystal, and the crystal was filtered, washed with water, and dried, thereby obtaining 40.0 g of dimethylaminomethylene of Intermediate D'. To 40.0 g of this dimethylaminomethylene were added 150 ml of ethyl acetate, 30 ml of methanol and 200 ml of water, and the mixture was stirred at room temperature. To this solution was added 8.5 g of potassium carbonate, and the mixture was heated to 35° C. to 40° C., and stirred for 2 hours. After completion of the reaction, to this reaction solution was added 35% hydrochloric acid so that the pH of the solution became from 3 to 4. Then, the ethyl acetate phase was washed with an aqueous saturated sodium chloride solution, and dried with anhydrous sodium sulfate. Ethyl acetate was concentrated to dryness under reduced pressure. To the residue was added 100 ml of acetonitrile to precipitate a crystal, which was filtered, and dried, there by obtaining 36.6 g of Intermediate E (yield: 95.0%).

Synthesis of Intermediate F'

To 4.61 g (0.01 mol) of Intermediate E' obtained by the aforementioned method were added 50 ml of acetic anhydride and 3.5 g of trifluoroacetic acid, and the mixture was cooled to 5° C. to 10° C. and stirred. To this solution, 5.81 g (0.01 mol) of Intermediate F obtained by the aforementioned method was slowly added in portions. After completion of the addition, the mixture was stirred at room temperature for 2 hours to complete the reaction. After completion of the reaction, this reaction solution was slowly added by dropping to an aqueous solution obtained by dissolving 84 g of sodium bicarbonate in 1,000 ml of water. The precipitated crystal was filtered, washed with water, and dried. To this crystal was added a mixed solvent of 50 ml of acetonitrile and 25 ml of ethyl acetate and dispersed therein at room temperature, and the mixture was stirred for 2 hours. The resultant crystal was filtered, and dried, thereby obtaining 7.88 g of Intermediate F' (yield: 77.0%).

λmax in an ethyl acetate solution was 507.1 nm, and a molar absorption coefficient (8) was 55600.

Synthesis of Exemplified Compound A'-3

To 1.18 g of zinc acetate dihydrate was added 150 ml of 2-propanol, and the mixture was stirred at room temperature. To this dispersion was added 5.0 g (0.0049 mol) of Intermediate F' obtained by the aforementioned method. After completion of the addition, the mixture was stirred at room temperature for 3 hours to complete the reaction. To this solution, 100 ml of acetonitrile was slowly added by dropping, and the mixture was stirred for 4 hours. The resultant crystal was filtered, washed with acetonitrile, and dried, thereby obtaining 4.25 g of Exemplified Compound A'-3 (yield: 81.6%).

λmax of Exemplified Compound A'-3 in an ethyl acetate solution was 535.0 nm, and a molar absorption coefficient (ϵ) was 140800.

Example 1B

1) Preparation of Resist Solution

The following compounds were mixed and dissolved to prepare a resist solution.

| | |
|---|---|
| Propylene glycol monomethyl ether acetate (PGMEA) | 5.20 parts |
| Cyclohexanone | 52.6 parts |
| Binder: (benzyl methacrylate/methacrylic acid/2-hydroxyethyl methacrylate) copolymer (molar ratio = 60:20:20) 41% ethyl lactate solution (EL solution) | 30.5 parts |
| Dipentaerythritol hexaacrylate | 10.2 parts |
| Polymerization inhibitor (p-methoxyphenol) | 0.006 part |
| Fluorine-containing surfactant | 0.80 part |
| Photopolymerization initiator (TAZ-107, trade name, manufactured by Midori Kagaku Co. Ltd.) | 0.58 part |

2) Preparation of Glass Substrate Having Undercoat Layer

A glass substrate (Corning 1737) was ultrasonicated in 0.5% aqueous NaOH solution, washed with water, dehydrated, and baked at 200° C. for 20 minutes.

The resist solution of section 1) was then applied on the clean glass substrate to a film thickness of 2.0 μm using a spin coater, and the plate was dried under heat at 220° C. for 1 hour, to prepare a cured film (i.e., undercoat layer).

3) Preparation of Colored Resist Solution (Negative-Working Colored Curable Composition)

Compounds described in the following formulation were mixed and dissolve to prepare a colored curable composition X'-1.

Colored Curable Composition X'-1

| | |
|---|---|
| Ethyl lactate | 20 parts |
| Methyl isobutyl ketone | 60 parts |
| Exemplified Compound (A'-1) | 4.18 parts |
| Polymerizable compound (KARAYAD DPHA manufactured by Nippon Kayaku Co., Ltd.) | 12.80 parts |
| Photopolymerization initiator (CGI-242, manufactured by Ciba Specialty Chemicals) | 2.00 parts |
| Surfactant (F-781, manufactured by DIC Corporation) | 0.02 part |

4) Coating, Light Exposure, and Development of Colored Resist Solution (Negative-Working Colored Curable Composition)

The colored curable composition X'-1 prepared in section 3) was applied on the undercoat layer of the glass substrate having an undercoat layer, which had been obtained in section 2), using a spin coater so that a dry thickness of this coated film became 1.0 μm, to form a photocurable coated film. Then, heat treatment (pre-baking) was performed for 120 seconds using a hot plate at 100° C. to produce colored filters having any one color from magenta to violet.

Then, using a light exposing apparatus, the coated film was irradiated with a light at a wavelength of 365 nm at an exposure amount of 500 mJ/$cm^2$ through a mask of a line width of 2 mm. After the exposure, using a 60% CD-2000 developer (manufactured by Fuji Film Electronics Materials), and a 6% CD-2000 developer obtained by diluting 10-fold a 60% CD-2000 with water, the film was developed under the conditions of 25° C. and 40 seconds, respectively. Thereafter, the film was rinsed with flowing water for 30 seconds, and spray-dried.

By the above procedure, a pattern suitable for a coloring color filter was obtained.

5) Evaluation

Storage stability of the colored resist solution prepared above, and spectroscopic properties of the coated film applied on the glass substrate using the colored resist solution were evaluated. In addition, developability at use of the 60% CD-2000 developer, and developability at use of the 6% developer were evaluated. Evaluation results are shown in Table 3.

Storage Stability

After the colored resist solution was stored at room temperature for one month, a precipitation degree of a foreign matter therein was assessed by visual observation according to the following evaluation criteria.

Evaluation Criteria

A: No precipitation was recognized.

B: Slight precipitation was recognized.

C: Precipitation was recognized.

Transmittance Evaluation

A transmission spectrum of the color filter obtained above was measured, and a transmittance at 450 nm was assessed. The larger transmittance indicates a higher amount of transmission of blue light, and indicates that the colorant is excellent as a magenta to violet colorant usable in a blue color filter.

Evaluation Criteria

A transmittance at 450 nm when a transmittance at a maximum absorption wavelength of each colorant was corrected (normalized) to 5% was determined.

A: transmittance at 450 nm≥90%

B: 80%≤transmittance at 450 nm<90%

C: transmittance at 450 nm<80%

Evaluation of Developability

An absorbance at 550 nm of an unexposed area when the 60% CD-2000 was used as the developer, and an absorbance at 550 nm of an unexposed area when the developer diluted to 6% was used were assessed. That is, in the color filter using the colored curable composition having good developability, a colored substance does not remain at an unexposed area, and alkali developability is excellent; as a result, an absorbance at 550 nm is reduced.

Evaluation Criteria

A: absorbance at 550 nm<0.01

B: 0.01≤absorbance at 550 nm<0.1

C: 0.1≤absorbance at 550 nm

Examples 2B to 41B

Examples 2B to 41B were performed in the same manner as those of Example 1B except that Exemplified Compound A'-1 used in section 3) "preparation of colored resist solution" of Example 1B was replaced with an equivalent mol of Exemplified Compounds shown in the following Tables 3 and 4, respectively. Results are shown in Tables 3 and 4.

Comparative Examples 1B to 4B

Comparative Examples 1B to 4B were performed in the same manner as those of Example 1B except that Exemplified Compound A'-1 used in section 3) "preparation of colored resist solution" of Example 11B was replaced with an equivalent mol of the compounds shown in the following Table 4, respectively. Results are shown in Table 4.

Comparative Compound A

Exemplified Compound I-3 disclosed in US Patent Application Publication No. 2008/0076044 A1

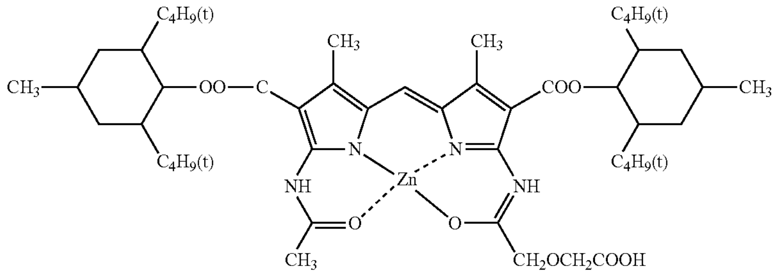

Comparative Compound B

Exemplified Compound III-17 disclosed in US Patent Application Publication No. 2008/0076044 A1

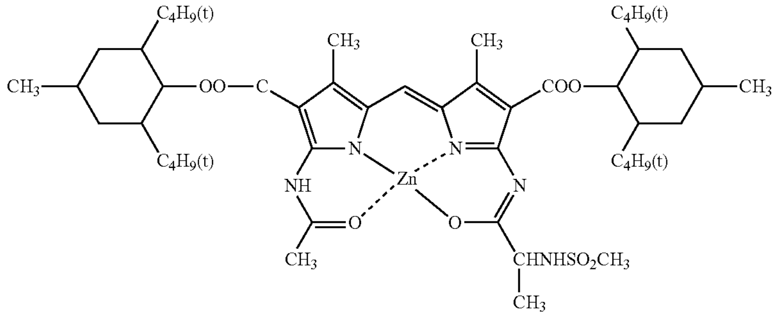

Comparative Compound C

Exemplified Compound III-55 disclosed in US Patent Application Publication No. 2008/0076044 A1

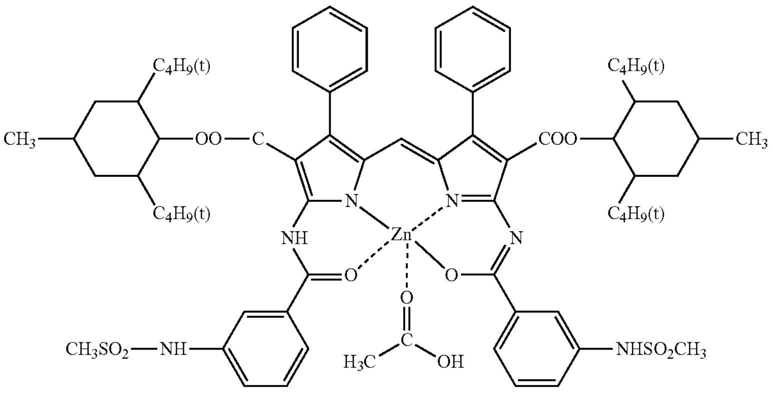

TABLE 3

| Example No. | Compound No. | Storage stability | Trans-mittance | Developer concentration dependency 6% CD-2000 | 6% CD-2000 |
|---|---|---|---|---|---|
| Example 1B | A'-1 | A | A | A | A |
| Example 2B | A'-2 | A | A | A | A |
| Example 3B | A'-3 | A | A | A | A |
| Example 4B | A'-6 | A | A | A | A |
| Example 5B | A'-8 | A | A | A | A |
| Example 6B | A'-11 | A | A | A | A |
| Example 7B | A'-12 | A | A | A | A |
| Example 8B | A'-14 | B | A | A | A |
| Example 9B | A'-17 | A | A | A | A |
| Example 10B | A'-18 | B | A | A | A |
| Example 11B | A'-20 | A | A | A | A |
| Example 12B | A'-23 | A | A | A | A |
| Example 13B | A'-25 | A | A | A | A |
| Example 14B | A'-30 | A | A | A | A |
| Example 15B | A'-33 | A | A | A | A |
| Example 16B | A'-34 | B | A | A | A |
| Example 17B | A'-35 | A | A | A | A |
| Example 18B | A'-42 | B | A | A | A |
| Example 19B | B'-1 | A | A | A | A |
| Example 20B | B'-2 | A | A | A | A |

TABLE 4

| Example No. | Compound No. | Storage stability | Trans-mittance | Developer concentration dependency 6% CD-2000 | 6% CD-2000 |
|---|---|---|---|---|---|
| Example 21B | B'-3 | A | A | A | A |
| Example 22B | B'-7 | A | A | A | A |
| Example 23B | B'-8 | B | A | A | A |
| Example 24B | B'-10 | A | A | A | A |
| Example 25B | B'-12 | A | A | A | A |
| Example 26B | C'-1 | A | A | A | A |
| Example 27B | C'-2 | A | A | A | A |
| Example 28B | C'-3 | A | A | A | A |
| Example 29B | C'-6 | B | A | A | A |
| Example 30B | C'-10 | A | A | A | A |
| Example 31B | D'-1 | B | B | A | A |
| Example 32B | D'-13 | B | B | A | A |
| Example 33B | E'-1 | A | A | A | A |
| Example 34B | E'-2 | A | A | A | A |

TABLE 4-continued

| Example No. | Compound No. | Storage stability | Trans-mittance | Developer concentration dependency 6% CD-2000 | 6% CD-2000 |
|---|---|---|---|---|---|
| Example 35B | E'-8 | B | A | A | A |
| Example 36B | E'-9 | A | A | A | A |
| Example 37B | E'-12 | A | A | A | A |
| Example 38B | F'-2 | A | A | A | A |
| Example 39B | F'-11 | A | A | A | A |
| Example 40B | F'-13 | A | A | A | A |
| Example 41B | F'-14 | A | A | A | A |
| Comparative Example 1B | C.I. Acid Violet-17 | C | C | A | B |
| Comparative Example 2B | Comparative compound A | B | A | A | C |
| Comparative Example 3B | Comparative compound B | A | A | B | C |
| Comparative Example 4B | Comparative compound C | B | A | B | C |

The results of Table 3 and Table 4 show that the colored curable compositions including the coloring agent of the invention have excellent storage properties in a resist solution, and the coated films formed from the compositions become a film suitable for a color filter, which is excellent in spectroscopic property (color separation). In addition, it was seen that there is no developer concentration dependency, and pattern forming property (developability) is excellent.

Examples 42B to 82B

Coating, Light Exposure and Development of Resist Solution (Image Formation)

1) Production of Silicon Wafer Substrate Having Undercoat Layer

A six-inch silicon wafer was heat-treated in an oven at 200° C. for 30 minutes. Then, this silicon wafer was coated with the resist solution prepared in section 1) of Example 1B so that a dry film thickness became 1.0 μm. The wafer was dried in an oven at 220° C. for 1 hour to form an undercoat layer, thereby obtaining a silicon wafer substrate having an undercoat layer.

The colored curable compositions of Examples 1B to 41B were each applied on the undercoat layer of the silicon wafer substrate having an undercoat layer obtained section 1) so that a dry thickness of each coated film became 0.8 μm, to form a photocurable coated film. Then, heat treatment (pre-baking) was performed using a hot plate at 100° C. for 120 seconds. Then, using an i-ray stepper light exposing apparatus (FPA-3000i5+, manufactured by Canon), the film was irradiated with light having a wavelength of 365 nm through an island pattern mask having a pattern of 1.2 $\mu m^2$ in such a manner that the exposure amount was changed by 100 $mJ/cm^2$ within a range of from 100 to 2500 $mJ/cm^2$. Thereafter, a silicon wafer substrate on which the irradiated coated film had been formed was placed on a horizontal rotating table of a spin shower developing machine (DW-30, manufactured by Chemitronics Co., Ltd.), and paddle development was performed at 23° C. for 60 seconds using 60% CD-2000 (manufactured by Fuji Film Electronics Materials) to form a colored pattern on a silicon wafer substrate.

Formation of Color Filter

The silicon wafer substrate on which the colored pattern had been formed was fixed on the horizontal rotating table in a vacuum chuck manner, pure water was supplied from an ejection nozzle by showering from above a rotation center to perform rinse treatment while the silicon wafer substrate is rotated with a rotating device at a rotation number of 50 rpm, and thereafter, this was spray-dried, thereby obtaining a color filter.

The formed pattern image having any one color from magenta to violet showed such a good profile that it had a rectangular cross-section of a square, which is suitable for an imaging device.

Example 83B

1) Preparation of Positive-Working Colored Curable Composition

| | |
|---|---|
| Ethyl lactate (EL) | 30 parts |
| Resin P-1 (described below) | 3.0 parts |
| Naphthoquinone diazide compound N-1 (described below) | 1.8 parts |
| Crosslinking agent: hexamethoxymethylolated melamine | 0.6 part |
| Photo acid generator: TAZ-107 (manufactured by Midori Kagaku Co., Ltd) | 1.2 parts |
| Fluorine-containing surfactant (F-475, manufactured by DIC) | 0.0005 part |
| Colorant: Exemplified Compound A-3 (compound of the invention) | 0.3 part |

These compounds were mixed and dissolved, to obtain a positive-working colored curable composition.

Resin P-1 and the naphthoquinonediazide compound (N-1) were synthesized in the following manners.

2) Synthesis of Resin P-1

70.0 g of benzyl methacrylate, 13.0 g of methacrylic acid, 17.0 g of 2-hydroxyethyl methacrylate, and 600 g of 2-methoxypropanol were placed in a three-neck flask which was attached with a stirrer, a reflux condenser tube, and a thermometer. The mixture was mixed with a catalytic quantity of a polymerization initiator (trade name: V-65, made by Wako Pure Chemical Industries, Inc.), and was stirred for 10 hours at 65° C. in a nitrogen stream. The resin solution obtained was dripped into 20 L of ion-exchange water with vigorous stirring, and a white powder was obtained. The white powder was dried at 40° C. for 24 hours in a vacuum, and 145 g of Resin P-1 was obtained. The molecular weight was measured by GPC, which showed the weight average molecular weight Mw=28,000, and number average molecular weight Mn=11,000.

3) Synthesis of Naphthoquinone Diazide Compound (N-1)

42.45 g of Trisp-PA (made by Honshu Chemical Co.), 61.80 g of o-naphthoquinone diazide-5-sulfonylchloride, and 300 ml of acetone were placed in a three-neck flask, into which 24.44 g of triethylamine was added by dropping at room temperature for 1 hour. After the dripping, it was stirred for another 2 hours. Then, the reaction solution was poured into a large volume of water with stirring. Precipitated naphthoquinone diazide sulfonic acid ester was collected by suction filtration, and dried in a vacuum at 40° C. for 24 hours, to obtain photosensitive compound N-1.

The positive-working colored curable compositions obtained as described above were evaluated in the same manner as in Example 1B. As a result, it was found that storage stability and transmittance are excellent.

What is claimed is:

1. A colored curable composition, comprising:

a polymerizable monomer;

a radiation-sensitive compound; and at least one selected from the group consisting of a compound represented by the following Formula (1-A2) and a tautomer thereof and a compound represented by the following Formula (1-B2) and a tautomer thereof:

Formula (1-A2)

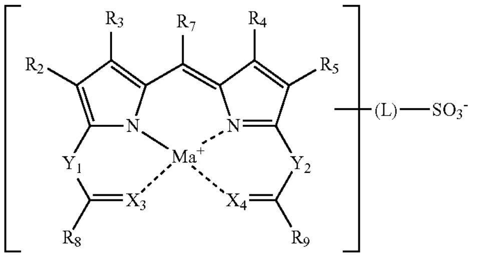

Formula (1-B2)

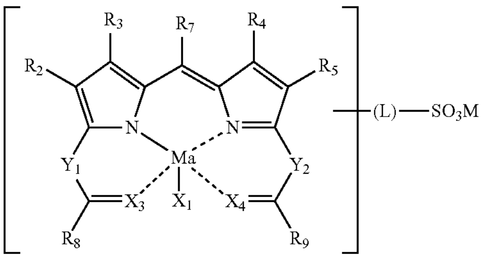

wherein, in Formula (1-A2) or Formula (1-B2), $R_2$ to $R_5$ each independently represent a hydrogen atom or a substituent; $R_7$ represents a hydrogen atom, a halogen atom, an alkyl group, an aryl group, or a heterocyclic group; $R_8$ and $R_9$ each independently represent an alkyl group, an alkenyl group, an aryl group, a heterocyclic group, an alkoxy group, an aryloxy group, an amino group, an anilino group or a heterocyclic amino group; at least one of $R_2$ to $R_5$, $R_8$ and $R_9$ represents a substituent and any one of the substituents represented by $R_2$ to $R_5$, $R_8$ and $R_9$ is a divalent linking group to bind to $-(L)-SO_3^-$ or -(L)-$SO_3M$; M represents a hydrogen atom, or an organic base or metal atom necessary for neutralizing a charge; L represents an alkylene group, an aralkylene group, or an arylene group, or a divalent group which may be formed by a combination of divalent groups selected from the group consisting of an alkylene group, an aralkylene group, an arylene group, —O—, —S—, —$SO_2$—, —N(Ra)—, —COO—, —OCO—, —CON(Rb)—, —N(Rb)CO—, —N(Rb)COO—, —OOCN(Rb)—, —N(Rb)CON(Rc)—, —$SO_2$N(Rb)—, and —N(Rb)$SO_2$—, where Ra represents an alkyl group, an alkenyl group, an aryl group, a heterocyclic group, an acyl group, an alkylsulfonyl group, or an arylsulfonyl group and Rb and Rc each independently represent a hydrogen atom, an alkyl group, an alkenyl group, an aryl group, or a heterocyclic group; Ma represents a metal or metal compound which may form a complex; $X_1$ represents a group necessary for neutralizing a charge of Ma; $X_3$ and $X_4$ each independently represent NR, an oxygen atom, or a sulfur atom, where R represents a hydrogen atom, an alkyl group, an alkenyl group, an aryl group, a heterocyclic group, an acyl group, an alkylsulfonyl group, or an arylsulfonyl group; R and $R_8$ or $R_9$ may bind together to form a 5-membered, 6-membered, or 7-membered ring; $Y_1$ and $Y_2$ each independently represent NR or an oxygen atom, where R represents a hydrogen atom, an alkyl group, an alkenyl group, an aryl group, a heterocyclic group, an acyl group, an alkylsulfonyl group, or an arylsulfonyl group; $R_8$ and $Y_1$ may bind together to form a 5-membered, 6-membered, or 7-membered ring; and $R_9$ and $Y_2$ may bind together to form a 5-membered, 6-membered, or 7-membered ring.

2. The colored curable composition according to claim 1, wherein Ma represents Fe, Zn, Co, V═O, or Cu.

3. The colored curable composition according to claim 1, wherein Ma represents Zn.

4. A color filter comprising the colored curable composition according to claim 1.

5. A method of producing a color filter, comprising:

applying the colored curable composition according to claim 1 onto a support to form a coated film;

exposing the coated film to light through a mask, and developing the coated film to form a pattern image.

6. A colored curable composition, comprising:

a polymerizable monomer;

a radiation-sensitive compound; and at least one selected from the group consisting of a compound represented by the following Formula (C2) and a tautomer thereof and a compound represented by the following Formula (D2) and a tautomer thereof:

Formula (C2)

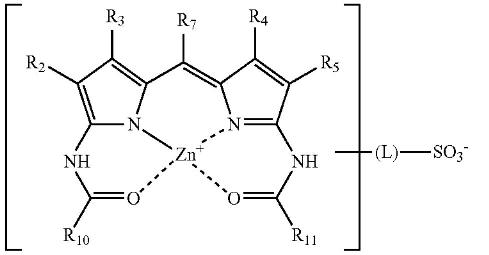

-continued

Formula (D2)

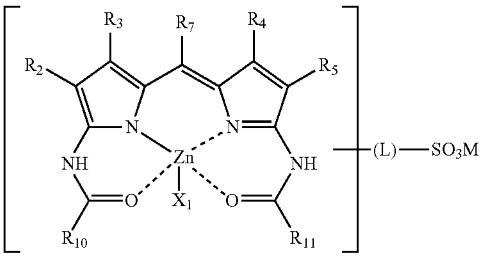

wherein, in Formula (C2) or Formula (D2), $R_2$ to $R_5$ each independently represent a hydrogen atom or a substituent; $R_7$ represents a hydrogen atom, a halogen atom, an alkyl group, an aryl group, or a heterocyclic group; $R_{10}$ and $R_{11}$ each independently represent an alkyl group, an alkenyl group, an aryl group, a heterocyclic group, an alkoxy group, an aryloxy group, an amino group, an anilino group, or a heterocyclic amino group; at least one of $R_2$ to $R_5$, $R_{10}$ and $R_{11}$ represents a substituent and any one of the substituents represented by $R_2$ to $R_5$, $R_{10}$ and $R_{11}$ is a divalent linking group that binds to -(L)-$SO_3^-$ or -(L)-$SO_3M$; M represents a hydrogen atom, or an organic base or metal atom necessary for neutralizing a charge; L represents an alkylene group, an aralkylene group, or an arylene group, or a divalent group which may be formed by a combination of divalent groups selected from the group consisting of an alkylene group, an aralkylene group, an arylene group, —O—, —S—, —$SO_2$—, —N(Ra)—, —COO—, —OCO—, —CON(Rb)—, —N(Rb)CO—, —N(Rb)COO—, —OOCN(Rb)—, —N(Rb)CON(Rc)—, —$SO_2$N(Rb)—, and —N(Rb)$SO_2$—, where Ra represents an alkyl group, an alkenyl group, an aryl group, a heterocyclic group, an acyl group, an alkylsulfonyl group, or an arylsulfonyl group and Rb and Rc each independently represent a hydrogen atom, an alkyl group, an alkenyl group, an aryl group, or a heterocyclic group; and $X_1$ represents a group necessary for neutralizing a charge of Zn.

7. A colorant, selected from the group consisting of a compound represented by the following Formula (1-A2) and a tautomer thereof and a compound represented by the following Formula (1-B2) and a tautomer thereof:

Formula (1-A2)

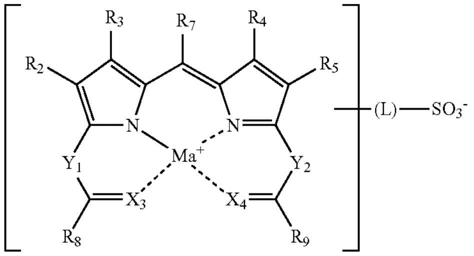

-continued

Formula (1-B2)

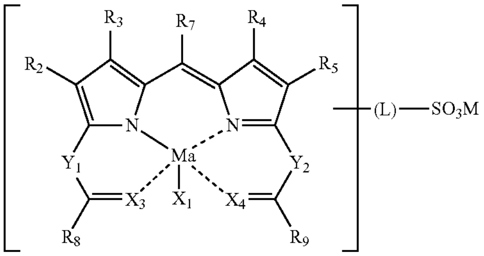

wherein, in Formula (1-A2) or Formula (1-B2), $R_2$ to $R_5$ each independently represent a hydrogen atom or a substituent; $R_7$ represents a hydrogen atom, a halogen atom, an alkyl group, an aryl group, or a heterocyclic group; $R_8$ and $R_9$ each independently represent an alkyl group, an alkenyl group, an aryl group, a heterocyclic group, an alkoxy group, an aryloxy group, an amino group, an anilino group or a heterocyclic amino group; at least one of $R_2$ to $R_5$, $R_8$ and $R_9$ represents a substituent and any one of the substituents represented by $R_2$ to $R_5$, $R_8$ and $R_9$ is a divalent linking group to bind to -(L)-$SO_3^-$ or -(L)-$SO_3M$; M represents a hydrogen atom, or an organic base or metal atom necessary for neutralizing a charge; L represents an alkylene group, an aralkylene group, or an arylene group, or a divalent group which may be formed by a combination of divalent groups selected from the group consisting of an alkylene group, an aralkylene group, an arylene group, —O—, —S—, —$SO_2$—, —N(Ra)—, —COO—, —OCO—, —CON(Rb)—, —N(Rb)CO—, —N(Rb)COO—, —OOCN(Rb)—, —N(Rb)CON(Rc)—, —$SO_2$N(Rb)—, and —N(Rb)$SO_2$—, where Ra represents an alkyl group, an alkenyl group, an aryl group, a heterocyclic group, an acyl group, an alkylsulfonyl group, or an arylsulfonyl group and Rb and Rc each independently represent a hydrogen atom, an alkyl group, an alkenyl group, an aryl group, or a heterocyclic group; Ma represents a metal or metal compound which may form a complex; $X_1$ represents a group necessary for neutralizing a charge of Ma; $X_3$ and $X_4$ each independently represent NR, an oxygen atom, or a sulfur atom, where R represents a hydrogen atom, an alkyl group, an alkenyl group, an aryl group, a heterocyclic group, an acyl group, an alkylsulfonyl group, or an arylsulfonyl group; R and $R_8$ or $R_9$ may bind together to form a 5-membered, 6-membered, or 7-membered ring; $Y_1$ and $Y_2$ each independently represent NR or an oxygen atom, where R represents a hydrogen atom, an alkyl group, an alkenyl group, an aryl group, a heterocyclic group, an acyl group, an alkylsulfonyl group, or an arylsulfonyl group; $R_8$ and $Y_1$ may bind together to form a 5-membered, 6-membered, or 7-membered ring; and $R_9$ and $Y_2$ may bind together to form a 5-membered, 6-membered, or 7-membered ring.

8. The colorant according to claim 7, wherein Ma represents Fe, Zn, Co, V═O, or Cu.

9. The colorant according to claim 7, wherein Ma represents Zn.

* * * * *